US011589579B2

(12) United States Patent
Berg et al.

(10) Patent No.: US 11,589,579 B2
(45) Date of Patent: Feb. 28, 2023

(54) POLYMERIC PARTICLES CONTAINING MICROORGANISMS

(71) Applicants: Technische Universitat Graz, Graz (AT); Biotenzz Gesellschaft fur Biotechnologie mbH, Graz (AT)

(72) Inventors: Gabriele Berg, Graz (AT); Henry Muller, Graz (AT)

(73) Assignees: BIOTENZZ GESELLSCHAFT FÜR BIOTECHNOLOGIE MBH, Graz (AT); TECHNISCHE UNIVERSITÄT GRAZ, Graz (AT)

( * ) Notice: Subject to any disclaimer, the term of this patent is extended or adjusted under 35 U.S.C. 154(b) by 290 days.

(21) Appl. No.: 16/648,535

(22) PCT Filed: Sep. 24, 2018

(86) PCT No.: PCT/EP2018/075760
§ 371 (c)(1),
(2) Date: Mar. 18, 2020

(87) PCT Pub. No.: WO2019/057958
PCT Pub. Date: Mar. 28, 2019

(65) Prior Publication Data
US 2020/0215125 A1    Jul. 9, 2020

(30) Foreign Application Priority Data
Sep. 22, 2017  (WO) ............... PCT/EP2017/073994

(51) Int. Cl.
| *A01N 25/28* | (2006.01) |
| *A01N 63/20* | (2020.01) |
| *A61K 9/16* | (2006.01) |
| *A61K 35/74* | (2015.01) |
| *C12N 1/04* | (2006.01) |
| *C12N 1/20* | (2006.01) |
| *A01N 63/30* | (2020.01) |
| *A01N 63/22* | (2020.01) |
| *A01N 63/27* | (2020.01) |

(52) U.S. Cl.
CPC ............ *A01N 25/28* (2013.01); *A01N 63/20* (2020.01); *A01N 63/22* (2020.01); *A01N 63/27* (2020.01); *A01N 63/30* (2020.01); *A61K 9/1617* (2013.01); *A61K 9/1652* (2013.01); *A61K 35/74* (2013.01); *C12N 1/04* (2013.01); *C12N 1/20* (2013.01)

(58) Field of Classification Search
CPC ........ A01N 25/28; A01N 63/20; A01N 63/30; A61K 9/1617; A61K 9/1652; A61K 35/74
See application file for complete search history.

(56) References Cited

U.S. PATENT DOCUMENTS

| 2,200,532 | A | 5/1940 | Bond |
| 4,940,834 | A | 7/1990 | Hurley et al. |
| 5,041,290 | A | 8/1991 | Gindrat et al. |
| 5,113,619 | A | 5/1992 | Leps et al. |
| 5,229,291 | A | 7/1993 | Nielsen et al. |
| 5,292,507 | A | 3/1994 | Charley |
| 5,415,672 | A | 5/1995 | Fahey et al. |
| 5,475,010 | A * | 12/1995 | Trani ............... A61P 31/04 549/264 |
| 5,730,973 | A | 3/1998 | Morales et al. |
| 5,919,447 | A | 7/1999 | Marrone et al. |
| 5,994,117 | A | 11/1999 | Bacon et al. |
| 6,072,107 | A | 6/2000 | Latch et al. |
| 6,077,505 | A | 6/2000 | Parke et al. |
| 6,337,431 | B1 | 1/2002 | Tricoli et al. |
| 6,495,133 | B1 | 12/2002 | Xue |
| 6,602,500 | B1 | 8/2003 | Kharbanda et al. |
| 6,681,186 | B1 | 1/2004 | Denisov et al. |
| 6,689,880 | B2 | 2/2004 | Chen et al. |
| 6,823,623 | B2 | 11/2004 | Minato et al. |
| 7,037,879 | B2 | 5/2006 | Imada et al. |
| 7,084,331 | B2 | 8/2006 | Isawa et al. |
| 7,335,816 | B2 | 2/2008 | Kraus et al. |
| 7,341,868 | B2 | 3/2008 | Chopade et al. |
| 7,485,451 | B2 | 2/2009 | VanderGheynst et al. |
| 7,555,990 | B2 | 7/2009 | Beaujot |
| 7,632,985 | B2 | 12/2009 | Malven et al. |
| 7,763,420 | B2 | 7/2010 | Stritzker et al. |
| 7,906,313 | B2 | 3/2011 | Henson et al. |
| 7,977,550 | B2 | 7/2011 | West et al. |
| 8,143,045 | B2 | 3/2012 | Miasnikov et al. |

(Continued)

FOREIGN PATENT DOCUMENTS

| CA | 1041788 A | 11/1978 |
| CA | 1229497 A | 11/1987 |

(Continued)

OTHER PUBLICATIONS

Kragh et al, Role of multicellular aggregates in biofilm formation, American society for microbiology, vol. 7, issue 2, Mar./Apr. 2016 (Year: 2016).*
Lugtenberg, B., et al., "Plant-Growth-Promoting Rhizobacteria," Ann. Rev. Microbiol., 2009, pp. 541-556, vol. 63.
Lundberg, D.S., et al., "Practical Innovations for High-Throughput Amplicon Sequencing," Nat Methods, 2013, pp. 999-1002, vol. 10, No. 10.
Ma, Y., et al., "Plant Growth Promoting Rhizobacteria and Endophytes Accelerate Phytoremediation of Metalliferous Soils," Biotechnology Advances, 2011, pp. 248-258, vol. 29.

(Continued)

*Primary Examiner* — Mina Haghighatian
(74) *Attorney, Agent, or Firm* — Loza & Loza, LLP; Michael Fedrick

(57) ABSTRACT

The present invention relates to polymeric particles comprising a biodegradable polymer, and at least one microorganism in a total concentration of at least $10^8$ CFU/g dry weight that is stable for at least 35 weeks at 30° C. and optionally additional carriers and additives as well as to methods for producing polymeric particles and use thereof.

11 Claims, 16 Drawing Sheets

(56) References Cited

U.S. PATENT DOCUMENTS

| | | |
|---|---|---|
| 8,455,198 B2 | 6/2013 | Gao et al. |
| 8,455,395 B2 | 6/2013 | Miller et al. |
| 8,465,963 B2 | 6/2013 | Rolston et al. |
| 8,728,459 B2 | 5/2014 | Isawa et al. |
| 8,975,489 B2 | 3/2015 | Craven |
| 9,049,814 B2 | 6/2015 | Marx et al. |
| 9,113,636 B2 | 8/2015 | von Maltzahn et al. |
| 9,277,751 B2 | 3/2016 | Sword |
| 9,288,995 B2 | 3/2016 | von Maltzahn et al. |
| 9,295,263 B2 | 3/2016 | von Maltzahn et al. |
| 9,364,005 B2 | 6/2016 | Mitter et al. |
| 9,408,394 B2 | 8/2016 | von Maltzahn et al. |
| 9,532,572 B2 | 1/2017 | von Maltzahn et al. |
| 9,532,573 B2 | 1/2017 | von Maltzahn et al. |
| 9,545,111 B2 | 1/2017 | Sword |
| 9,622,485 B2 | 4/2017 | von Maltzahn et al. |
| 9,652,840 B1 | 5/2017 | Shriver et al. |
| 9,687,001 B2 | 6/2017 | Vujanovic et al. |
| 9,756,865 B2 | 9/2017 | Sword |
| 10,058,101 B2 | 8/2018 | von Maltzahn et al. |
| 10,076,120 B2 | 9/2018 | von Maltzahn et al. |
| 10,104,862 B2 | 10/2018 | Vujanovic et al. |
| 2005/0070435 A1 | 3/2005 | Chopade et al. |
| 2005/0072047 A1 | 4/2005 | Conkling et al. |
| 2006/0046246 A1 | 3/2006 | Zeng et al. |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1 | 9/2008 | Young et al. |
| 2008/0289060 A1 | 11/2008 | De Beuckeleer et al. |
| 2009/0155214 A1 | 6/2009 | Isawa et al. |
| 2010/0064392 A1 | 3/2010 | Yang et al. |
| 2010/0095396 A1 | 4/2010 | Voeste et al. |
| 2010/0205690 A1 | 8/2010 | Biasing et al. |
| 2010/0227357 A1 | 9/2010 | Redman et al. |
| 2011/0182862 A1 | 7/2011 | Green et al. |
| 2012/0108431 A1 | 5/2012 | Williams et al. |
| 2012/0131696 A1 | 5/2012 | Aayal et al. |
| 2012/0135017 A1* | 5/2012 | Harel .............. A61K 47/38 435/235.1 |
| 2012/0144533 A1 | 6/2012 | Craven |
| 2012/0149571 A1 | 6/2012 | Kloepper et al. |
| 2012/0178624 A1 | 7/2012 | Kaminskyj et al. |
| 2012/0324599 A1 | 12/2012 | Kerns et al. |
| 2013/0031673 A1 | 1/2013 | Grandlic et al. |
| 2013/0071425 A1 | 3/2013 | Vidal et al. |
| 2013/0079225 A1 | 3/2013 | Smith et al. |
| 2013/0150240 A1 | 6/2013 | Newman et al. |
| 2013/0233501 A1 | 9/2013 | Van Zyl et al. |
| 2014/0020136 A1 | 1/2014 | Van Der Wolf et al. |
| 2014/0109249 A1 | 4/2014 | Turner et al. |
| 2014/0115731 A1 | 4/2014 | Turner et al. |
| 2014/0147425 A1 | 5/2014 | Henn et al. |
| 2014/0342905 A1 | 11/2014 | Bullis et al. |
| 2015/0020239 A1 | 1/2015 | von Maltzahn et al. |
| 2015/0033420 A1 | 1/2015 | Rodriguez et al. |
| 2015/0126365 A1 | 5/2015 | Sword |
| 2015/0230478 A1 | 8/2015 | Vujanovic et al. |
| 2015/0242970 A1 | 8/2015 | Avey et al. |
| 2015/0335029 A1 | 11/2015 | Mitter et al. |
| 2015/0366217 A1 | 12/2015 | Vujanovic et al. |
| 2015/0368607 A1 | 12/2015 | Arnold et al. |
| 2015/0370935 A1 | 12/2015 | Starr |
| 2015/0373993 A1 | 12/2015 | von Maltzahn et al. |
| 2016/0021891 A1 | 1/2016 | von Maltzahn et al. |
| 2016/0150796 A1 | 6/2016 | von Maltzahn et al. |
| 2016/0174570 A1 | 6/2016 | Vujanovic et al. |
| 2016/0192662 A1 | 7/2016 | Sword |
| 2016/0205947 A1 | 7/2016 | Sword |
| 2016/0235074 A1 | 8/2016 | von Maltzahn et al. |
| 2016/0255844 A1 | 9/2016 | Mitter et al. |
| 2016/0260021 A1 | 9/2016 | Marek |
| 2016/0286821 A1 | 10/2016 | Sword |
| 2016/0290918 A1 | 10/2016 | Xu et al. |
| 2016/0316760 A1 | 11/2016 | Ambrose et al. |
| 2016/0316763 A1 | 11/2016 | Sword |
| 2016/0330976 A1 | 11/2016 | Mitter et al. |
| 2016/0338360 A1 | 11/2016 | Mitter et al. |
| 2016/0366892 A1 | 12/2016 | Ambrose et al. |
| 2017/0020138 A1 | 1/2017 | von Maltzahn et al. |
| 2017/0164619 A1 | 6/2017 | von Maltzahn et al. |
| 2017/0164620 A1 | 6/2017 | von Maltzahn et al. |
| 2017/0215358 A1 | 8/2017 | Franco et al. |
| 2017/0223967 A1 | 8/2017 | Mitter et al. |
| 2018/0020677 A1 | 1/2018 | Ambrose et al. |
| 2018/0092365 A1 | 4/2018 | Sword |
| 2018/0153174 A1 | 6/2018 | Riley et al. |
| 2018/0177196 A1 | 6/2018 | Sword |
| 2018/0213800 A1 | 8/2018 | Djonovic et al. |
| 2018/0249716 A1 | 9/2018 | Riley |
| 2018/0251776 A1 | 9/2018 | Riley |

FOREIGN PATENT DOCUMENTS

| | | |
|---|---|---|
| CA | 2562175 A1 | 4/2008 |
| CA | 2916678 A1 | 12/2014 |
| CA | 2960032 A1 | 3/2015 |
| CA | 2935218 A1 | 7/2015 |
| CA | 2953466 A1 | 12/2015 |
| CA | 2953697 A1 | 12/2015 |
| CN | 1604732 A | 4/2005 |
| CN | 101311262 A | 11/2008 |
| CN | 101423810 A | 5/2009 |
| CN | 101570738 A | 11/2009 |
| CN | 101693881 A | 4/2010 |
| CN | 102010835 A | 4/2011 |
| CN | 102168022 A | 8/2011 |
| CN | 102352327 A | 2/2012 |
| CN | 102533601 A | 7/2012 |
| CN | 103642725 A | 3/2014 |
| CN | 104388356 A | 3/2015 |
| CN | 104560742 A | 4/2015 |
| EP | 0192342 A2 | 8/1986 |
| EP | 0223662 A1 | 5/1987 |
| EP | 0378000 A2 | 7/1990 |
| EP | 0494802 A1 | 7/1992 |
| EP | 0818135 A1 | 1/1998 |
| EP | 1621632 A1 | 2/2006 |
| EP | 1935245 A1 | 6/2008 |
| EP | 2676536 A1 | 12/2013 |
| JP | 2009/072168 A | 4/2009 |
| KR | 20100114806 A | 10/2010 |
| KR | 101066283 | 9/2011 |
| KR | 101091151 B1 | 12/2011 |
| KR | 20130023491 A | 3/2013 |
| RU | 2043028 C1 | 9/1995 |
| WO | 1988/009114 | 1/1988 |
| WO | 1994/016076 | 7/1994 |
| WO | 2000/029607 A1 | 5/2000 |
| WO | 2001/083697 A2 | 11/2001 |
| WO | 2001/083818 A2 | 11/2001 |
| WO | 2002/065836 A2 | 8/2002 |
| WO | 2004/046357 A1 | 6/2004 |
| WO | 2005/003328 A1 | 1/2005 |
| WO | 2007/021200 A1 | 2/2007 |
| WO | 2007/107000 A1 | 9/2007 |
| WO | 2008/103422 A2 | 8/2008 |
| WO | 2009/012480 A2 | 1/2009 |
| WO | 2009/078710 A1 | 6/2009 |
| WO | 2009/126473 A1 | 10/2009 |
| WO | 2010/109436 A1 | 9/2010 |
| WO | 2010/115156 A2 | 10/2010 |
| WO | 2011/001127 A1 | 1/2011 |
| WO | 2011/082455 A1 | 7/2011 |
| WO | 2011/112781 A2 | 9/2011 |
| WO | 2011/117351 A1 | 9/2011 |
| WO | 2012/034996 A1 | 3/2012 |
| WO | 2013/016361 A2 | 1/2013 |
| WO | 2013/029112 A1 | 3/2013 |
| WO | 2013/090628 A1 | 6/2013 |
| WO | 2013/122473 A1 | 8/2013 |
| WO | 2013/177615 A1 | 12/2013 |
| WO | 2013/190082 A1 | 12/2013 |

(56) References Cited

FOREIGN PATENT DOCUMENTS

| | | |
|---|---|---|
| WO | 2014/046553 A1 | 3/2014 |
| WO | 2014/082950 A1 | 6/2014 |
| WO | 2014/121366 A1 | 8/2014 |
| WO | 2014/206953 A1 | 12/2014 |
| WO | 2014/210372 A1 | 12/2014 |
| WO | 2015/035099 A1 | 3/2015 |
| WO | 2015/069938 A1 | 5/2015 |
| WO | 2015/100431 A2 | 7/2015 |
| WO | 2015/100432 A2 | 7/2015 |
| WO | 2015/192172 A1 | 12/2015 |
| WO | 2015/200852 A2 | 12/2015 |
| WO | 2015/200902 A2 | 12/2015 |
| WO | 2016/057991 A1 | 4/2016 |
| WO | 2016/090212 A1 | 6/2016 |
| WO | 2016/109758 A2 | 7/2016 |
| WO | 2016/179046 A1 | 11/2016 |
| WO | 2016/179047 A1 | 11/2016 |
| WO | 2016/200987 A1 | 12/2016 |
| WO | 2018102733 A1 | 6/2018 |
| WO | 2018160244 A1 | 9/2018 |
| WO | 2018160245 A1 | 9/2018 |

OTHER PUBLICATIONS

Madi, L. et al., "Aggregation in Azospirillum brasilense Cd: Conditions and Factors Involved in Cell-to-Cell Adhesion," Plant Soil, 1989, pp. 89-98, vol. 115.

Mannisto, M.K., et al., "Characterization of Psychrotolerant Heterotrophic Bacteria From Finnish Lapland," Syst Appl Microbiol., 2006, pp. 229-243, vol. 29.

Mano, H., et al., "Culturable Surface and Endophytic Bacterial Flora of the Maturing Seeds of Rice Plants (Oryza saliva) Cultivated in a Paddy Field," Microbes Environ., 2006, vol. 21, No. 2.

Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.

Mao, W., et al., "Seed Treatment with a Fungal or a Bacterial Antagonist for Reducing Corn Damping-off Caused by Species of *Pythium* and *Fusarium*," Plant Disease, 1997, pp. 450-454, vol. 81, No. 5.

Marasco, R., et al., "A Drought Resistance-Promoting Microbiome is Selected by Root System Under Desert Farming," PLoS ONE, 2012, vol. 7, No. 10, 14 Pages.

Marquez, L. M., et al., "A Virus in a Fungus in a Plant: Three-Way Symbiosis Required for Thermal Tolerance," Science, 2007, pp. 513-515, vol. 315.

Mastretta, C., et al., "Endophytic Bacteria from Seeds of Nicotiana Tabacum Can Reduce Cadmium Phytotoxicity," Intl J Phytoremediation, 2009, pp. 251-267, vol. 11.

Mateos, P. F., et al., "Cell-Associated Pectinolytic and Cellulolytic Enzymes in Rhizobium leguminosarum biovartrifolii," Appl Environ Microbiol., 1992, pp. 816-1822, vol. 58, No. 6.

McDonald, D., et al., "An Improved Greengenes Taxonomy with Explicit Ranks for Ecological and Evolutionary Analyses of Bacteria and Archaea," ISME J., 2012, pp. 610-618, vol. 6.

McGuire, K.L., et al., "Digging the New York City Skyline: Soil Fungal Communities in Green Roofs and City Parks," PloS One, 2013, vol. 8, No. 3, 13 Pages.

Medina, P., et al., "Rapid Identification of Gelatin and Casein Hydrolysis Using TCA," J Microbiol Methods, 2007, pp. 391-393, vol. 69.

Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.

Mehnaz, S., et al., "Isolation and 16S rRNA sequence analysis of the beneficial bacteria from the rhizosphere of rice," Canada Journal of Microbiology, 2001, pp. 110-117, vol. 47, No. 2.

Mei, C., et al., "The Use of Beneficial Microbial Endophytes for Plant Biomass and Stress Tolerance Improvement," Recent Patents on Biotechnology, 2010, pp. 81-95, vol. 4.

Michel, B. E., et al., "The Osmotic Potential of Polyethylene Glycol 6000," Plant Physiol., 1973, pp. 914-916, vol. 51.

Misk, A., et al., "Biocontrol of chickpea root rot using endophytic actinobacteria", Biocontrol, vol. 56, No. 5, Mar. 12, 2011, pp. 811-822, XP036215297.

Moe, L. A., "Amino Acids in the Rhizosphere: From Plants to Microbes," American Journal of Botany, 2013, pp. 1692-1705, vol. 100, No. 9.

Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.

Mousa, W. K., et al., "The Diversity of Anti-Microbial Secondary Metabolites Produced by Fungal Endophytes: An Interdisciplinary Perspective," Front Microbiol, 2013, vol. 4, No. 65, 18 Pages.

Mundt, J.O., et al., "Bacteria Within Ovules and Seeds," Appl Environ Microbiol., 1976, pp. 694-698, vol. 32, No. 5.

Naik, B. S., et al., "Study on the diversity of endophytic communities from rice (*Oryza sativa* L.) and their antagonistic activities in vitro," Microbiological Research, 2009, pp. 290-296, vol. 164.

Naveed, M., "Maize Endophytes—Diversity, Functionality and Application Potential," University of Natural Resources and Life Sciences, 2013, pp. 1-266 and 81-87; Tables 1-3; Figure 2.

Nejad, P. et al., "Endophytic Bacteria Induce Growth Promotion and Wilt Disease Suppression in Oilseed Rape and Tomato," Biological Control, 2000, pp. 208-215, vol. 18.

Neslon, E.B., "Microbial Dynamics and Interactions in the Spermosphere," Ann. Rev. Phytopathol., 2004, pp. 271-309, vol. 42.

Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.

Nimnoi, P., et al., "Co-lnoculation of Soybean (*Glycin max*) wtth Actinomycetes and Bradyrhizobium Japonicum Enhances Plant Growth, Nitrogenase Activity and Plant Nutrition," Journal of Plant Nutrition, 2014, pp. 432-446, vol. 37.

Nishijima, K.A., et al., "Demonstraling Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.

Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.

Okunishi, S., et al., "Bacterial Flora of Endophytes in the Maturing Seeds of Cultivated Rice (*Oryza sativa*)," Microbes and Environment, 2005, pp. 168-177, vol. 20, No. 3.

Op De Beeck, M., et al., "Comparison and Validation of Some ITS Primer Pairs Useful for Fungal Metabarcoding Studies," PLOS One, Jun. 2014, vol. 9, Issue 6, e97629, pp. 1-11.

Orole, O. O., et al., "Bacterial and fungal endophytes associated with grains and roots of maize," Journal of Ecology and the Natural Environment, 2011, pp. 298-303, vol. 3, No. 9.

Partida-Martinez, L.P., et al., "The Microbe-Free Plant: Fact or Artifact?" Front Plant Sci., 2011, vol. 2, No. 100, 16 Pages.

Pearson, W.R., et al., "Rapid and Sensitive Sequence Comparison With FASTP and FASTA," Methods Enzymol., 2011, pp. 63-98, vol. 183.

Perez-Fernandez, M.A., et al., "Simulation of Germination of Pioneer Species Along an Experimental Drought Gradient," J Environ Biol , 2006, pp. 669-685, vol. 27, No. 4.

Perez-Miranda, S., et al., "O-CAS, A Fast and Universal Method for Siderophore Detection," J Microbiol Methods, 2007, pp. 127-131, vol. 70.

Petti, C. A., "Detection and Identification of Microorganisms by Gene Amplification and Sequencing," Clinical Infectious Diseases, 2007, pp. 1108-1114, vol. 44.

Phalip, V., et al., "A Method for Screening Diacetyl and Acetoin-Producing Bacteria on Agar Plates," J Basic Microbiol.,1994, pp. 277-280, vol. 34.

(56) References Cited

OTHER PUBLICATIONS

Philippot, L., et al., "Going Back to the Roots: The Microbial Ecology of the Rhizosphere," Nat Rev Microbiol., Nov. 2013, pp. 789-799, vol. 11.
Philrice Batac, Philippine Rice R&D Highlights, 2012, Area-Based R&D Projects, [online][Retrieved Aug. 11, 2016] Retrieved from the Internet URL:http://www.philrice.gov.ph/2012-rd-highlights/, 52 Pages.
Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.
Powell, W. A., et al., "Evidence of Endophytic Beauveria Bassiana in Seed-Treated Tomato Plants Acting as a Systemic Entomopathogen to Larval Helicoverpa zea (Lepidoptera: Noctuidae)," J. Entomol. Sci., 2009, pp. 391-396, vol. 44, No. 4.
Quadt-Hallmann, A, et al., "Bacterial Endophytes in Cotton: Mechanisms of Entering the Plant," Can J Microbiol., 1997, pp. 577-582, vol. 43.
Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.
Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.
Reiter, B., et al., "Response of Endophytic Bacterial Communities in Potato Plants to Infection with *Erwinia carotovora* subsp. *atroseptica*," Appl Environ Microbiol, 2001, pp. 2261-2268, vol. 68, No. 5.
Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.
Compant, S., et al., "Endophytic colonization of *Vitis vinfera* L. by Burkholderia phytofirmans strain PsJN: from the rhizosphere to inflorescence tissues," FEMS Microbiol Ecol, 2008, pp. 84-93, vol. 63.
NCBI GenBank: CP000653.1 "*Enterobacter* sp. 638, complete genome" Jan. 28, 2014, 5 Pages, Can be retrieved at<URL:https://www.ncbi.nlm.nih.gov/nuccore/CP000653.1>.
NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.
NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.
Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession; No. AY016368 sequence.
Hamayun, M., et al., "Cladosporium sphaerospermum as a new plant growth-promoting endophyte from the roots of *Glycine max* (L.) *merr*," World Journal of Microbiology and Biotechnology, Kluwer Academic Publishers, DO, vol. 25, No. 4, Feb. 15, 2009 (Feb. 15, 2009), pp. 627-632.
Hoffman, M., et al., "Diverse Bacteria Inhabit Living Hyphae of Phylogenetically Diverse Fungal Endophytes," Applied and Environmental Microbiology, Jun. 2010, p. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Hubbard, M., et al., 2011. "Agricultural Potential of Fungal Endophytes of Grasses, Cereals and Wheat," In: Wheat Genetics, Crops and Food Production. Nova Science Publishers Hauppauge, pp. 333-345.
Impullitti, A.E., et al., "Fungal endophyte diversity in soybean", Journal of Applied Microbiolog, vol. 114, No. 5, May 1, 2013, pp. 1500-1506.

Jung, C., et al., "The Effects of Endohyphal Bacteria on Anti-Cancer and Anti-Malaria Metabolites of Endophytic Fungi," Honors Thesis, University of Arizona, May 2012, 15 Pages.
Kim, M., et al., "Towards a taxonomic coherence between average nucleotide identity and 16S rRNAgene sequence similarity for species demarcation of prokaryotes", Int J Systematic Evolutionary Microbiol., 2014, vol. 64, pp. 346-351.
Klaubauf, S., et al., "Molecular diversity of fungal conmunities in agricultural soils from Lower Austria," Fungal Diversity, Aug. 13, 2010, pp. 65-75, vol. 44, No. 1.
Knapp, D., et al., "Inter- and intraspecific functional diversity of fungal root endophytes of semiarid sandy grasslands," Acta Microbiologica et Immunologica Hungarica, Nov. 2017, vol. 64, Issue Supplement 1, pp. 1-101.
Kumar, A., et al., "Bio-control potential of *Cladosporium* sp. (MCPL-461), against a noxious weed *Parthenium hysterophorus* L.," J Environ Biol, Mar. 2009, pp. 307-312, vol. 30, Issue 2.
Kusari, S., et al. "Chemical ecology of endophytic fungi: origins of secondary metabolites," Cell Press, Chem & Biol, vol. 19, pp. 792-798, 2012.
Liu, Y., et al., "Phylogenetic relationships among ascomycetes: evidence from an RNA polymerase II subunit," Mol. Biol. Evol. 1999. vol. 16, No. 12, pp. 1799-1808.
Mandyam, K., et al., "Mutualism-parasitism paradigm synthesized from results of root-endophyte models", Frontiers in Microbiology, vol. 5, Jan. 12, 2015, pp. 1-14.
Miyoshi-Akiyama, T., et al., "Multilocus Sequence Typing (MLST) for Characterization of Enterobacter cloacae," PLoS ONE, 2013, vol. 8, No. 6, 10 Pages, e66358.
Nassar, A., et al., "Promotion of plant growth by an auxin-producing isolate of the yeast *Williopsis saturnus* endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
O'Hanlon, K., et al., "Exploring the potential of symbiotic fungal endophytes in cereal disease suppression", Biological Control, vol. 63, No. 2, Sep. 5, 2012, pp. 69-78.
Rae, R., et al., "A subset of naturally isolated Bacillus strains show extreme virulence to the free-living nematodes *Caenorhabditis elegans* and *Pristionchus pacificus*", Environmental Microbiology, vol. 12, No. 11, 2010, pp. 3007-3021.
Riess, K., et al., "High genetic diversity at the regional scale and possible speciation in Sebacina epigaea and S. incrustans," BMC Evolutionary Biology, 2013, vol. 13, No. 102, 17 Pages.
Samways, M.J., et al., "Assessment of the Fungus Cladosporium Oxyspoum (BERK. and CURT.) As a Potential BioControl Agent Against Certain Homoptera," Elsevier Science Publishers B.V., Jan. 1, 1986, pp. 231-239.
Sarkar, S., et al., "New report of additional enterobacterial species causing wilt in West Bengal, India," Canadian Journal of Microbiology, 2015, vol. 61, No. 7, pp. 477-486.
Saunders, M., et al., "Host-Synthesized Secondary Compounds Influence the In Vitro Interactions between Fungal Endophytes of Maize", Applied and Environmental Microbiology, Nov. 9, 2007, pp. 136-142, vol. 74, No. 1.
Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.
Shiraishi, A., et al., "Nodulation in black locust by the ammaproteobacteria *Pseudomonas* sp. and the Betaproteobacteria *Burkholderia* sp", Systematic and Applied Microbiology, vol. 33, No. 5, Aug. 2010, pp. 269-274.
Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, vol. 46, pp. 381-387.
Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.

(56) References Cited

OTHER PUBLICATIONS

U'Ren, J.M., et al., "Host and geographic structure of endophytic and endolichenic fungi at the continental scale," American Journal of Botany, May 1, 2012, pp. 898-914, vol. 99, No. 5.

Valencia, E., et al., "Mini-review: Brazilian fungi diversity for biomass degradation," Fungal Genetics and Biology, 2013, pp. 9-18, vol. 60.

Vujanovic, V., et al., "Viability Testing of Orchid Seed and the Promotion of Colouration and Germination," Annals of Botany, Mar. 17, 2000, pp. 79-86, vol. 86.

Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.

Vujanovic, V., et al.,"Orchid seed viability testing by fungal bioassays and molecular phylogeny," Floriculture, ornamental and plant biotechnology, 2006, vol. 63, pp. 563-569.

Vujanovic, V., et al., "Mycovitality—a new concept of plant biotechnology," Canadian Journal Plant Pathol. 2007, vol. 29, p. 451.

Vujanovic, V., et al., "19th International Conference on *Arabidopsis*. Research Proceedings—ICAR13," Jul. 23-27, 2008, 264 Pages, Montreal, QC, Canada.

Vujanovic, V., et al., "Mycovitality and mycoheterotrophy: where lies dormancy in terrestrial orchid and plants with minute seeds?" Symbiosis, 2007, vol. 44, pp. 93-99.

Vujanovic, V., et al., "Seed endosymbiosis: a vital relationship in providing prenatal care to plants," Can. J. Plant Sci., NRC Research Press, Feb. 6, 2017, pp. 972-981, vol. 97.

Vujanovic, V., et al: "Fungal communities associated with durum wheat production system: A characterization by growth stage, plant organ and preceding crop", Crop Protection, Elsevier Science, GB, vol. 37, Feb. 19, 2012, pp. 26-34.

Yennamalli, R., et al., "Endoglucanases: insights into thermostability for biofuel applications", Biotech Biofuels, 2013, vol. 6, Issue 136, pp. 1-9.

Youssef, Y.A., et al., "Production of Plant Growth Substances by Rhizosphere Myoflora of Broad Bean and Cotton," Biologia Plantarum, 1975, pp. 175-181, vol. 17, No. 3.

Zhang, Y., et al., "BcGsl, a glycoprotein from Botrytis cinerea, elicits defence response and improves disease resistance in host plants. Biochemical and biophysical research communications," Biochemical and Biophysical Research Communications, 2015, vol. 457, No. 4, pp. 627-634.

Zhang, W., et al., Host range of Exserohilum monoceras, a potential bioherbicide for the control of Echinochloa species, Canadian Journal of Botany/ Journal Canadien de Botan, National Research Council, Ottawa, CA, vol. 75, Jan. 1, 1997, pp. 685-692.

Zhu et al., "*Helminthosporium velutinum* and *H. aquaticum* sp. nov. from aquatic habitats in Yunnan Province, China." Phytotaxa, 2016, vol. 253, No. 3, pp. 179-190.

Amatuzzi, R.F., et al., "Potential of endophytic fungi as biocontrol agents of Duponchelia fovealis (Zeller) (Lepidoptera:Crambidae," Brazilian Journal of Biology, Nov. 9, 2017, 7 Pages.

Artursson, V., et al., "Interactions between arbuscular mycorrhizal fungi and bacteria and their potential for stimulating plant growth", Environmental Microbiology, vol. 8, No. 1, Jan. 1, 2006, pp. 1-10.

Bing, La, et al., "Suppression of Ostrinia nubilalis (Hübner) (Lepidoptera: Pyralidae) by endophytic Beauveria bassiana (Balsamo) Vuillemin", Environmental Entomol, Entomological Society of America, College Park, MD, US, vol. 20, Jan. 1, 1991, pp. 1207-1211.

NCBI GenBank: Accession No. JX880250.1, "Enterobacteriaceae bacterium Clerol 16S ribosomal RNA gene, partial sequence," NIH, Jun. 24, 2015, 2 Pages, can be retrieved at <URL:https://www.ncbi.nlm.nih.gov/nucleotideIJX880250.1?report=genbank&logs=nuclalign &blast_rank=80 &RID=KWUPBV08015>.

PCT International Search Report and Written Opinion, PCT Application No. PCT/US2015/038110, dated Dec. 11, 2015, 36 Pages.

PCT International Search Report and Written Opinion for PCT/AU2018/050387, dated Jul. 12, 2018, 8 pages.

PCT International Search Report and Written Opinionfor PCT/US2018/051467, dated Mar. 25, 2019 26 pages.

Al-Askar AA, "Microbiological studies on the in vitro inhibitory effect of Streptomyces collinus albescens against some phytopathogenic fungi", African Journal of Microbiology Research, 2012, 6: 3277-3283 & GenBank Accession No. AB184101, May 20, 2008.

Ardakani, M.R. et al., "Absorption of N, P, K thorugh triple inoculatin of wheat (*Triticum aestivum* L.) by Azospirillurr brasilense, *Streptomyces* sp., Glomus intraradices and manure application," Physiol Mol Biol Plants, 2011, vol. 17, No. 2, pp. 181-192.

Barnett, S., et al., "Selection of microbes for control of Rhizoctonia root rot on wheat using a high throughput pathosystem", Biological Control, Jul. 6, 2017, 113: 45-57.

Bashan, Yoav Ed, et al., "Inoculants of plant growth-promoting bacteria for use in agriculture," Biotechnology Advances, Elsevier Publishing, Barking, GB, vol. 16, No. 4, Jul. 1, 1998, pp. 729-770, XP004123985.

Bashan, Yoav E., et al., "Alginate Beads as Synthetic Inoculant Carriers for Slow Release of Bacteria that Affect Plant Growth," Applied and Environmental Microbiology, pp. 1089-1098, May 1986.

Shenhua Li, et al., "Change in deep soil microbial communities due to long-term fertilization," Soil Biology and Biochemistry, vol. 75, Mar. 5, 2014, pp. 264-272, XP055530941.

Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 14(9):3214-3222.

De Santi, M. et al., "A combined morphologic and molecular approach for characterizing fungal microflora from a traditional Italian cheese (Fossa cheese)," Inter. Dairy J., 2010, vol. 10, No. 7, pp. 465-471.

Fatima Z et al, "Antifungal activity of plant growth-promoting rhizobacteria isolates against Rhizoctonia solani in wheat", African Journal of Biotechnology, 2009, 8:219-225.

GenBank Accession No. KY643705, Feb. 27, 2017.
GenBank Accession No. KF951483, Jan. 5, 2014.
GenBank Accession No. KJ152029, May 6, 2015.
GenBank Accession No. KJ162248, Apr. 8, 2014.

Govindarajan, M. et al., "Effects of the Inoculation of Burkholderia vietnamensis and Related Endophytic Diaztrophic Bacteria on Grain Yield of Rice", Microbiol Ecology, Apr. 4, 2007, 17 Pages.

Iverson, C., et al, "The taxonomy of Enterobacter sakazakii: proposal of a new genus *Cronobacter* gen. nov. and descriptions of *Cronobacter sakazakii* comb. nov. *Cronobacter sakazakii* subsp. *sakazakii*, comb, nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and *Cronobacter genomospecies* I", BMC Evolutionary Biology 2007, Apr. 17, 2017, 11 pages.

Joe, M.M. et al., "Development of alginate-based aggregate inoculants of *Methylobacterium* sp. and *Azospirillum brasilense* tested under in vitro conditions to promote plant growth," Journal of Applied Microbiology 2013, 116(2):408-423, XP055225426, Nov. 22, 2013.

Manoharan, M. J. et al., "Survival of flocculated cells in alginate and its inoculatin effect on growth and yield of maize underwater deficit conditions," EP J of Soil Biology, Gauthier-Villars, Montrouge, FR, vol. 50, Mar. 7, 2012, pp. 198-206, XP028421147.

Murali, Gopal, et al., "Microbiome Selection Could Spur Next-Generation Plant Breeding Strategies," Frontiers in Microbiology, vol. 7, Dec. 7, 2016, XP055531064.

United States Patent Office, Non-Final Office Action, U.S. Appl. No. 14/964,429, dated Aug. 9, 2016, 6 Pages.

United States Patent Office, Final Office Action, U.S. Appl. No. 14/964,429, dated May 31, 2017, 9 Pages.

United States Patent Office, Non-Final Office Action, U.S. Appl. No. 15/212,038, dated Sep. 21, 2016, 10 Pages.

United States Patent Office, Non-Final Office Action, U.S. Appl. No. 15/063,350, dated Nov. 10, 2016, 18 Pages.

United States Patent Office, Final Office Action, U.S. Appl. No. 14/614,193, dated Dec. 22, 2016, 13 Pages.

United States Patent Office, Final Office Action, U.S. Appl. No. 14/614,193, dated Jul. 18, 2017, 14 Pages.

(56) References Cited

OTHER PUBLICATIONS

United States Patent Office, Final Office Action, U.S. Appl. No. 14/614,193, dated May 3, 2018, 10 Pages.
United States Patent Office, Non-Final Office Action, U.S. Appl. No. 15/107,973, dated Apr. 10, 2017, 39 Pages.
United States Patent Office, Final Office Action, U.S. Appl. No. 15/107,973, dated Jan. 26, 2018, 20 Pages.
United States Patent Office, Final Office Action, U.S. Appl. No. 14/410,537, dated May 5, 2017, 9 Pages.
United States Patent Office, Non-Final Office Action, U.S. Appl. No. 15/034,862, dated May 19, 2017, 8 Pages.
United States Patent Office, Final Office Action, U.S. Appl. No. 15/034,862, dated Jan. 12, 2018, 14 Pages.
United States Patent Office, Non-Final Office Action, U.S. Appl. No. 14/916,514, dated Sep. 20, 2017, 31 Pages.
United States Patent Office, Non-Final Office Action, U.S. Appl. No. 15/143,398, dated Sep. 22, 2017, 17 Pages.
United States Patent Office, Non-Final Office Action, U.S. Appl. No. 15/143,394, dated Sep. 25, 2017, 15 Pages.
United States Patent Office, Non-Final Office Action, U.S. Appl. No. 15/107,965, dated Jun. 21, 2018, 27 Pages.
Wang, L. et al. Application of Bioorganic Fertilizer Significantly Increased Apple Yields and Shaped Bacterial Community Structure in Orchard Soil.
Whelehan, et al., "Microencapsulation using vibrating technology," Journal of Microencapsulation 2011, vol. 28(8), pp. 669-688.
Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.
PCT Invitation to Pay Additional Fees, PCT Application No. PCT/CA2013/000091, dated Mar. 27, 2013, 2 Pages.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report, Application No. PCT/US2014/044427, dated Dec. 3, 2014, 9 Pages.
PCT International Search Report and Written Opinion, Application No. PCT/US2014/054160, dated Dec. 9, 2014, 21 Pages.
PCT Invitation to Pay Additional Fees, PCT Application No. PCT/US2014/064411, dated Feb. 5, 2015, 2 Pages.
PCT International Search Report and Written Opinion, International Application No. PCT/US2014/064411, dated Mar. 27, 2015, 15 Pages.
PCT Invitation to Pay Additional Fees, PCT Application No. PCT/US2014/072399, dated Apr. 14, 2015, 2 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, dated Apr. 16, 2015, 6 Pages.
PCT International Search Report and Written Opinion, Application No. PCT/US2014/072400, dated Jul. 8, 2015, 38 Pages.
PCT International Search Report and Written Opinion, Application No. PCT/AU2015/000360, dated Aug. 5, 2015, 12 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
PCT International Search Report and Written Opinion, PCT Application No. PCT/US2015/038187, dated Jan. 22, 2016, 36 Pages.
PCT Invitation to Pay Additional Fees, PCT Application No. PCT/US2015/068206, dated Apr. 12, 2016, 5 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Reporton Patentability, PCT Application No. PCT/US2016/030292, dated Aug. 2, 2017, 23 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
Djordjevic, D., et al., "Microtiter Plate Assay for Assessment of Listeria monocytogenes Biofilm Formation," Anni Environ Microbiol., 2002, pp. 2950-2958, vol. 68, No. 6.
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14860187.5, dated May 24, 2017, 9 Pages.
European Patent Office, Supplementary European Search Report, European Patent Application No. 14874589.6, dated Jul. 11, 2017, 9 Pages.
European Patent Office, Communication Pursuant to Article 94(3) EPC for European Patent Application No. EP 14748326.7, dated Feb. 15, 2018, 7 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report, European Patent Application No. EP 15812324.0, dated Nov. 2, 2017, 19 Pages.
United States Patent Office, Non-Final Office Action, U.S. Appl. No. 15/436,592, dated Aug. 30, 2017, 17 Pages.
United States Patent Office, Non-Final Office Action, U.S. Appl. No. 15/436,609, dated Aug. 30, 2017, 21 Pages.
Abarenkov, K., et al., "The UNITE Database for Molecular Identification of Fungi—Recent Updates and Future Perspectives," New Phvtol., 2010, pp. 281-285, vol. 186.
Abdellatif, L., et al., "Endophytic hyphal compartmentalization is required for successful symbiotic Ascomycota association with root cells," Mycological Research, 2009, pp. 782-791, vol. 113.
Abdou, R., et al., "Botryorhodines A-D, antifungal and cytotoxic depsidones from Botryosphaeria rhodina, an endophyte of the medicinal plant *Bidens pilosa*," Phytochemistry, 2010, vol. 71, pp. 110-116.
Adhikari, M., et al., "A New Record of Pseudeurotium bakeri from Crop Field Soil in Korea," The Korean Journal of Mycology, 2016, pp. 145-149, vol. 44.
Ahmad, F., et al., "Screening of Free-Living Rhizospheric Bacteria for Their Multiple Plant Growth Promotinq Activities," Microbiol Res., 2008, pp. 173-181, vol. 163.
Amann, R., et al., "The Identification of Microorganisms by Fluorescence in Situ Hybridisation," Curr Opin Biotechnol., 2001, pp. 231-236, vol. 12.
Apel, K., et al., "Reactive Oxygen Species: Metabolism, Oxidative Stress, and Signal Transduction," Annu Rev Plant Biol., 2004, pp. 373-399, vol. 55.

(56) References Cited

OTHER PUBLICATIONS

Arendt, K. R., et al., "Isolation of endohyphal bacteria from foliar Ascomycota and in vitro establishment of their symbiotic associations," Appl Environ. Microbiol., 2016, pp. 2943-2949, vol. 82, No. 10.

Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.

Bacon, C. W, et al., "Isolation, In Planta Detection, and Uses of Endophytic Bacteria for Plant Protection," Manual of Environmental Microbiology, 2007, pp. 638-647.

Baker, K. F., et al., "Dynamics of Seed Transmission of Plant Pathogens," Annu Rev. Phytopathol., 1966, pp. 311-334, vol. 4.

Baltruschat, H., et al., "Salt tolerance of bariey induced by the root endophyte *Piriformospora indica* is associated with a strong increase in antioxidants," New Phytologist., 2008, pp. 501-510, vol. 180.

Bensch, K., et al., "Species and ecological diversity within the Cladosporium cladosporioides complex (Davidiellaceae, Capnodiales)," Studies in Mycology, 2010, pp. 1-94, vol. 67.

Block, C. C., et al., "Seed Transmission of Pantoea stewartii in Field and Sweet Corn," Plant Disease, 1998, pp. 775-780, vol. 82.

Brinkmeyer, R et al., "Uncultured Bacterium Clone ARKMP-100 16S Ribosomal RNA Gene, Partial Sequence," NCBI GenBank Accession No. AF468334, Submitted Jan. 14, 2002.

Brodie, E.L., et al., "Uncultured Bacterium Clone BANW722 16S Ribosomal RNA Gene, Partial Sequence," NCBI GenBank Accession No. DQ264636, Submitted Oct. 25, 2005, 1 Page.

Bulgarelli, D., et al., "Structure and Functions of the Bacterial Microbiota of Plants," Annu Rev Plant Biol., 2013, pp. 807-838, vol. 64.

Büttner, D., et al., "Regulation and secretion of Xanthomonas virulence factors," FEMS Microbiology Reviews, 2010, pp. 107-133, vol. 34, No. 2.

Caporaso, J.G., et al., "Ultra-High-Throughput Microbiol Community Analysis on the Illumina HiSeq and MiSeq Platforms," ISME J., 2012, pp. 1621-1624, vol. 6.

Castillo, D., et al., "Fungal Entomopathogenic Endophytes: Negative Effects on Cotton Aphid Reproduction in Greenhouse and Field Conditions," Power Point Presentation dated Mar. 23, 2013, 21 Pages.

Cavalier-Smith, T., "A Revised Six-Kingdom System of Life," Biol Rev Camb Philos Soc., 1998, pp. 203-266, vol. 73.

Chagas, F., et al., "A Mixed Culture of Endophytic Fungi Increases Production of Antifungal Polyketides," J. Chem. Ecol., Oct. 2013, pp. 1335-1342, vol. 39.

Clark, E. M., et al., "Improved Histochemical Techniques for the Detection of Acremonium coenophilum in Tall Fescue and Methods of in vitro Culture of the Fungus," J Microbiol Methods, 1983, pp. 149-155, vol. 1.

Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.

Trichoderma definition, 2016, 6 Pages, [online] [Retrieved on Sep. 16, 2016,] Retrieved from the Internet <URL: https://en.wikipedia.org/wiki/Trichoderma>.

Trotel-Aziz, P., et al., "Characterization of New Bacterial Biocontrol Agents *Acinetobacter, Bacillus, Pantoea and Pseudomonas* spp. Mediating Grapevine Resistance Against Botrytis cinerea," Environmental and Experimental Botany, 2008, pp. 21-32, vol. 64.

Truyens, S., et al., "Changes in the Population of Seed Bacteria of Transgenerationally Cd-Exposed *Arabidopsis thaliana*," Plant Biol., 2013, pp. 971-981, vol. 15.

Usadel, B., et al., "The Plant Transcriptome-From Integrating Observations to Models," Front Plant Sci., 2013, pp. 1-3, vol. 4., Article 48, 3 Pages.

Vacheron, J., et al., "Plant Growth-Promoting Rhizobacteria and Root System Functioning," Frontiers Plant Sci., 2013, vol. 4, Article 356, 19 Pages.

Valencia, C. U., et al., "Endophytic Establishment as an Unintended Consequence of Biocontrol with Fungal Entomopathogens," Power Point Presentation dated Jan. 7, 2013, 10 Pages.

Van Der Lelie, D., et al., "Poplar and its Bacterial Endophytes: Coexistence and Harmony," Critical Rev Plant Sci., 2009, pp. 346-358, vol. 28.

Verkley, G., et al., "Paraconiothyrium, a new genus to accommodate the mycoparasite *Coniothyrium minitans*, anamorphs of Paraphaeosphaeria, and four new species," Studies in Mycology, 2004,; pp. 323-335, vol. 50.

Vining, K., et al., "Methylome Reorganization During in vitro Dedifferentiation and Regeneration of Populus trichocarpa," BMC Plant Biol., 2013, vol. 13, No. 92, 15 Pages.

Viruel, E., et al., "Pseudomonas thiveralensis Strain IEHa 16S Ribosomal RNA Gene, Partial Sequence," NCBI GenBankAccession No. GQ169380.1, Submitted May 15, 2009, 1 Page.

Visagie, C.M., et al., "Identification and nomenclature of the genus *Penicillium*," Studies in Mycology, Jun. 2014, pp. 343-371, vol. 78.

Waller, F., et al., "The Endophytic Fungus *Piriformospora indica* Reprograms Barley to Salt-Stress Tolerance, Disease Resistance, and Higher Yield," PNAS, 2005, pp. 13386-13391, vol. 102, No. 38.

Wang, B., et al., "Fungal endophytes of native *Gossypium* species in Australia," Mycological Research, 2007, pp. 347-354, vol. 111, No. 3.

Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.

Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.

Waqas, M., et al., "Endophytic Fungi Produce Gibberellins and Indoleacetic Acid and Promotes Host-Plant Growth during Stress," Molecules, 2012, pp. 10754-10773, vol. 17.

Weindling, R., "Relation of dosage to control of cotton seedling diseases by seed treatment," Plant Disease Reporter, 1943, 27, pp. 68-70.

White, J. F., et al., "A Proposed Mechanism for Nitrogen Acquisition by Grass Seedlings Through Oxidation of Symbiotic Bacteria," Symbiosis, 2012, pp. 161-171, vol. 57.

Wiegand, I., et al., "Agar and Broth Dilution Methods to Determine the Minimal Inhibitory Concentration (MIC) of AntiMicrobiol Substances," Nature Protocols, 2008, pp. 163-175, vol. 3, No. 2.

Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings" Worid J Microbiol Biotechnol., 2014, pp. 835-845, vol. 30.

Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.

Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.

Yezerski, A., et al., "The Effects of the Presence of Stored Product Pests on the Microfauna of a Flour Community," Journal of Applied Microbiology, 2005, pp. 507-515, vol. 98.

Zhang, J., et al. "Isolation and Characterization of Plant Growth-Promoting Rhizobacteria from Wheat Roots by Wheat Germ Agglutinin Labeled with Fluorescein Isothiocyanate", The Journal Of Microbiology, Apr. 27, 2012, vol. 50, No. 2, pp. 191-198, GenBank Accession No. JN210900.

Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.

Zhou, W., et al., "Effects of the Fungal Endophyte *Paecilomyces* sp. in Cotton on the Roo-Knot Nematode *Meloidogyne incognita*," poster dated Jan. 7, 2013.

Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.

(56) References Cited

OTHER PUBLICATIONS

Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.

Abello, J., et al., "Agrobacterium-mediated transformation of the endophytic fungus *Acremonium implicatum* associated with Brachiaria grasses", Mycological Research, pp. 407-413, vol. 112, Pt 3.

Antony-Badu, S., et al., "Multiple Streptomyces species with distinct secondary metabolomes have identical 16S rRNA gene sequences." Scientific Reports 7.1, Sep. 2017, No. 7, 11089, pp. 1-8.

Bandara, WM.M.S., et al., "Interactions among endophytic bacteria and fungi: effects and potentials" Journal of Biosciences, Dec. 2006, vol. 31, No. 5, pp. 645-650.

Bragantia, et al., "Identificaqao e Avaliaqao de Rizobacterias Isoladas de Raizes de Milho," Jan. 1, 2010, pp. 905-911, Retrieved from the Internet: URL:http://www.scielo.br/pdf/brag/v69n4/v69n4a17.pdf (With English Abstract).

De Medeiros, L., et al., "Evaluation of Herbicidal Potential of Depsides from Cladosporium uredinicola an Endophytic Fungus found in Guava Fruit," J Braz. Chem. Soc., 2012, vol. 23, No. 8, p. 1551-1557.

Fox, G., et al., "How close is close: 16S rRNA sequence identity may not be sufficient to guarantee species identity." International Journal of Systematic and Evolutionary Microbiology 42.1, 1992, pp. 166-170.

NCBI, GenBank Accession No. XP_002568042, Aug. 14, 2009, 4 Pages, Berg, V.D., et al., "Genome sequencing and analysis of the filamentous fungus," Nat. Biotechnol. 26 (10), 1161-1168 (2008).

Goudjal, Y., et al., "Biocontrol of Rhizoctonia solani damping-off and promotion of tomato plant growth by endophytic actinomycetes isolated from native plants of Algerian Sahara", Microbiological Research, 2014, vol. 169, No. 1, pp. 59-65.

Guo, X., et al., "Red Soils Harbor Diverse Culturable Actinomycetes That Are Promising Sources of Novel Secondary Metabolites", Applied and Environmental Microbiology, Feb. 27, 2015, vol. 81, No. 9, pp. 3086-3103.

Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.

Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.

Ogbo, F., et al., "Some Characteristics of a Plant Growth Promoting; iEnterobacter/isp. Isolated from the Roots of Maize", Advances in Microbiology, Jan. 1, 2012, vol. 02, No. 03, pp. 368-374.

Partida-Martinez, L.P., et al., "Endosymbiont-Dependent Host Reproduction Maintains Bacterial-Fungal Mutualism", Current Biology, May 1, 2007, vol. 17, No. 9, pp. 773-777.

"Sequence Alignment of JQ047949 with Instant Seq ID No. 2," Search conducted on Jan. 2, 2019, 2 pages.

Sharma et al., "Detection and identification of bacteria intimately associated with fungi of the order Sebacinales", Cellular Microbiology, Aug. 5, 2008, pp. 2235-2246, vol. 10, No. 11.

Yashiro et al., "Effect of Streptomycin Treatment on Bacterial Community Structure in the Apple Phyllosphere," PLOS One, May 21, 2012, vol. 7, No. 5, 10 pages.

Abdellatif, L., et al., "Characterization of virulence and PCR-DGGE profiles of Fusarium avenaceum from western Canadian Prairie Ecozone of Saskatchewan," Canadian Journal of Plant Pathology, 2010, pp. 468-480.

Abou-Shanab, R.A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.

Amatuzzi, R.F., et al., "Universidade Federal Do Parana," Jan. 1, 2014, 52 Pages. (With English Abstract).

Aveskamp, M., et al., "DNA phylogeny reveals polyphyly of Phoma section Peyronellaea and multiple taxonomic novelties," Mycologia, 2009, vol. 101, No. 3, pp. 363-382.

Azcon, R., et al., "Selective interactions between different species of mycorrhizal fungi and Rhizobium meliloti strains, and their effects on growth, N2-fixation (15N) and nutrition of *Medicago sativa* L.," New Phytol., 1991, vol. 117, pp. 399-404.

Bethlenfalvay, G., et al., "Mycorrhizal fungi effects on nutrient composition and yield of soybean seeds", Journal of Plant Nutrition, vol. 20, pp. 4-5, Apr. 1, 1997, pp. 581-591.

Clay, K., "Effects of fungal endophytes on the seed and seedling biology of Lolium perenne and Festuca arundinacea," Oecologia, 1987, pp. 358-362, vol. 73.

Clough, S. J., et al., "Floral Dip: A Simplified Method for Agrobacterium-mediated Transformation of *Arabidopsis thaliana*," Plant J., 1998, pp. 735-743, vol. 16, No. 6.

Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.

Cottyn, B., et al., "Phenotypic and genetic diversity of rice seed-associated bacteria and their role in pathogenicity and biological control," Journal of Applied Microbiology, 2009, pp. 885-897, vol. 107.

Cox, C. D., "Deferration of Laboratory Media and Assays for Ferric and Ferrous Ions," Methods Enzymol., 1994, pp. 315-329, vol. 235.

Craine, J. M., et al., "Global Diversity of Drought Tolerance and Grassland Climate-Change Resilience," Nature Climate Change, 2013, pp. 63-67, vol. 3.

Dalal, J.M., et al., "Utilization of Endophytic Microbes for Induction of Systemic Resistance (ISR) in Soybean (*Glycine max* (L) merril) Against Challenge Inoculation with R. solani," Journal of Applied Science and Research, 2014, pp. 70-84, vol. 2, No. 5.

Danhorn, T., et al., "Biofilm Formation by Plant-Associated Bacteria," Annu Rev Microbiol., 2007, pp. 401-422, vol. 61.

Daniels, R., et al., "Quorum Signal Molecules as Biosurfactants Affecting Swarming in Rhizobium etli," PNAS, 2006, pp. 14965-14970, vol. 103, No. 40.

Darsonval, A., et al., "The Type III Secretion System of *Xanthomonas fuscans* subsp. *fuscans* is involved in the Phyllosphere Colonization Process and in Transmission to Seeds of Susceptible Beans," Applied and Environmental Microbiology, 2008, pp. 2669-2678, vol. 74, No. 9.

Dbget, "Orthology: K14454," 2005, 2 pages, can be retrieved at <URL:http://www.genome.jp/dbget-bin/wwwoget?ko:K14454>.

De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.

De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.

De Souza, J. J., et al., "Terpenoids from Endophytic Fungi," Molecules, 2011, pp. 10604-10618, vol. 16, No. 12.

Dennis, C., et al., "Antagonistic Properties of Species Groups of Trichoderma," Trans Brit Mycol Soc, 1971, pp. 25-39, vol. 57, No. 1.

Desiro, A., et al., "Detection of a novel intracellular microbiome hosted in arbuscular mycorrhizal fungi," ISME Journal, 2014, pp. 257-270, vol. 8.

Don, R.H., et al., "Properties of Six Pesticide Degradation Plasmids Isolated From Alcaligenes Paradoxus and Alcaligenes eutrophus," J Bacteriol, 1981, pp. 681-686, vol. 145, No. 2.

Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012, 2 Pages.

Eberhard, A., et al., "Structural Identification of Autoinducer of Photobacterium fischeri Luciferase," Biochem., 1981, pp. 2444-2449, vol. 20.

Edgar, R. C., "Search and Clustering Orders of Magnitude Faster than BLAST," Bioinformatics, 2010, pp. 2460-2461, vol. 26, No. 19.

(56) References Cited

OTHER PUBLICATIONS

Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.
Ek-Ramos, M. J., et al., "Spatial and Temporal Variation in Fungal Endophyte Communities Isolated from Cultivated Cotton (*Gossypium hirsutum*)," PLoS ONE, 2013, vol. 8, No. 6, 13 Pages, e66049.
Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013.
El-Shanshoury, A. R., "Growth Promotion of Wheat Seedlings by *Streptomyces atroolivaceus*," Journal of Agronomy and Crop Science, 1989, pp. 109-114, vol. 163.
Emerson, D., et al., "Identifying and Characterizing Bacteria in an Era of Genomics and Proteomics," BioScience, 2008, pp. 925-936, vol. 58, No. 10.
Endre, G., et al., "A Receptor Kinase Gene Regulating Symbiotic Nodule Development," Nature, 2002, pp. 962-966, vol. 417.
Faria, D. C., et al., "Endophytic Bacteria Isolated from Orchid and Their Potential to Promote Plant Growth," World J Microbiol Biotechnol., 2013, pp. 217-221, vol. 29.
Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.
Fiehn, O., et al., "Metabolite Profiling for Plant Functional Genomics," Nature Biotechnol., 2000, pp. 1157-1161, vol. 8.
Fierer, N., et al., "Cross-Biome Metagenomic Analyses of Soil Microbiol Communities and Their Functional Attributes," Proc Natl Acad Sci USA, 2012, pp. 21390-21395, vol. 109, No. 52.
Fincher, G. B., "Molecular and Cellular Biology Associated with Endosperm Mobilization in Germinating Cereal Grains," Annu Rev Plant Physiol Plant Mol Biol., 1989, pp. 305-346, vol. 40.
Fisher, P. J., et al., "Fungal saprobes and pathogens as endophytes of rice (*Oryza sativa* L.)," New Phytol., 1992, pp. 137-143, vol. 120.
Fisher, P.R., et al., "Isolation and Characterization of the Pesticide-Degrading Plasmid pJP1 from Alcaligenes paradoxus," J Bacteriol., 1978, pp. 798-804, vol. 135, No. 3.
Franco, C., et al., "Actinobacterial Endophytes for Improved Crop Performance," Australasian Plant Pathology, 2007, pp. 524-531, vol. 36.
Fulthorpe, R. R., et al., "Distantly Sampled Soils Carry Few Species in Common," ISME J., 2008, pp. 901-910, vol. 2.
Gantner, S., et al., "Novel Primers for 16S rRNA-based Archaeal Community Analyses in Environmental Samples," J Microbiol Methods, 2011, pp. 12-18, vol. 84.
Gao, Z., et al., "Quantitation of Major Human Cutaneous Bacterial and Fungal Populations," J Clin Microbiol., 2010, pp. 3575-3581, vol. 48, No. 10.
Garazzino, S., et al., "Osteomyelitis Caused by Enterobacter cancerogenus Infection following a Traumatic Injury: Case Report and Review of the Literature," J Clin Microbiol, Mar. 2005, vol. 43, No. 3, pp. 1459-1461.
Gasser, I., et al., "Ecology and Characterization of Polyhydroxyalkanoate-Producing Microorganisms on and in Plants," FEMS Microbiol Ecol., 2010, pp. 142-150, vol. 70.
Gavrish, E, et al., "*Lentzea* sp. MS6 16S Ribosomal RNA Gene, Partial Sequence," NCBI GenBank Accession No. EF599958. Submitted May 9, 2007, 1 Page.
Gebhardt, J., et al., "Characterization of a single soybean cDNA encoding cytosolic and glyoxysomal isozymes of aspartate aminostransferase," Plant Molecular Biology, 1998, pp. 99-108, vol. 37.
GenBank: AF034210.1 "Glycine max aspartate aminotransferase glyoxysomal isozyme AAT1 precursor and aspartate aminotransferase cytosolic isozyme AAT2 (AAT) mRNA, complete eds," NCBI, May 26, 1998, 2 Pages, can be retrieved at <URL:https://www.ncbi.nlm.nih.gov/nuccore/AF034210>.

GenBank: NP_001237541.1, "aspartate aminotransferase glyoxysomal isozyme AAT1 precursor [Glycine max]," NCBI, Oct. 29, 2016, 2 Pages, can be retrieved at <URL:https://www.ncbi.nlm.nih.gov/protein/NP_001237541.1 >.
GenEmbl Database, GenEmbl Record No. KF673660, Sandberg, et al., "Fungal endophytes of aquatic macrophytes: diverse host-generalists characterized by tissue preferences and geographic structure," 2013, 35 Pages.
GenEmbl Database, GenEmbl Record No. KP991588, Huang, et al., "Pervasive effects of wildfire on foliar endophyte communities in montane forest trees," Mar. 2015, 35 Pages.
GenEmbl database, GenEmbl Record No. EU 977189, Jan. 21, 2009, 4 pages, Smith, S.A., et al., "Bioactive endophytes warrant intensified exploration and conservation," PloS One 3(8):E3052, 2008.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
Database Geneseq Database accession No. BAP97938 "Pantoea dispersa strain KACC91642P 16S rDNA sequence, SEQ ID 1." Aug. 15, 2013, 1 Page.
Gilmour, S. J., et al., "Overexpression of the Arabidopsis CBF3 Transcriptional Activator Mimics Multiple Biochemical Changes Associated with Cold Acclimation," Plant Physiol., 2000, pp. 1854-1865, vol. 124.
Giraldo, A., et al., "Phylogeny of Sarocladium (Hypocreales)," Persoonia, 2015, pp. 10-24, vol. 34.
Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.
Rodriguez, H., et al., "Expression of a Mineral Phosphate Solubilizing Gene From Erwinia herbicola in Two Rhizobacterial Strains," J Biotechnol., 2001, pp. 155-161, vol. 84.
Rodriguez, R.J., et al., "Stress Tolerance in Plants via Habitat-Adapted Symbiosis," ISME J., 2008, pp. 404-416, vol. 2.
Rodriguez-Navarro, D., et al., "Soybean Interactions with Soil Microbes, Agronomical and Molecular Aspects," Agronomy for Sustainable Development, 2011, pp. 173-190, vol. 31, No. 1.
Roessner, U., et al., "Metabolic Profiling Allows Comprehensive Phenotyping of Genetically or Environmentally Modified Plant Systems," Plant Cell, 2001, pp. 11-29, vol. 13.
Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.
Rosenblueth, A., et al., "Seed Bacterial Endophytes: Common Genera, Seed-to-Seed Variability and Their Possible Role in Plants," Acta Hort, 2012, pp. 39-48, vol. 938.
Rosenblueth, M., et al., "Bacterial Endophytes and Their Interactions With Host," Molecular Plant-Microbe Interactions, 2006, pp. 827-837, vol. 19, No. 8.
Ross, P.L., et al., "Multiplexed Protein Quantitation in *Saccharomyces cerevisiae* Using Amine—Reactive Isobaric fagging Reagents," Mol Cell Proteomics, 2004, pp. 1154-1169, vol. 3, No. 12.
Saleem, M., et al., "Perspective of Plant Growth Promoting Rhizobacteria (PGPR) Containing ACC Deaminase in Stress Agriculture," J Ind Microbiol Biotechnol, Oct. 2007, pp. 635-648, vol. 34.
Samac, D.A., et al., "Recent Advances in Legume-Microbe Interactions: Recognition, Defense Response, and Symbiosis from a Genomic Perspective," Plant Physiol., 2007, pp. 582-587, vol. 144.
Sardi, P , et al., "Isolation of Endophytic *Streptomyces* Strains from Surface Sterilized Roots," Applied and Environmental Microbiology, 1992, pp. 2691-2693, vol. 58, No. 8.
Sarwar, M., et al., "Tryptophan Dependent Biosynthesis of Auxins in Soil," Plant Soil, 1992, pp. 207-215, vol. 147.
Schmieder, R., et al., "Quality Control and Preprocessing of Metagenomic Datasets," Bioinformatics, 2011, pp. 863-864, vol. 27, No. 6.

(56) References Cited

OTHER PUBLICATIONS

Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.

Schwyn, B. et al., "Universal Chemical Assay for the Detection and Determination of Siderophores," Analytical Biochemistry, 1987, pp. 47-56, vol. 160.

Senthilkumar, M., et al., "Biocontrol Potential of Soybean Bacterial Endophytes Against Charcoal Rot Fungus, *Rhizoctonia batatiola*," Current Microbiology, 2009, vol. 58, pp. 288-293.

Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.

Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.

Shankar, M., et al.,"Root colonization of a rice growth promoting strain of Enterobacter cloacae," Journal of Basic Microbiology, 2011, pp. 523-530, vol. 51.

Singh, A K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011, 1 page.

Soares, M. M. C. N., et al., "Screening of Bacterial Strains for Pectinolytic Activity: Characterization of the Polygalacturonase Produced by Bacillus SP," Revista de Microbiolgia, 1999, pp. 299-303, vol. 30.

Soe, K.M., et al., "Effects of endophytic actinomycetes and Bradyrhizobium japonicum strains on growth, nodulation, Titrogen fixation and seed weight of different soybean varieties," Soil Science and Plant Nutrition, 2012, pp. 319-325, vol. 58, No. 3.

Soe, K.M., et al., "Low-Density Co-lnoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.

Sogonov, M.V., et al.,"The hyphomycete *Teberdinia hygrophila* gen. nov., sp. nov. and related anamorphs of *Pseudeurotium* species," Mycologia, May 2005, pp. 695-709, vol. 97, No. 3.

Song, M., et al., "Effects of Neotyphodium Endophyte on Genmination of Hordeum brevisubulatum under Temperature and Water Stress Conditions," Acta Agrestia Sinica, 2010, pp. 834-837, vol. 18, No. 6. (English Abstract).

Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.

Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.

Staudt, A. K., et al., "Variations in Exopolysaccharide Production by Rhizobium tropici," Arch Microbiol., 2012, pp. 197-206, vol. 194.

Strobel, G. A., "Endophytes as Sources of Bioactive Products," Microbes and Infection, 2003, pp. 535-544, vol. 5.

Sturz, A. V., et al., "Weeds as a Source of Plant Growth Promoting Rhizobacteria in Agricultural Soils," Can J Microbiol., 2001, pp. 1013-1024, vol. 47, No. 11.

Surette, M.A., et al. "Bacterial Endophytes in Processing Carrots (*Daucus carota* L. var. *sativus*): Their Localization, Population Density, Biodiversity and Their Effects on Plant Growth," Plant and Soil, 2003, pp. 381-390, vol. 253, No. 2.

Suto, M., et al., "Endophytes as Producers of Xylanase," J Biosci Bioeng., 2002, pp. 88-90, vol. 93, No. 1.

Sword, G., "Manipulating Fungal Endophytes to Protect Plants from Insects and Nematodes," Power Point Presentation dated Aug. 7, 2013, 48 Pages.

Sword, G., et al., "Manipulating Fungal Endophytes for the Protection of Cotton in the Field," Power Point Presentation dated Jan. 7, 2013.

Sword, G., et al., "Field Trials of Potentially Beneficial Fungal Endophytes in Cotton," Power Point Presentation dated Jan. 7, 2013, 17 Pages.

Sword, G., "Fungal Endophytes to Protect Cotton from Insects and Nematodes," Power Point Presentation dated Dec. 7, 2012, 20 Pages.

Sword, G., "Natural Enemies—The Forgotten Basis of IPM?," Power Point Presentation dated Sep. 6, 2013, 33 Pages.

Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.

Taghavi, S., et al., "Genome Sequence of the Plant Growth promoting Endophytic *Bacterium enterobacter* sp. 638", PLoS Genet., May 2010, vol. 6, Issue 5, e1000943, pp. 1-15.

Tamura, K., et al., "Estimation of the No. of nucleotide substitutions in the control region of mitochondrial DNA in humans and chimpanzees," Molecular Biology and Evolution, 1993, vol. 10, No. 3, pp. 512-526.

Taylor, A.G., et al., "Concepts and Technologies of Selected Seed Treatments," Annu. Rev. Phytopathol., 1990, pp. 321-339, vol. 28.

Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.

Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.

Thakur, A., et al., "Enhanced Resistance to Spodoptera litura in Endophyte Infected Cauliflower Plants," Environmental Entomology, Apr. 1, 2013, pp. 240-246, vol. 42, No. 2.

Thakur, A., et al., "Suppression of Cellular Immune Response in Spodoptera litura (Lepidoptera: Noctuidae) Larvae by Endophytic Fungi Nigrospora oryzae and Cladosporium uredinicola,", Annals of the Entomological Society of America, May 1, 2014, pp. 674-679, vol. 107, No. 3.

Theis, K. R., et al., "Uncultured Bacterium Clone GM2GI8201A64RC 16S Ribosomal RNA Gene, Partial Sequence," NCBI GenBank Accession No. JX051943, Submitted May 14, 2012, 1 Page.

Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.

Thomashow, M. F., "So What's New in the Field of Plant Cold Acclimation? Lots!," Plant Physiol., 2001, pp. 89-93, vol. 125.

Tokala, R. T., et al., "Novel Plant-Microbe Rhizosphere Interaction Involving Streptomyces Lydicus WYEC108 and the Pea Plant (*Pisum sativum*)," Applied and Environmental Microbiology, May 2002, pp. 2161-2171, vol. 68, No. 5.

Invitation to Pay Additional Fees, PCT Application No. PCT/US2015/038110, dated Sep. 22, 2015, 8 Pages.

NCBI GenBank: Accession No. XP55670271, "*Enterobacter* sp. MLB05 16S ribosomal RNA gene, partial sequence—Nucleotide", Jun. 9, 2012, 1 Page, can be retreived at URL:https//www.ncbi.nlm.nih gov/nuccore/J Q765415.1/.

NCBI GenBank: Accession No. XP55670274, "*Enterobacter* sp. CR 6-3 16S ribosomal RNA gene, partial sequence—Nucleotide", Mar. 27, 2013, 1 Page, can be retreived at URL:https://www.ncbi.nlm.nih.gov/nuccore/K C355340.

NCBI GenBank: Accession No. XP55670279, "Uncultured bacterium clone bb2s4 16S ribosomal RNA gene, partial seque—Nucleotide", May 6, 2005, 1 Page, can be retreived at URL:https://www.ncbi.nlm.nih.gov/nuccore/D Q068880.

European Patent Office, Communication Pursuant to Article 94(3) EPC for European Patent Application No. EP 14777213.1, dated Jun. 18, 2018, 4 Pages.

De Melo Pereira, G. V., et al. "A Multiphasic Approach for the Identification of Endophytic Bacterial in Strawberry Fruit and their Potential for Plant Growth Promotion," Microb. Ecology, 2012, pp. 405-417, vol. 63, No. 2.

(56) References Cited

OTHER PUBLICATIONS

Result 11 from a search in the GenEmbl database, GenEmbl Record No. EU 977189, Smith et al., "Bioactive endophytes warrant intensified exploration and conservation," PLoS One 3(8):E3052, 2008.
Result 3 from a search in the GenEmbl database, GenEmbl Record No. KF011597, Paenibacillus strain No. HA13, Park et al., "Isolation and characterization of humic substances-degrading bacteria from the subarctic Alaska grasslands," J Basic Microbiol, 2013.
PCT International Search Report and Written Opinion for PCT/US2018/051467, dated Feb. 4, 2019, 22 pages.
Chaves, J., et al., "Identification and Phylogeny of Streptomyces Based on Gene Sequences", Research Journal of Microbiology, vol. 13, No. 1, Dec. 15, 2017, pp. 13-20, XP055675917.
Girard, G., et al., "A novel taxonomic marker that discriminates between morphologically complex actinomycetes", Open Biology, vol. 3, No. 10, Oct. 2013, p. 130073,XP055675916.
Guo, Y., et al. "A multi locus phylogeny of the Streptomyces griseus 16S rRNA gene clade: use of multilocus sequence analysis for streptomycete systematics", International Journal of Systematic and Evolutionary Microbiology, vol. 58, No. 1,2008, pp. 149-159, XP055675936.
PCT Invitation to Pay Additional Fees, PCT Application No. PCT/US2017/064292, dated Mar. 6, 2018, 15 Pages.
PCT International Search Report and Written Opinion, PCT Application No. PCT/US2017/068255, dated Mar. 19, 2018, 14 Pages.
PCT International Search Report and Written Opinion PCT/AU2018/050387, dated Jul. 12, 2018 (Filing date is Apr. 27, 2018).
PCT International Search Report and Written Opinion for PCT/US2017/064292, dated May 11, 2018, 20 Pages.
Bentley, S.D., et al., Complete genome sequence of the model actinomycete Streptomyces coelicolor A3(2), Nature. May 9, 2002;417(6885):141-7. (Year: 2002).
Gabor, J., et al., "Mycorrhizal fungi effects on nutrient composition and yield of soybean seeds," Journal of Plant Nutrition, 20:4-5, 581-591, 1997.
Gopalakrishnan, S. et al., "Plant growth-promoting activities of Streptomyces spp. In sorghum and rice", SpringerPlus, 2/1/574, pp. 1-8, http://www.springerplus.com/content/2/1/574, 2013.
Groppe, K., et al., "Interaction between the endophytic fungus Epichloë bromicola and the grass Bromus erectus: effects of endophyte infection, fungal concentration and environment on grass growth and flowering," Mol Ecol., 3:1827-1835, 1999.
Hubbard, M., "Fungal Endophytes that Confer Heat and Drought Tolerance to Wheat," Doctoral dissertation, University of Saskatchewan, 2012.
Ikeda, H., et al., "Complete genome sequence and comparative analysis of the industrial microorganism Streptomyces avermitilis," Nat Biotechnol. May 2003;21 (5) :526-31. Epub Apr. 14, 2003. (Year: 2003).
Lee, J., et al., "Streptomyces koyangensis sp. nov., a novel actinomycete that produces 4-phenyl-3-butenoic acid," Int J Syst Evol Microbial. Jan. 2005;55(Pt 1):257-62. (Year: 2005).
Lind, A., et al., "Drivers of genetic diversity in secondary metabolic gene clusters within a fungal species", PLOS Biology, Nov. 17, 2017, 26 pages.
Pacovsky, R., "Carbohydrate, protein and amino acid status of Glycine-Glomus-Bradyrhizobium symbioses," Physiologia Pantarium; 75:346-354, 1989).
Sha, T. et al., "Genetic diversity of the endemic gourmet mushroom Thelephora ganbajun from southwestern China", Microbiology (2008), 154, 3460-3468.
Sugita, T. et al., "Intraspecies Diversity of Cryptococcus laurentii as Revealed by Sequences of Internal Transcribed Spacer Regions and 28S rRNA Gene and Taxonomic Position of C. laurentii Clinical Isolates", Journal of Clinical Microbiology, Apr. 2000, p. 1468-1471.
Wiebold, M., et al., "Agriculture Experiment Station, College of Agriculture, Food & Natural Resources, University of Missouri, Special Report 589, pp. 1-124)."

Le, X.H., et al., "Effects of endophytic Streptomyces on the lucerne (Medicago sativa L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
European Patent Office, Supplementary European Search Report, European Patent Application No. 13874703.5, dated Jun. 21, 2016, 3 Pages.
Invitation to Pay Additional Fees, PCT Application No. PCT/US2015/038187, dated Oct. 14, 2015, 5 Pages.
Coombs, J. T., et al., "Isolation and Identification of Actinobacteria from Surface-Sterilized Wheat Roots," Applied and Environmental Microbiolog,, 2003, pp. 5603-5608, vol. 69, No. 9.
Laus, M. C., et al., "Role of Cellulose Fibrils and Exopolysaccharides of Rhizobium leguminosarum in Attachment to and Infection of Vicia sativa Root Hairs," Mol Plant Microbe Internet., 2005, pp. 533-538, vol. 16, No. 6.
United States Patent Office, Non-Final Office Action, U.S. Appl. No. 15/143,398, dated Sep. 22, 2017, 16 Pages.
PCT International Search Report and Wlitten Opinion, PCT Application No. PCT/US2015/068206, dated Jun. 27, 2016, 20 Pages.
PCT International Search Report and Wrrtten Opinion, PCT Application No. PCT/US2016/030292, dated Aug. 12, 2016, 20 Pages.
PCT International Search Report and Wrrtten Opinion, PCT Application No. PCT/US2016/030293, dated Aug. 11, 2016, 23 Pages.
PCT International Search Report and Wlitten Opinion, PCT Application No. PCT/US2016/036504, dated Nov. 4, 2016, 18 Pages.
GenEmbl Database, GenEmbl Record No. JN872548.1, 2 Pages.
Soe, K.M, et al, "Evaluation of effective Myanmar Bradyrhizobium strains isolated from Myanmar soybean and effects of coinoculation with Streptomyces griseoglavus P4 for nitrogen fixation", Soil science and plant nutrition 59.3 (2013): 361-370 (Year: 2013).
Ngom, A et al., "A novel symbiotic nitrogen-fixing member of the Ochrobactrum clade isolated from root nodues of Acacia mangium". J. Gen. Appl. Microbiol. (2004) 50: 17-27.
Trujillo, M.E et al., "Nodulation of Lupinus albus by strins of Ochrobactrum lupini sp. nov." Appl. Environ Microbiol Mar. 2005; 71(3): 1318-1327.
Bal, H.B et al., "Isolation of ACC deaminase producing PGPR from rice rhizosphere and evaluating their plant growth promoting activity under salt stress" Plant Soil (2013) 366: 93-105 doi: 10/1007/s11104-012-1402-5.
Chakraborty et al., "Evaluation of Ochrobactrum anthropi TRS-2 and its talcbased formulation for enhancement of growth of tea plants and management of brown root rot disease." Journal of Applied Microbiology, 2009, 107(2):625-634 DOI:10.1111/j.1365-2672.2009.04242.x <https://doi.org/10.1111/j.1365-2672.2009.04242.x.
Sulistiyani, et al., "Population and Diversity of Endophytic Bacteria Associated with Medicinal Plan Curumma zedoaria ", Microbiology Indonesia 8.2 (2014):4.
Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.
Darsonval, A., et al., "Adhesion and Fitness in the Bean Phyllosphere and Transmission to Seed of Xanthomonas fuscans subsp. fuscans," Molecular Plant-Microbe Interactions, 2009, pp. 747-757, vol. 22, No. 6.
Edgar, R. C., "Uparse: Highly Accurate OTU Sequences From Microbial Amplicon Reads," Nat. Methods, 2013, pp. 996-998, vol. 10, No. 10.
Gu, O., et al., "Glycomyces sambucus sp. nov., an endophytic actinomycete islolated from the stem of Sambucus adnata Wall," International Journal of Systematic and Evolutionary Microbiology, 2007, pp. 1995-1998, vol. 57.
Hardoim, P.R., et al., "Dynamics of Seed-Borne Rice Endophytes on Early Plant Growth Stages," PLoS ONE, 2012, vol. 7, No. 2, 13 Pages.

(56) References Cited

OTHER PUBLICATIONS

Hasana, R. C., et al., "A Rapid and Easy Method for the Detection of Microbial Cellulases on Agar Plates Using Gram's Iodine," Curr Microbiol., 2008, pp. 503-507, vol. 57.
Lundberg, D.S., et al., "Defining the Core *Arabidopsis thaliana* Root Microbiome," Nature, 2012, pp. 86-90, vol. 488, No. 7409.
Hanshew, A., et al., "Characterization of Actinobacteria Associated with Three Ant-Plant Mutualisms", Microbiol Ecology, Aug. 6, 2014, vol. 69, No. 1, pp. 192-203.
Langille, M.G.I. et al., "Predictive functional profiling of microbial communities using 16S rRNA marker; gene sequences," Nature Biotechnology, 2013, vol. 31, No. 9, pp. 814-821.
Li, M., et al., "ATP Modulates the Growth of Specific Microbial Strains", Current Microbiology, May 30, 2010, vol. 62, No. 1, pp. 84-89.
PCT Invitation to Pay Additional Fees, PCT Application No. PCT/US2017/064351, dated Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
European Patent Office, Supplementary European Search Report for European Patent Application No. 15810847.2, dated Feb. 28, 2018, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
NCBI GenBank: CP000653.1 "*Enterobacter* sp. 638, complete genome" ASM1632v1, Apr. 18, 2007, 2 Pages, Can be retrieved at <URL:https://www.ncbi.nlm.nih.gov/assembly/GCA000016325.1>.
NCBI GenBank: EBI accession No. Em STD:JQ759988, "*Dothideomycetes* sp. genotype 226 isolate FL0175 internal transcribed spacer 1, partial sequence; 5.85 ribosomal RNA gene and internal transcribed spacer 2, complete sequence; and 285 ribosomal RNA gene, partial sequence," May 17, 2012, 2 Pages.
GenBank: JN210900.1, "*Enterobacter* sp. WS05 16S ribosomal RNA gene, partial sequence," NCBI, Sep. 24, 2012, 1 Page, can be retrieved at<URL:https://www.ncbi.nlm.nih.gov/nuccore/jn210900>.
PCT International Search Report and Written Opinion for PCT/US2017/064361, dated May 11, 2018, 22 Pages.
PCT International Search Report and Written Opinion, PCT Application No. PCT/US2017/064292, dated May 11, 2018, 20 Pages.
European Patent Office, Extended European Search Report, European Patent Application No. EP 15876324.3, dated Jun. 12, 2018, 9 Pages.
Vjanovic, V., et al., "A comparative study of endophytic mycobiota in leaves of Acer saccharum in eastern North America," Mycological Progress, May 2002, pp. 147-154, vol. 1, Issue 2.
United States Patent Office, Non-Final Office Action, U.S. Appl. No. 14/766,065, dated Oct. 27, 2017, 11 Pages.
Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.
Chernin, L. S., et al., "Chitinolytic Activity in Chromobacterium violaceum: Substrate Analysis and Regulation by Quorum Sensing," J Bacteriol, 1998, pp. 4435-4441, vol. 180, No. 17.
Hain, T., et al., "Chitinolytic transgenes from Streptomyces albidoflavus as phytochemicals defences against; herbivorous insects, use in transgenic plants and effect in plant development", International Journal of Systematic Bacteriology, Jan. 1997, vol. 47, No. 1, pp. 202-206.
Johnston-Monje, D., "Microbial Ecology of Endophytic Bacteria in *Zea* Species as Influenced by Plant Genotype, Seed Origin, and Soil Environment," Thesis, University of Guelph, 2011, 230 Pages.

Orakçi GE et al., "Selection of antagonistic actinomycete isolates as biocontrol agents against root-rot fungi", Fresenius Environmental Bulletin, 2010, 19:417-424 & GenBank Accession No. GQ475299, Oct. 5, 2009.
R Core Team, "R: A Language and Environment for Statistical Computing," R Foundation for Statistical Computing, Vienna, Austria, May 2013, ISBN: 3-900051-07-0. Available online at http://www.R-25project.org/, 3604 Pages.
NCBI, GenBankAccession No. KX641980.1, Jul. 29, 2017, Scott, M., et al., "*Dothideomycetes* sp. isolate FT14-6 internal transcribed spacer 1, partial sequence; 5.8S ribosomal RNA gene and internal transcribed spacer 2, complete sequence; and large subunit ribosomal RNA gene, partial sequence," 2 Pages, Can be retrieved at<URL:https://www.ncbi.nlm.nih.gov/nuccore/KX641980>.
Weaver, p. F., et al., "Characterization of Rhodopseudomonas capsulata," Arch Microbiol., 1975, pp. 207-216, vol. 105.
Redman, R. S., et al.,"Thermotolerance Generated by Plant/Fungal Symbiosis," Science, Nov. 2002, vol. 298, 1 Page (with 4 pages of supplemental material).
You, Y., et al., "Analysis of Genomic Diversity of Endophytic Fungal Strains Isolated from the Roots of Suaeda iaponica and S. maritima for the Restoration of Ecosystems in Buan Salt Marsh," Korean Journal of Microbiology and iotechnology, 2012, pp. 287-295, vol. 40, No. 4. (with English Abstract).
Invitation to Pay Additional Fees, PCT Application No. PCT/CA2013/000091, dated Mar. 27, 2013, 2 Pages.
International Search Report and Written Opinion for PCT/EP2013/062976, dated Dec. 22, 2014, 9 Pages.
International Search Report and Written Opinion, Application No. PCT/US2014/054160, dated Dec. 9, 2014, 21 Pages.
Invitation to Pay Additional Fees, PCT Application No. PCT/US2014/064411, dated Feb. 5, 2015, 2 Pages.
International Search Report and Written Opinion, International Application No. PCT/US2014/064411, dated Mar. 27, 2015, 15 Pages.
International Search Report and Written Opinion, International Application No. PCT/US2014/072399, dated Jun. 26, 2015, 22 Pages.
Invitation to Pay Additional Fees, PCT Application No. PCT/US2014/072400, dated Apr. 16, 2015, 6 Pages.
International Search Report and Written Opinion, Application No. PCT/US2014/072400, dated Jul. 8, 2015, 38 Pages.
Abarenkov, K., et al., "PlutoF-A Web Based Workbench for Ecological and Taxonomic Research, with an Online Implementation for Fungal ITS Sequences," Evol Bioinform Online, 2010, pp. 189-196, vol. 6.
Castillo, D., et al., "Fungal Endophytes: Plant Protective Agents Against Herbivores," Power Point Presentation dated Aug. 4, 2013.
Hiatt, E.E., et al., "Tall Fescue Endophyte Detection: Commerical Immunoblot Test Kit Compared with Microscopic Analysis," Crop Science, 1999, pp. 796-799, vol. 39.
Johnston-Monje, D., et al., "Conservation and Diversity of Seed Associated Endophytes in *Zea* Across Boundaries of Evolution, Ethnography and Ecology," PLoS ONE, 2011, vol. 6, No. 6, 22 Pages.
Pedraza, R.O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.
Welty, R.E., et al., "Influence of Moisture Content, Temperature, and Length of Storage onSeed Germination and Survival of Endophytic Fungi in Seeds of Tall Fescue and Perennial Ryegrass," Phytopathyol., 1987, pp. 893-900, vol. 77, No. 6.
Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.
Li, Q., "Agrobacterium tumefaciens Strain TA-AT-10 16S Ribosomal RNA Gene, Partial Sequence: GenBank: KF673157.1," Submitted Dec. 16, 2013.
Gitaitis, R., et al., "The Epidemiology and Management of Seedborne Bacterial Diseases," Annu Rev Phytopathol., 2007, pp. 371-397, vol. 45.

(56) References Cited

OTHER PUBLICATIONS

Grondona, I., et al., "TUSAL®, a commercial biocontrol formulation based on Trichoderma," Bulletin OILB/SROP, 2004, pp. 285-288, vol. 27, No. 8.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hallman, J., et al., "Bacterial Endophytes in Agricultural Crops," Canadian J Microbiol., 1997, pp. 895-914, vol. 43.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, LE., "Reduction of Verticillium Wilt Symptoms in Cotton Following Seed Treatment with Trichoderma virens," Proceedings Beltwide Cotton Conferences, 2000, vol. 1. (Abstract), 1 Page.
Hardegree, S. P. et al., "Effect of Polyethylene Glycol Exclusion on the Water Potential of Solution—Saturated Filter Paper," Plant Physiol., 1990, pp. 462-466, vol. 92.
Hardoim, P. R., et al., "Assessment of Rice Root Endophytes and Their Potential for Plant Growth Promotion," In Hardoim, P.R., Bacterial Endophytes of Rice—Their Diversity, Characteristics and Perspectives, Groningen, 2011, Pages 77-100.
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Hepler, P. K., et al., "Polarized Cell Growth in Higher Plants," Annu Rev Cell Dev Biol., 2001, pp. 159-187, vol. 17.
Hibbett, D.S., et al., "A Higher-Level Phylogenetic Classification of the Fungi," Mycol Res., 2007, pp. 509-547, vol. 111.
Hill, N. S., et al., "Endophyte Survival during Seed Storage: Endophyte-Host Interactions and Heritability," Crop Sci., 2009, pp. 1425-1430, vol. 49.
Hill N. S., et al., "Endophyte Survival during Seed Storage: Endophyte-Host Interactions and Heritability," PowerPoint, Dept Crop Soil Sciences, University of Georgia, Nov. 16, 2012, 3 Pages.
Hinton, D. M., et al., "Enterobacter cloacae is an endophytic symbiont of corn," Mycopathologia, 1995, pp. 117-125, vol. 129.
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.
Hubbard, M., et al., "Fungal Endophytes Improve Wheat Seed Germination Under Heat and Drought Stress," Botany, 2012, pp. 137-149, vol. 90.
Humann, J., et al., "Complete genome of the onion pathogen Enterobacter cloacae EcWSU1 ," Standard in Genomic Sciences, Dec. 31, 2011, vol. 5, No. 3, pp. 279-286.
Hung, P.Q., et al., "Isolation and Characterization of Endophytic Bacteria in Soybean (*Glycine* sp.)," Omonrice, 2004, pp. 92-101, vol. 12.
Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.
Ikeda, S., et al., "The Genotype of The Calcium/Calmodulin-Dependent Protein Kinase Gene (CCaMK) Determines Bacterial Community Diversity in Rice Roots Under Paddy And Upland Field Conditions," Applied and Environmental Microbiology, 2011, pp. 4399-4405, vol. 77, No. 13.
Imoto, K., et al., "Comprehensive Approach to Genes Involved in Cell Wall Modifications in *Arabidopsis thaliana*," Plant Mol Biol., 2005, pp. 177-192, vol. 58.

Jalgaonwala, R., et al., "A Review on Microbiol Endophytes from Plants: A Treasure Search for Biologically Active Metabolites," Global Journal of Research on Medicinal Plants & Indigenous Medicine, 2014, pp. 263-277, vol. 3, No. 6.
Janda, J.M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.
Johnston-Monje, D., et al., "Plant and Endophyte Relationships: Nutrient Management," Comprehensive Biotechnol., 2011, pp. 713-727, vol. 4.
Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.
Kaga, H., et al., "Rice Seeds as Sources of Endophytic Bacteria," Microbes Environ., 2009, pp. 154-162, vol. 24, No. 2.
Kalns, L., et al., "The Effects of Cotton Fungal Endophytes in the Field on Arthropod Community Structure," Power Point Presentation dated Jan. 7, 2013, 17 Pages.
Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.
Khan, A.L., et al., "Salinity Stress Resistance Offered by Endophytic Fungal Interaction Between Penicillium minioluteum LHL09 and *Glycine max*. L," J. Microbiol. Biotechnol., 2011, pp. 893-902, vol. 21, No. 9.
Kruger, M., et al., "DNA-Based Species Level Detection of Glomeromycota: One PCR Primer Set for All Arbuscular Mycorrhizal Fungi," New Phytol., 2009, pp. 212-223, vol. 183.
Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.
Kuklinsky-Sobral, J., et al., "Isolation and characterization of soybean-associated bacteria and their potential for plant growth promotion," Environmental Microbiology, 2004, pp. 1244-1251, vol. 6, No. 12.
Kumar, S., et al., "MEGA7: Molecular Evolutionary Genetics Analysis version 7.0 for bigger datasets," Molecular Biology and Evolution, Mar. 22, 2016, vol. 33, pp. 1870-1874.
Labeda, D.P., et al., "Phylogenetic study of the species within the family Streptomycetaceae," Antonie van Leeuwenhoek, 2012, vol. 101, pp. 73-104, Springer.
Lanver, D., et al., "Sho1 and Msb2-Related Proteins Regulate Appressorium Development in the Smut Fungus *Ustilago aydis*," Plant Cell, 2010, pp. 2085-2101, vol. 22.
Le, X.H., et al., "Isolation and characterisation of endophytic actinobacteria and their effect on the early growth and Todulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.
Lehman, S.G., "Treat Cotton Seed," Review of Applied Mycology, 1945, 24, 369, 16 Pages.
Lehman, S.G., "Treat Cotton Seed," Research and Farming III, Progr. Rept., 1945, 3, 5, 16 Pages.
Leonard, C. A., et al., "Random Mutagenesis of the Aspergillus oryzae Genome Results in Fungal Antibacterial Activity," Int J Microbiol., 2013, vol. 2013, Article ID 901697, 6 Pages.
Li, H. M., et al., "Expression of a Novel Chitinase by the Fungal Endophyte in Poa ampla," Mycologia, 2004, pp. 526-536, vol. 96, No. 3.
Li, H., et al., "Endophytes and their role in phytoremediation," Fungal Diversity, 2012, pp. 11-18, vol. 54.
Liu, M., et al., "A Novel Screening Method for Isolating Exopolysaccharide-Deficient Mutants," Appl Environ Microbiol., 1998, pp. 4600-4602, vol. 64, No. 11.
Liu, Y., et al., "Investigation on Diversity and Population Succession Dynamics of Endophytic Bacteria from Seeds of Maize (*Zea mays* L., Nongda108) at Different Growth Stages," Ann Microbiol, 2013, pp. 71-79, vol. 63.
Liu, D., et al., "Osmotin Overexpression in Potato Delays Development of Disease Symptoms," Proc Natl Acad Sci USA, 1994, pp. 1888-1892, vol. 91.

(56) References Cited

OTHER PUBLICATIONS

Liu, Y., et al., "Study on Diversity of Endophytic Bacterial Communities in Seeds of Hybrid Maize and their Parental Lines," Arch Microbiol., 2012, pp. 1001-1012, vol. 194.
Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.
Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.
Lorck, H., "Production of Hydrocyanic Acid by Bacteria," Physiol Plant, 1948, pp. 142-146, vol. 1.

\* cited by examiner

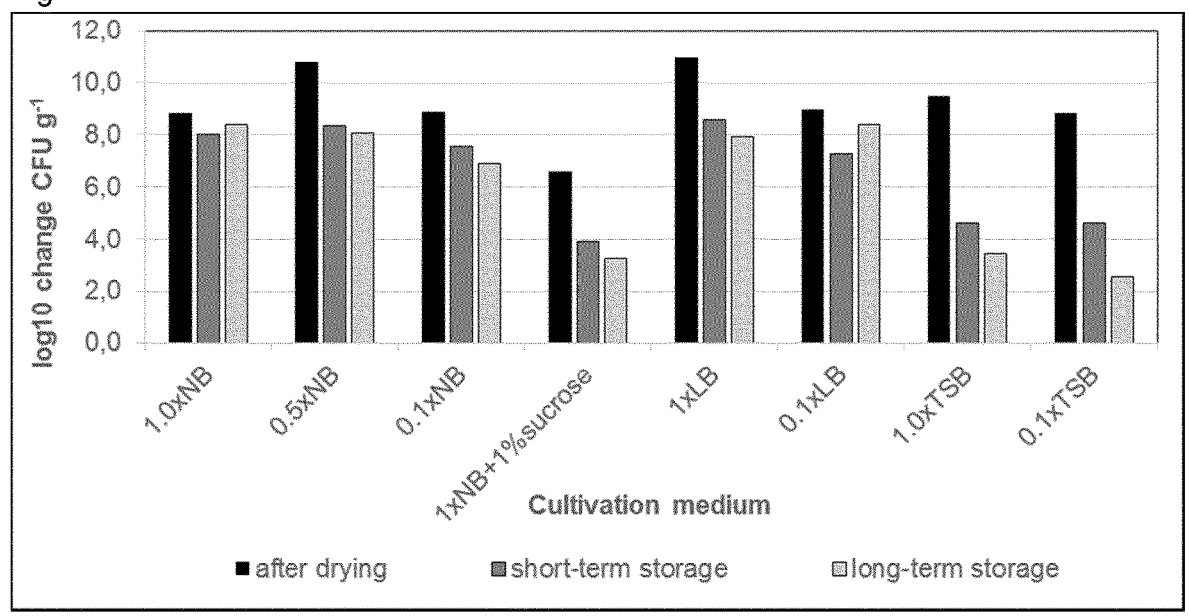

POLYMERIC PARTICLES CONTAINING MICROORGANISMS

RELATED APPLICATIONS

This application is the National Stage of International Application No. PCT/EP2018/075760, filed Sep. 24, 2018, which claims priority to International Application No. PCT/EP2017/073994, filed Sep. 22, 2017, which is incorporated herein by reference for all purposes.

FIELD OF THE INVENTION

The present invention relates to immobilization and cultivation methods inducing metabolic traits of long-term survival for improving the viability of microorganisms during storage and application and viable and stable microbial compositions.

BACKGROUND ART

The application of microorganisms for plant protection, growth promotion and fertilization purposes at commercial scale strongly depends on the reliability of microbial preparations. Particularly, when microbial agents are intended to be applied as additive in coatings for seed treatment processes, the requirements for the formulation are high. Apart from the general desiccation stress in dry formulations, microorganisms are additionally exposed to physical (e.g. shear forces), thermal as well as to detrimental chemicals (e.g., pesticidal agents). Except for some spore-forming bacteria, the majority of microorganisms are unable to cope with those stress moments and lose viability. To circumvent problems with the stability of microbial strains, mostly Gram-positive bacteria with spore-forming ability are currently being commercialized. Notwithstanding, sensitive Gram-negative bacteria possess a greater potential for biological plant protection and fertilization.

Bashan et al. (Appl Environ Microbiolv. 51(5); 1986) describe a method of inoculation of non-symbiotic rhizosphere bacteria in biodegradable polymeric substances. *Azospirillum brasilense* Cd is grown in nutrient broth to a final concentration of $10^9$ CFU/ml. The bacterial cells were then entrapped in alginate beads. After washing, the beads were again incubated to allow bacteria multiplication inside the beads. After washing, the beads were either kept at 4° C. in hermetically sealed flasks under moist conditions or as lyophilized beads.

Alginate is considered as the most common biomaterial for the encapsulation of bacterial and/or other type of cells. In presence of multivalent ions, alginate form three-dimensionally structured hydrogels in which bacterial cells are embedded (John R P et al., Crit Rev Biotechnol. 2011 September; 31(3):211-26). Although favoring in some extent the survivability of microbial cells due the high moisture rate, saturated alginate hydrogels are unsuitable and impractical for use as commercial products. In dried alginate aggregates with low moisture content, however, the vitally of the majority of microorganisms is severely impaired.

Usually, microbial cells are produced by submerged fermentation processes using liquid media. In a dispersed form, cells grow planktonically and possess a metabolism that favors multiplication rates and biomass gain, but reduces the robustness and compromise stress tolerance. Despite the application of protective additives to compensate missing resilience, survival rates are insufficient.

Despite much attention on the stabilization of microorganisms in formulations suitable for large scale applications, including seed treatment processes, no appropriate solution is currently available (Vemmer & Patel, 2013).

SUMMARY OF INVENTION

It is the objective of the present invention to provide for an improved immobilization-based cultivation and formulation method to induce metabolic traits of long-term survival for improving the viability of microorganisms during storage and application.

The object is solved by the subject of the present invention.

According to the invention there are provided polymeric particles comprising a polymer, at least one microorganism in a total concentration of at least $10^9$ CFU/g dry weight and optionally additional carriers and additives, wherein said polymeric particles are dry particles.

According to a further embodiment of the invention there are provided polymeric particles comprising a polymer, at least one microorganisms in a total concentration of at least $10^9$ CFU/g dry weight and optionally additional carriers and additives, wherein said at least one microorganism is comprised as self-organized multicellular aggregate.

According to a further embodiment of the invention there are provided polymeric particles comprising a polymer, at least one microorganisms in a total concentration of at least $10^8$ CFU/g dry weight and optionally additional carriers and additives, wherein said particles have an average diameter of about 500 µm, or less. In some embodiments, the particles have an average diameter of about 200 µm, or less. In some embodiments, the particles have an average diameter of about 100 µm, or less. In some embodiments, the particles have an average diameter of about 75 µm, or less. In some embodiments, the particles have an average diameter of about 50 µm or less. In some embodiments, the particles have an average diameter of about 25 µm or less. In some embodiments, the particles have an average diameter of about 10 µm or less. In some embodiments, the particles have an average diameter of about 5 µm or less. In some embodiments, the particles have an average diameter of about 1 µm.

In particular, the microorganisms described herein are bacterial and/or fungal cells.

Specifically, the cells of the microorganisms are encapsulated in the polymer. In some embodiments, the cells of the encapsulated microorganisms comprise bacterial cells of one or more Phyla selected from the group consisting of *Firmicutes* and *Proteobacteria*. In some embodiments, the cells of the encapsulated microorganisms comprise bacterial cells of one or more Classes selected from the group consisting of *Betaproteobacteria, Bacilli, Alphaproteobacteria*, and *Gammaproteobacteria*. In some embodiments, the cells of the encapsulated microorganisms comprise bacterial cells of one or more Orders selected from the group consisting of *Aeromonadales, Bacillales, Bifidobacteriales, Burkholderiales, Enterobacterales, Lactobacillales, Neisseriales, Oceanospirillales, Pseudomonadales, Rhizobiales, Rhodospirillales, Sphingomonadales, Streptomycetales*, and *Xanthomonadales*. In some embodiments, the cells of the encapsulated microorganisms comprise bacterial cells of one or more Families selected from the group consisting of *Aspergillaceae, Bacillaceae, Bifidobacteriaceae, Bradyrhizobiacea, Burkholderiaceae, Chromobacteriaceae, Clavicipitaceae, Cordycipitaceae, Coniothyriaceae, Enterobacteriaceae, Erwiniaceae, Hypocreaceae, Lactobacil-* laceae, *Leuconostocaceae, Methylobacteriaceae, Moraxellaceae, Oceanospirillaceae, Oxalobacteraceae, Paenibacillaceae, Pasteuriaceae, Pseudomonadaceae, Rhizobiaceae, Rhodospirillaceae, Sphingomonadaceae, Sclerotiniaceae, Streptococcaceae, Streptomycetaceae, Xanthomona daceae*, and *Yersiniaceae*. In some embodiments, the cells of the encapsulated microorganisms comprise bacterial cells of one or more Genera selected from the group consisting of *Azospirillum, Azotobacter, Bacillus, Bradyrhizobium, Burkholderia, Ensifer, Enterobacter, Herbaspirillum, Lysobacter, Methylobacterium, Paraburkholderia, Pseudomonas, Rhizobium, Serratia, Sphingomonas*, and *Stenotrophomonas*

In some embodiments, the cells of the encapsulated microorganisms comprise fungal cells of the Phylum *Ascomycota*. In some embodiments, the cells of the encapsulated microorganisms comprise fungal cells of one or more Classes selected from the group consisting of *Dothideomycetes, Eurotiomycetes, Leotiomycetes* and *Sordariomycetes*. In some embodiments, the cells of the encapsulated microorganisms comprise fungal cells of one or more Orders selected from the group consisting of *Eurotiales, Helotiales, Hypocreales*, and *Pleosporales*. In some embodiments, the cells of the encapsulated microorganisms comprise fungal cells of one or more Families selected from the group consisting of *Aspergillaceae, Clavicipitaceae, Clavicipitaceae, Coniothyriaceae, Cordycipitaceae, Hypocreaceae*, and *Sclerotiniaceae*. In some embodiments, the cells of the encapsulated microorganisms comprise fungal cells of the Genera selected from the group consisting of *Beauveria, Coniothyrium, Gliocladium, Lecanicillum, Metarhizium, Paecilomyces, Penicillium, Pochonia, Sclerotinia, Trichoderma* and *Verticillium*.

A further embodiment of the invention relates to polymeric particles, wherein the at least two microorganism cells are of different origin, specifically of different strains or species or genus or kingdom.

Specifically, the microorganisms of different origin are either different bacterial species or different fungal species, or a combination thereof.

A further embodiment of the invention relates to polymeric particles as described herein, wherein the microorganisms, specifically bacterial and/or fungal cells are comprised as multicellular aggregates. Specifically, the microorganisms, bacterial and/or fungal cells are comprised as multicellular aggregates thereby embedded in a self-produced extracellular biogenic matrix within the polymeric particle. This multicellular life style supports survival strategies which combine the production of protection molecules and mechanisms as well as the induction of a genetic control system that shifts microorganisms into a dormancy-like state. In one embodiment, the polymeric particles are wet and at least one of the multicellular aggregates is between 14 µm and 43 µm in diameter.

According to a further embodiment of the invention the polymer is a biodegradable polymer. A further embodiment of the invention relates to polymeric particles as described herein, wherein the biodegradable polymer is selected from the group consisting of alginate, agarose, agar, gelatin, polyacrylamide, chitosan, and polyvinyl alcohol.

In some embodiments, the biodegradable polymer is an alginate. In some embodiments, the biodegradable polymer is sodium alginate.

A further embodiment of the invention relates to polymeric particles as described herein, wherein the particles have an average diameter of about 1 to 2,000 µm, or of about 25 to 1,000 µm, or of about 50 to 500 µm, or of about 100 to 250 µm. In some embodiments, particles have an average diameter of about 1 µm, 10 µm, 25 µm, 50 µm, 75 µm, 100 µm, 150 µm, 200 µm, 250 µm, 300 µm, 350 µm, 400 µm, 450 µm, or of about 500 µm.

A further embodiment of the invention relates to polymeric particles as described herein, wherein the viability of the microorganisms is substantially maintained for a storage period of at least 35 weeks at 30° C. and at least 52 weeks at 4° C.

A further embodiment of the invention relates to polymeric particles as described herein, wherein at least 5, 10, 25, 50, 60, 70, 80, 90, or 95% of the microorganism cells are viable after a storage period of 35 weeks at 30° C.

One embodiment of the invention relates to a method for improving the viability of microorganisms during storage and application, comprising the steps of:

a) suspending one or more pre-cultures of microorganism cells in a polymeric solution, b) immobilizing said microorganism cells by dropping the solution of step a) into multivalent ion solution thereby obtaining polymeric particles, c) cultivating the encapsulated microorganisms in said particles for at least 12 h in liquid cultivation media until an increase of the cell density of at least 2 to 10 log is obtained.

One embodiment of the invention relates to a method for improving the viability of microorganisms during storage and application, comprising the steps of:

a) suspending one or more pre-cultures of microorganism cells to a cell density of about $10^0$-$10^8$ CFU/ml in a polymeric substance solution, b) immobilizing said microorganism cells by dropping the solution of step a) into multivalent ion solution thereby obtaining polymeric particles, c) cultivating the encapsulated microorganisms in said particles for at least 12 h in liquid cultivation media until cell density of at least about $10^9$ CFU/g dry weight is obtained.

In one embodiment of the invention, each microorganism is pre-cultured individually up to a cell density of about $10^9$-$10^{10}$ CFU/ml. Depending on the microorganism, the pre-culture is suspended in a polymeric substance solution in the method as described herein to a cell density of about $10^0$-$10^8$ CFU/ml. In particular, the cell density in the suspension of pre-culture and polymeric substance solution is about $10^0$, $10^1$, $10^2$, $10^3$, $10^4$, $10^5$, $10^6$, $10^7$, or $10^8$ CFU/ml. In some embodiments, the cell density in the suspension of pre-culture and polymeric substance solution is about $10^0$ to $10^1$ CFU/ml. In some embodiments, the cell density in the suspension of pre-culture and polymeric substance solution is about $10^1$ to $10^2$ CFU/ml. In some embodiments, the cell density in the suspension of pre-culture and polymeric substance solution is about $10^2$ to $10^3$ CFU/ml. In some embodiments, the cell density in the suspension of pre-culture and polymeric substance solution is about $10^3$ to $10^4$ CFU/ml. In some embodiments, the cell density in the suspension of pre-culture and polymeric substance solution is about $10^4$ to $10^5$ CFU/ml. In some embodiments, the cell density in the suspension of pre-culture and polymeric substance solution is about $10^5$ to $10^6$ CFU/ml. In some embodiments, the cell density in the suspension of pre-culture and polymeric substance solution is about $10^6$ to $10^7$ CFU/ml. In some embodiments, the cell density in the suspension of pre-culture and polymeric substance solution is about $10^7$ to $10^8$ CFU/ml.

In particular, the pre-cultured microorganism is used without further purification. Specifically, for use in step a) the culture medium comprising the pre-cultured microorganism is diluted by suspending in a polymeric substance solution to a cell density of about $10^6$-$10^8$ CFU/ml.

A further embodiment of the invention relates to the method as described herein, wherein the biodegradable polymeric substance is selected from the group consisting of alginate, agarose, agar, gelatin, polyacrylamide, chitosan, and polyvinyl alcohol. In some embodiments, the polymeric substance is alginate. In some embodiments, the polymeric substance is sodium alginate.

A further embodiment of the invention relates to the method as described herein, wherein the polymeric substance solution is solidified by ionotropic gelation.

Specifically, the polymeric substance solution is gelled following addition of a multivalent ion solution.

In one embodiment of the invention, the multivalent ion solution is a $CaCl_2$) solution.

In one embodiment of the invention, the at least one microorganisms are bacterial and/or fungal cells.

In some embodiments, the at least one microorganisms are bacterial cells selected from the group consisting of *Azospirillum, Bacillus, Enterobacter, Stenotrophomonas, Rhizobium, Bradyrhizobium, Ensifer, Methylobacterium, Serratia, Lysobacter, Firmicutes, Azotobacter, Sphingomonas* and *Pseudomonas*, and the fungal cells are *Trichoderma* cells.

A further embodiment of the invention relates to the method as described herein, wherein at least two microorganisms of different origin are applied. Therefore, in one embodiment of the invention, bacterial cells from two, three, four, five, six, or more different species may be employed.

In an alternative embodiment of the invention, fungal cells from two, three, four, five, six, or more different species may be employed.

Alternatively, bacterial cells from one, two, three, four, five, six, or more different species may be employed together with fungal cells from one, two, three, four, five, six, or more different species. Thus, one, two, three, four, five, or more distinct individual organisms or distinct members of different genetic derivation or taxa are encapsulated in the polymeric particle.

A further embodiment of the invention relates to the method as described herein, wherein the encapsulated microorganisms are cultivated in in a fluidized-bed fermenter-like system. Specifically, the encapsulated microorganisms are in-bead cultivated until a cell density of about $10^9$ to $10^{12}$ CFU/g dry weight is reached. According to a further embodiment of the invention the encapsulated microorganisms are in-bead cultivated until a cell density of about $10^{10}$, $10^{11}$ or $10^{12}$ CFU/g dry weight is reached.

A further embodiment of the invention relates to the method as described herein, wherein the encapsulated microorganisms are cultivated at temperatures of 20° C.–30° C. for at least 24 to 72 hours. In some embodiments, the encapsulated microorganisms are cultivated at temperatures of 21-24° C. In some embodiments, the encapsulated microorganisms are cultivated for at least 36 hours. In some embodiments, the encapsulated microorganisms are cultivated for at least 48 hours. In some embodiments, the encapsulated microorganisms are cultivated for about 36 to 48 hours. In some embodiments, the encapsulated microorganisms are cultivated for about 48 to 72 hours.

In one embodiment of the invention, the in-bead cultivation is carried out with polymeric particles, wherein in said particles comprising microbial cells of one, two, three, four, five, six, or more distinct genetic origins have been encapsulated. The in-bead cultivation may be carried out with polymeric particles containing encapsulated microbial cells that share a common genetic derivation, e.g., one or more propagules of a single microbe, or polymeric particles which contain encapsulated microbial cells that have a divergent genetic derivation or taxonomic relationship. As a non-limiting example, a polymeric particle may contain one or more bacterial cell colonies having shared genetic derivation, a polymeric particle may contain one or more bacterial or fungal cell colonies having divergent genetic derivation (for example, one or more distinct species, genera, class, family, order or phylum).

A further embodiment of the invention relates to the method as described herein, wherein the encapsulated microorganisms in the polymeric particles possess a sessile lifestyle and establish dense multicellular aggregates due to the cultivation step. In particular, the microorganisms in the polymeric particles are embedded in a self-produced extracellular matrix.

The polymeric particles may be dried at ambient temperatures, preferably air dried. For example, the polymeric particles are dried in a static bed or drum dryer at a temperature of about 20 to 35° C., preferably at a temperature of about 25 to 30° C. The average drying time is of about 18 to 36 h, preferably of about 24 to 30 h. Thus, a further embodiment of the invention relates to the method as described herein, wherein the polymeric particles are dried, preferably air dried.

The dry polymeric particles have a moisture content of less than or equal to 15.0% by weight, based on the total weight of said polymeric particles. According to a further embodiment of the invention the dry polymeric particles have a moisture content of less than or equal to 20.0% by weight, or less than or equal to 10.0% by weight, based on the total weight of said polymeric particles.

The polymeric particles are advantageous for applications in the field of agriculture, food and/or feed industry, cosmetics industry and/or pharmaceutical industry.

A further embodiment of the invention relates to the use of the polymeric particles as described herein for targeted agricultural delivery, plant protection, growth promotion, and/or fertilization, biological remediation of soil and/or water, as food additives, feed additives, or for medical purposes.

In particular, the polymeric particles may be used in agricultural industry, e.g. for producing biological agents for plant health protection, plant growth promotion, biofertilization and a-biotic stress protection.

According to an aspect of some embodiments of the present invention there is provided a use of the polymeric particle as a medicament for treating a condition that is treatable by the encapsulated microbial cells.

BRIEF DESCRIPTION OF DRAWINGS

FIG. 12B Viability of a second *Pseudomonas* species ("strain B") after drying, after short term storage at 30° C., and after long term storage at 30° C. when formulated by the BFC technology using differing cultivation media (LB=Luria-Bertani broth, TSB=tryptic soy broth).

FIG. 17 Morphology of BFC encapsulated *Stenotrophomonas rhizophila* SPA-P69 prepared using differing pre-culture inoculation densities ($10^5$ CFU/ml, $10^6$ CFU/ml, $10^7$ CFU/ml) was assessed after 48 hours of in-bead cultivation. Lower pre-culture inoculation densities produce distinct (well separated from other colonies) and dense colonies. All beads pictured were produced using an alginate concentration of 1.5%, $CaCl_2$) concentration of 150 mM, nozzle diameter of 100 μm, the strain was grown in 0.5× Nutrient Broth II (SIFIN, Germany) and cultivated at 22° C. in-bead for 48 hours.

DESCRIPTION OF EMBODIMENTS

The application of microorganisms for any purpose at commercial scale strongly depends on the reliability of the microbial preparation. Particularly, when microbial agents are intended to be applied as additive e.g. in coatings for seed treatment processes, the requirements for the formulation are high. Apart from the general desiccation stress in dry formulations, microorganisms are additionally exposed to physical, thermal as well as to detrimental chemicals, e.g., pesticidal agents. To circumvent said problems with the stability of microbial strains, mostly Gram-positive bacteria with spore-forming ability are currently used.

Conventionally, microbial agents are produced by cultivating microbial cells in liquid media to a certain cell number, harvesting, mixing with appropriate carriers and drying. The encapsulation of cells in biopolymers (e.g., sodium alginate) prior to drying is also commonly used (Bashan et al., 1986). To evoke longevity of the formulated microbes, several strain-specific protective compounds are applied. In case of multi-strain preparations, the single strains are usually cultivated individually before they are formulated together. Sensitive Gram-negative bacteria possess a great potential for biological plant protection. Despite much attention on the stabilization of microorganisms in formulations suitable for large scale applications, no appropriate solutions are available.

The invention discloses methods for formulation and fermentation to improve the viability of microbial cells during storage and application. In some embodiments, methods described herein comprise reducing pre-culture inoculation densities. In some embodiments, methods described herein comprise a step of in-bead cultivation of encapsulated microbial cells. Methods disclosed herein are suitable for all microorganisms including those for agricultural purposes, for food and feed purposes, as well as for medical purposes.

As used herein, the terms "microorganism" or "microbial" cover prokaryotic and eukaryotic, unicellular or multicellular organisms, and combinations thereof, which can be propagated and manipulated in a laboratory. In some embodiments, a microorganism includes, but is not limited to, eubacteria and archaea, protozoa, fungi and algae. In the present disclosure, the term microorganism typically denotes a live microorganism, e.g., capable of propagation, e.g., capable of having metabolic activity.

As used herein, the terms "bacteria" and "eubacteria" are used in reference to unicellular organisms, including recombinant organisms, lacking that lack a nucleus and other membrane bound organelles. Bacteria can function and reproduce as individual cells or multicellular aggregates.

As used herein "archaea" are single-cell organisms that lack nuclei and have archaeal membranes, specifically made of ether lipids.

As used herein, "fungi" is used in reference to eukaryotic organisms such as the molds and yeasts, including dimorphic fungi, fungi found in soil, recombinant fungi and any fungi capable of growing on plants.

As used herein, the term "strain" refers in general to a distinct genotype of organisms of the same species. More particularly, the term "strain" refers to members of a microbial species, wherein such members, i.e., strains, have different genotypes and/or phenotypes. Herein, the term "genotype" encompasses both the genomic and the recombinant DNA content of a microorganism and the microorganism's proteomic and/or metabolomic profile and post translational modifications thereof. Herein, the term "phenotype" refers to observable physical characteristics dependent upon the genetic constitution of a microorganism. As one skilled in the art would recognize, microbial strains are thus composed of individual microbial cells having a common genotype and/or phenotype. Further, individual microbial cells may have specific characteristics (e.g., a specific rep-PCR pattern) which may identify them as belonging to their particular strain. A microbial strain can comprise one or more isolates of a microorganism.

As used herein, the term "reference method" refers to an alternate method of microbial stabilization other than the inventive BFC technology described herein, e.g., an alternate method that does not include stabilizing microorganisms by shifting them into a dormancy-like state through targeted in-bead cultivation). A "reference composition" refers to a composition generated from an identical pre-culture material by application of a differing stabilization methodology. By way of a non-limiting example, stability of a microbial cells encapsulated in polymeric particles using a method of the present invention (e.g., stabilizing microorganisms by shifting them into a dormancy-like state through targeted in-bead cultivation) is compared to a reference composition wherein the reference composition was generated using a different method, such that differences in stability of the end-product microbial cells are attributable to differences in the method of production.

As used herein, the term "kingdom" refers to the general taxonomic category, e.g. fungi and bacteria.

As used herein, "CFU" refers to a colony forming unit.

As used herein, the term "inoculum" is intended to mean any form of microbial cells, or spores, which is capable of propagating in a culture medium.

Culture medium as used herein is defined as a mixture which supports the growth of microbial cells, such as disclosed microorganism, said mixture may contain for example ingredients such as peptone, soy peptone, molasses, potato starch, yeast extract powder, glucose, mannitol, skim milk or combinations thereof. Culture medium can be solid culture medium or liquid medium.

According to the invention there are provided microorganisms, such as for example, but not limited to, biotechnologically, agriculturally or medically useful microorganisms, microorganisms useful for food and feed purposes, which are encapsulated in biodegradable polymers.

Microorganisms of the invention can either be of natural origin or produced by recombinant methods.

As used herein, the term "biodegradable polymer" refers to polymer-based matrices that show at least some biodegradability. Non-limiting examples of suitable biodegradable polymers include collagen, gelatin, alginate, polycaprolactone, and poly lactic-co-glycolic acid (PLGA).

Figure 1A:
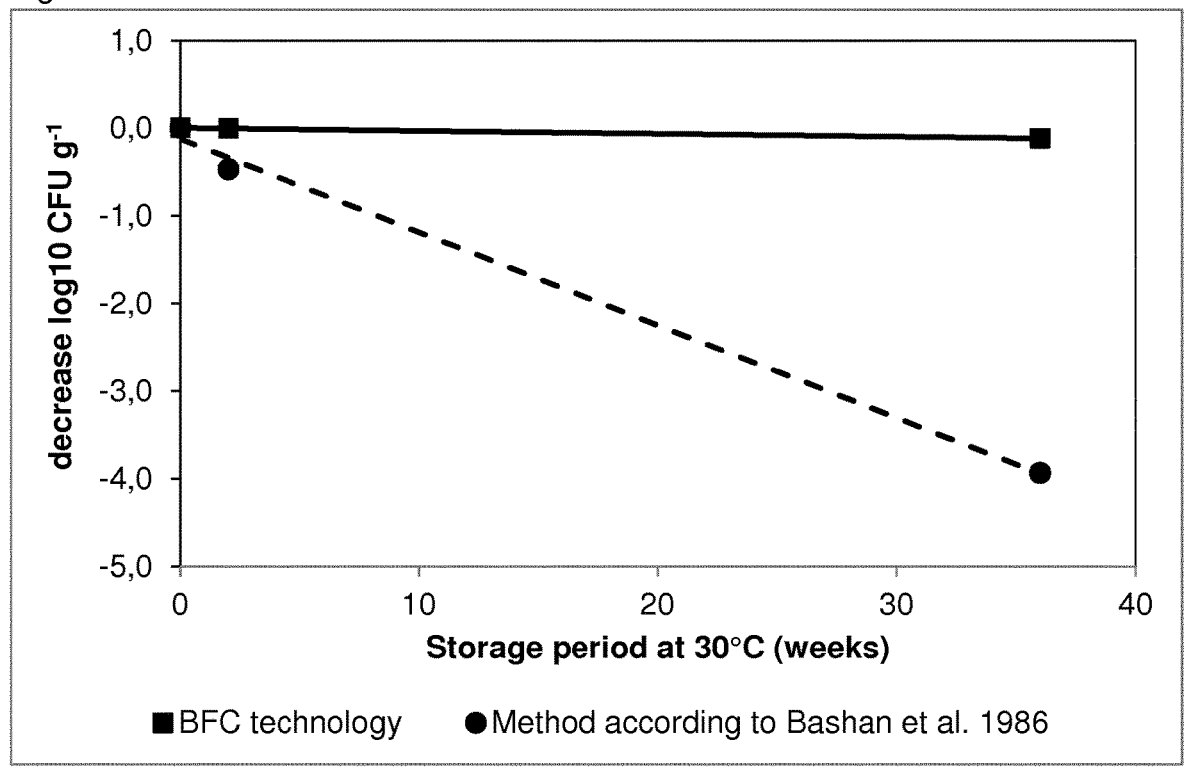
FIG. 1A: Viability of *Stenotrophomonas rhizophlla* cells formulated by the encapsulation method according to Bashan et al 1986 (circle) and by the inventive bacterial fungal conservation (BFC) technology (square) at 30° C. over a period of 36 weeks.

In some embodiments, the biodegradable polymer may be an unsaturated biodegradable polymer (i.e. a biodegradable polymer containing at least one unsaturated carbon-carbon bond, such as a double or a triple bond). Such unsaturated polymers may be cross-linkable in situ. Non-limiting examples of unsaturated biodegradable polymers include poly-propylene fumarate (PPF), poly(ε-caprolactone-fumarate), and mixtures and co-polymers thereof.

In various embodiments, the polymer particles of the present invention may be hydrogel particles (e.g., alginates, fibrins, and gelatins), natural or synthetic biodegradable particles (e.g., particles derived from or coated with poly lactic-co-glycolic acid (PLGA)), biodegradable porous particles (e.g., silicon porous particles), and biocompatible vesicles (e.g., liposomes and/or micelles).

Particularly suitable biodegradable polymers for agriculturally suitable microorganisms are, amongst others, agarose, alginates, agar, gelatin, polyacrylamide, kappa-carrageenan, furcellaran, 2-methyl-5-vinyl-pyridine-methylacrylate, ethyl succinylated cellulose, chitosan, polyvinyl alcohol, polygammaglutamic acid, ethyl cellulose and other biodegradable polymers known to one of skill in the art.

Alginate is a naturally occurring anionic polymer typically obtained from brown seaweed. Due to its biocompatibility, low toxicity, relatively low cost, and mild gelation by addition of divalent cations such as $Ca^{2+}$ it has been extensively used for many biomedical applications. Commercially available alginate is typically extracted from brown algae (*Phaeophyceae*). Alginate with more defined chemical structures and physical properties can be obtained from seaweed-derived alginate. Bacterial alginate can be produced from *Azotobacter* and *Pseudomonas*.

Alginate is a mix-polysaccharide composed of D-mannuronic acid (M) L-guluronic acid (G). The main alginate series include sodium alginate, potassium alginate, calcium alginate, ammonium alginate etc. In some embodiments sodium alginate is used.

For medical purposes, the biodegradable polymer is selected from materials which are considered safe to the human body and degraded in the body for a certain period of time. Examples of biodegradable polymers considered safe include albumin, collagen, gelatin, fibrinogen, casein, fibrin, hemoglobin, transferrin, chitin, chitosan, hyaluronic acid, heparin, chondroitin, keratin sulfate, alginate, starch, dextrin, dextran, polylactic acid, polyglycolic acid, lactic acid-glycolic acid copolymer, polyhydroxybutyric acid, polycaprolactone, polyanhydride and polyalkylcyanoacrylate.

Individual polymeric particles may be produced when specified hydrogel polymers are complexed in solutions of biologically active substrates. An alginate solution, for example, will form a gel when a complexing agent is added. Calcium chloride ($CaCl_2$) is generally used; however, lanthanum chloride, ferric chloride, cobaltous chloride and calcium hydroxide are also acceptable.

In order to obtain alginate beads which include microbial cells, the microbial cells are dispersed in a sodium alginate solution. The obtained solution is dropped into a crosslinking solution containing divalent cations, e.g. $Ca^{2+}$. Solidification of the droplets starts immediately on the droplet surface by ionotropic gelation. $Ca^{2+}$ reacts with the negatively charged polymer chains to form a three-dimensional rigid structure.

In one embodiment of the invention, the microbial cells are individually pre-cultured according to conventional methods up to a cell density of about $10^9$ to $10^{10}$ CFU/ml.

The individual pre-cultures are suspended in a biodegradable polymer solution up to a cell density of about $10^6$ to $10^8$ CFU/ml. Thus, in one embodiment two pre-cultures of microorganism of different origin are suspended in the biodegradable polymer solution, e.g., in an alginate solution. In some embodiments, 3, 4, 5, 6, or more microorganism of different origin are suspended in an alginate solution. Optionally, the polymer solution contains additionally carriers and/or additives.

If 2 microorganisms of different origin are provided, they may be present in a ratio of 1:5 to 5:1, or 1:2 to 2:1, or 1:1. If 3 microorganisms of different origin are provided, they may be present in a ratio of 1:1:5 to 5:5:1, or 1:2:2 to 2:1:1, or 1:1:1, etc.

Various additives such as adherents, dispersants, surfactants, and nutrient and buffer ingredients, can also be included. Trace nutrients such as salts of iron, manganese, boron, copper, cobalt, molybdenum, or zinc may be added. Other conventional additives including, but not limited to, coating agents, wetting agents, buffering agents, and polysaccharides may be added. At least one agriculturally acceptable carrier can be added to the formulation such as water, solids or dry powders. The dry powders can be derived from a variety of materials such as calcium carbonate, gypsum, fluency agent, vermiculite, talc, clay, humus, activated charcoal, and various phosphorous compounds. These additives are generally added to the suspension in an amount of 0.001% to 10% of the polymeric substance solution.

Suitable carriers include, but are not limited to mineral earths such as silica, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silica and synthetic calcium silicates, or compositions of these.

Bead formation is performed for example by dropping the suspension, which comprises the pre-cultured microbial cells and a polymeric substance, into a multivalent ion solution bath using a vibrating nozzle. In some embodiments, the nozzle diameter may be in the range of about 1 μm to 500 μm. In some embodiments the nozzle diameter is within the range of 70 to 100 μm. In some embodiments the nozzle diameter is about 75 μm. In some embodiments the nozzle diameter about 100 μm. In some embodiments the nozzle diameter is about 200 μm and the obtained wet beads have an average diameter of about 100 to 500 μm.

Bead diameters of less than 500 μm and preferably less than 100 μm may be advantageous because they allow optimal growth of bacteria across the entire bead and, thus, use full capacity of bead volume to achieve a maximum of bacterial load. A prerequisite for uniform growth is uniform allocation of nutrients and oxygen. The polymer matrix acts as a diffusion barrier limiting the transfer of compounds within the beads. It can be assumed that the concentration of nutrients and oxygen in particular, decreases from the outer layer to the bead core. The larger the diameter of the beads the lower the concentration of growth compounds in the inner parts, e.g., in the core of the beads. Insufficient availability of nutrients would impair bacterial growth and cause barren zones. In consequence, the larger the diameter of the beads the lower the volumes in which bacteria are able to multiply in relation to the total volume of the bead. The achievable cell number per gram polymeric particles is lower in beads with an average diameter greater than 500 µm, compared to beads with an average diameter less than 500 µm.

After a washing step, the obtained beads are transferred to a system for cultivation of the encapsulated microorganisms. The incubation time is of about 12 to 120 hours, preferably of about 48 hours. Suitable systems for in-bead cultivation of encapsulated microorganisms are, for example: fluidized bed reactors. Due to process-specific cultivation, the encapsulated microorganisms' stability is enhanced via stress adaptation. The growth rates and maximal cell counts resemble those from non-encapsulated cultures but can be slightly higher. Additionally, microbial cells that are allowed to multiply in a solid matrix format may induce biofilm-like substances and demonstrate improved shelf-life of the particle as described herein.

Batch fermentation processes represent closed systems, in which bacterial cultures pass through different growth phases. In the moment, the conditions become unfavorable e.g., nutrients are exhausted and waste products are enriched, bacteria populations enter the stationary phase characterized by stable cell numbers over a certain period of time. Such conditions induce a general stress-response in bacterial cells and an adaptation of their metabolic activity in preparation of a starvation period. Stress-mediated response involves changes in cell membrane structure, formation of biofilms and synthesis of compounds protecting essential molecules such as proteins and DNA. Stress-adapted cells possess a higher tolerance towards adverse conditions and a higher survivability.

Thus, the duration of the cultivation process of bacteria within the beads is not determined by the end of the multiplication (begin of stationary phase) with the aim to obtain the maximum of cell numbers. As described herein, the inventors made the novel and unexpected discovery that by prolonging in-bead cultivation the stationary phase is subsequently maintained enabling bacteria to activate mechanisms and to adapt to stress conditions, and to exhibit the so-called stationary phase phenotype.

The time a culture needs to accomplish stress-adaptation and the underlying mechanisms are strain-specific, they have to be adapted to the respective microbial strains. For the majority of microorganisms a time period between 48 and 72 hours is sufficient for in-bead cultivation.

A biofilm is a well-organized community of microorganisms that adheres to surfaces and is embedded in a matrix of extracellular polymeric substances (EPSs). EPSs are a complex mixture of high-molecular-mass polymers (>10,000 Da) generated by the bacterial cells, cell lysis and hydrolysis products, and organic matter adsorbed from the substrate. EPSs are involved in the establishment of stable arrangements of microorganisms in biofilms. Biofilm formation is one of the mechanisms bacteria use to survive in adverse environments. Bacteria living in a biofilm usually have significantly different properties from free-floating (planktonic) bacteria of the same species, as the dense and protected environment within the biofilm allows them to cooperate and interact in various ways. One benefit of this environment is increased resistance to detergents and antibiotics, as the dense extracellular matrix and the outer layer of cells protect the interior of the community.

Figure 5:
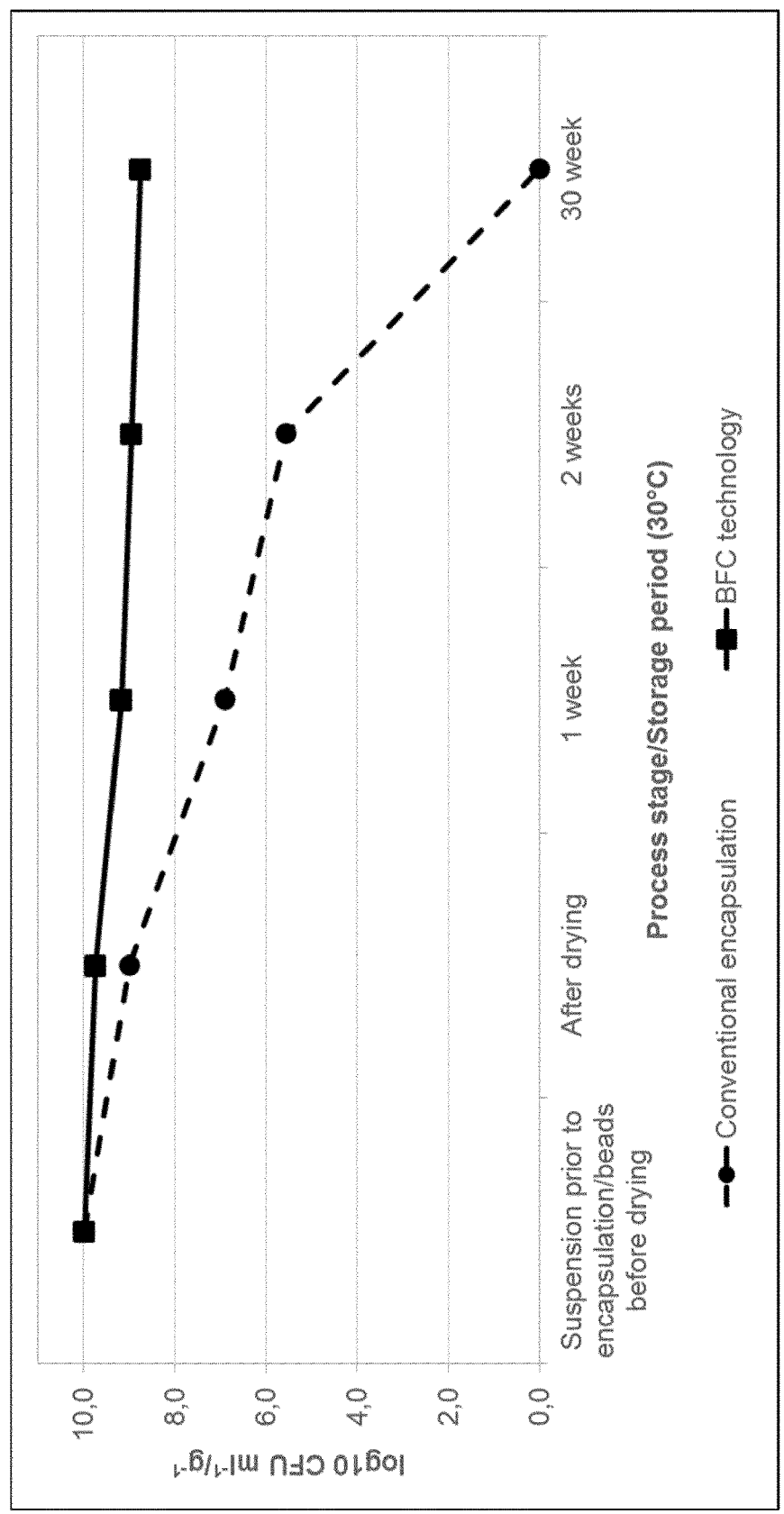
FIG. 5 Viability of *Rhizobium fredii* DSM 5851 cells formulated by encapsulation of planktonically grown cells ("conventional encapsulation") (circle) and by the inventive BFC technology (square) at 30° C. over a period of 30 weeks. For each encapsulation methodology the beads had a diameter of approximately 200 μm after drying, and between 480-600 μm when wet (prior to drying).
Figure 6:
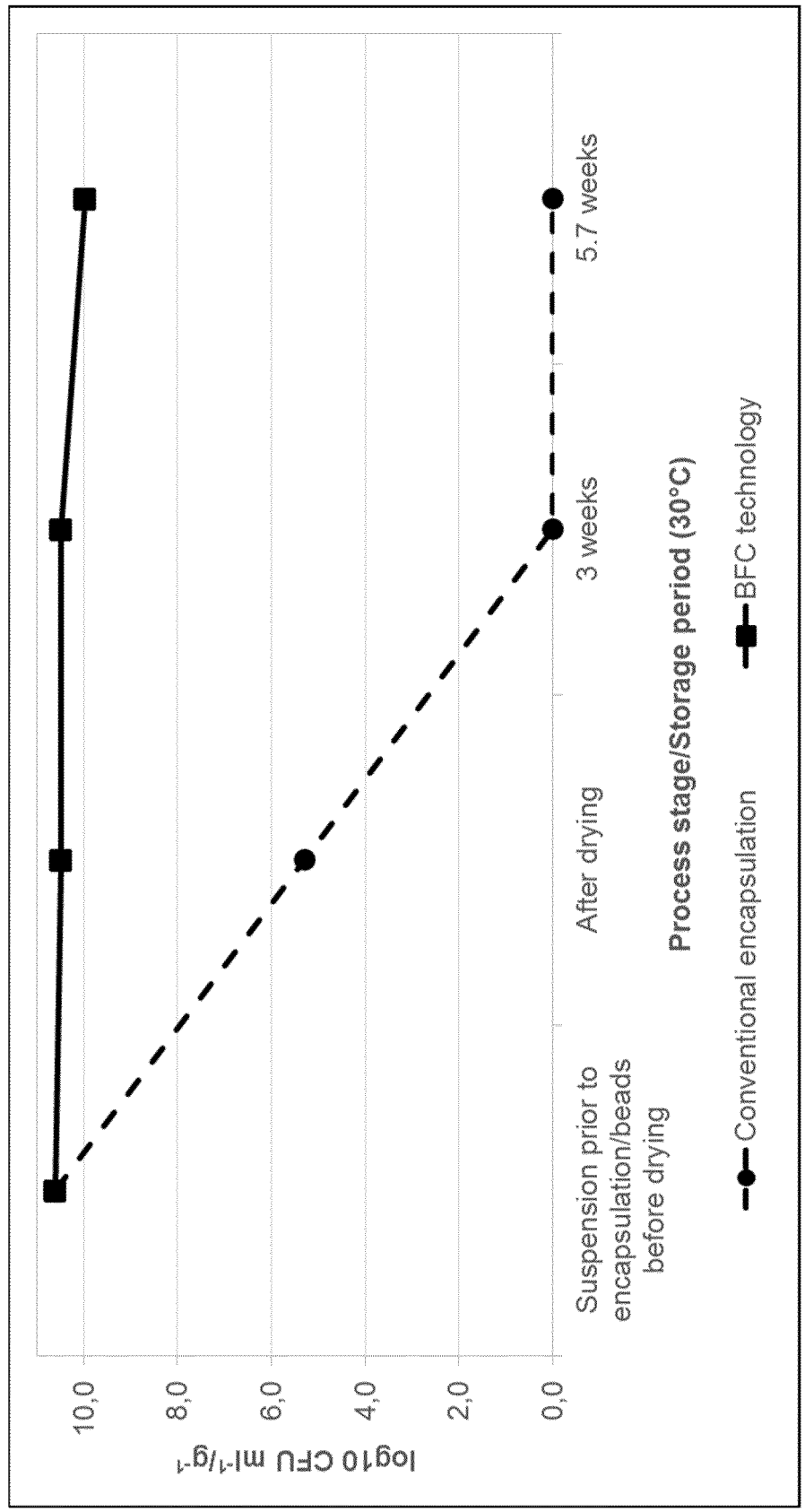
FIG. 6 Viability of *Enterobacter cowanii* cells formulated by encapsulation of planktonically grown cells ("conventional encapsulation") (circle) and by the inventive BFC technology at 30° C. over a period of 40 days. For each encapsulation methodology the beads had a diameter of approximately 200 μm after drying, and between 480-600 μm when wet (prior to drying).
Figure 7:
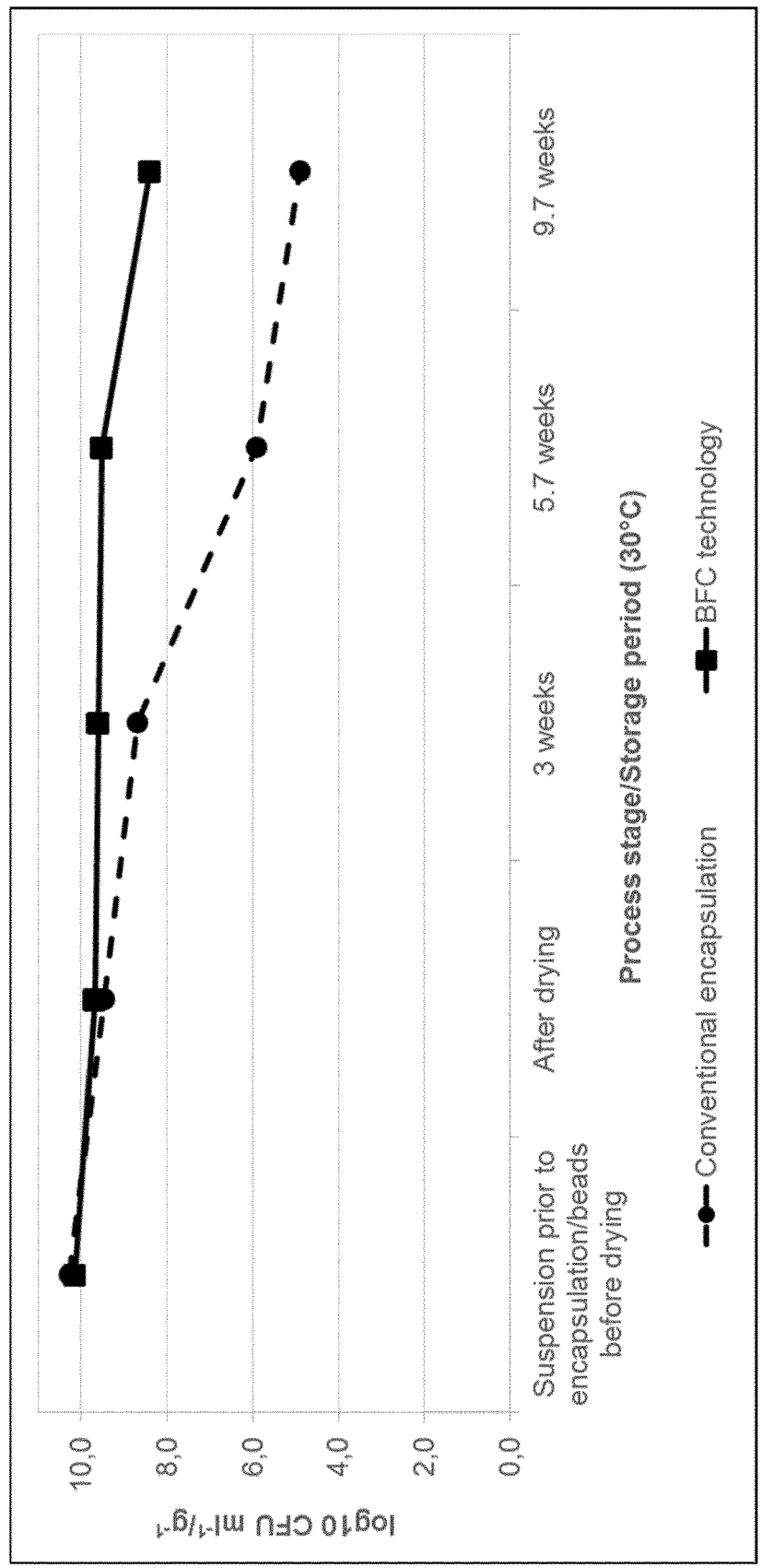
FIG. 7 Viability of *Sphingomonas sanguinis* cells formulated by encapsulation of planktonically grown cells ("conventional encapsulation") (circle) and by the inventive BFC technology at 30° C. over a period of 68 days. For each encapsulation methodology the beads had a diameter of approximately 200 μm after drying, and between 480-600 μm when wet (prior to drying).
Figure 8A:
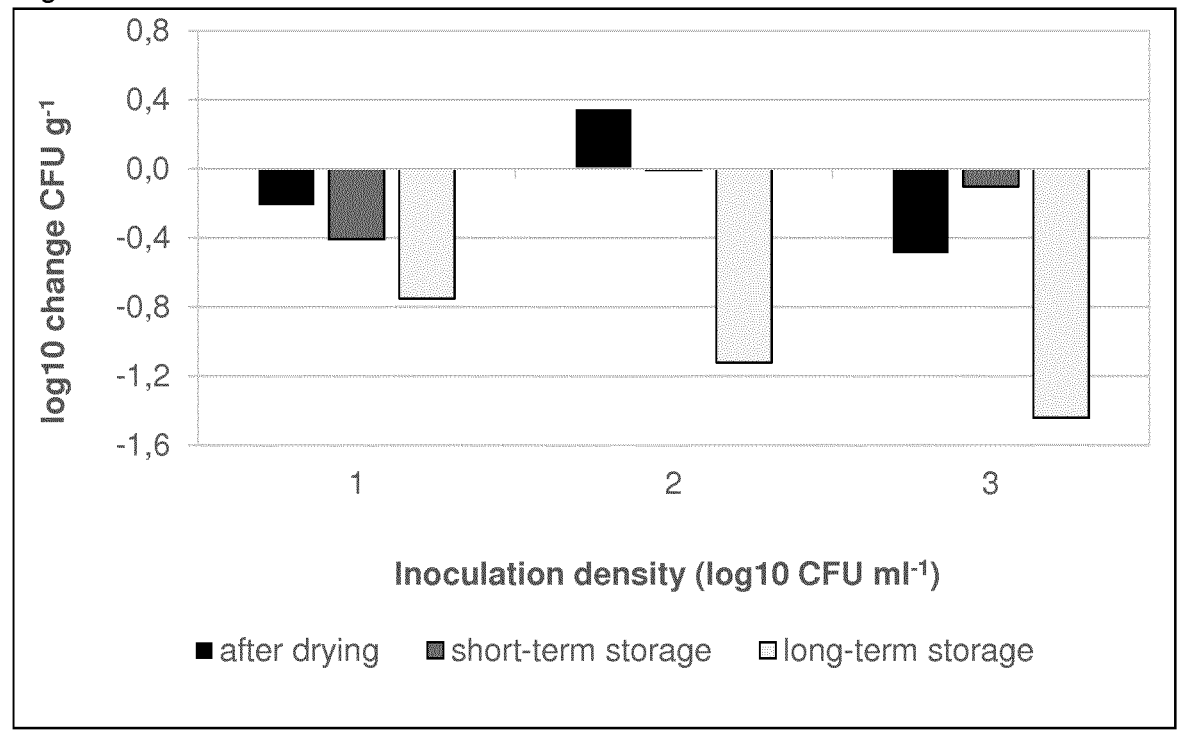
FIG. 8A Viability of a first *Pseudomonas* species ("strain A") when formulated by the BFC technology using differing pre-culture inoculation densities ($10^5$ CFU/mL, $10^6$ CFU/mL, $10^7$ CFU/mL) after drying, after short term storage at 30° C., and after long term storage at 30° C.
Figure 8B:
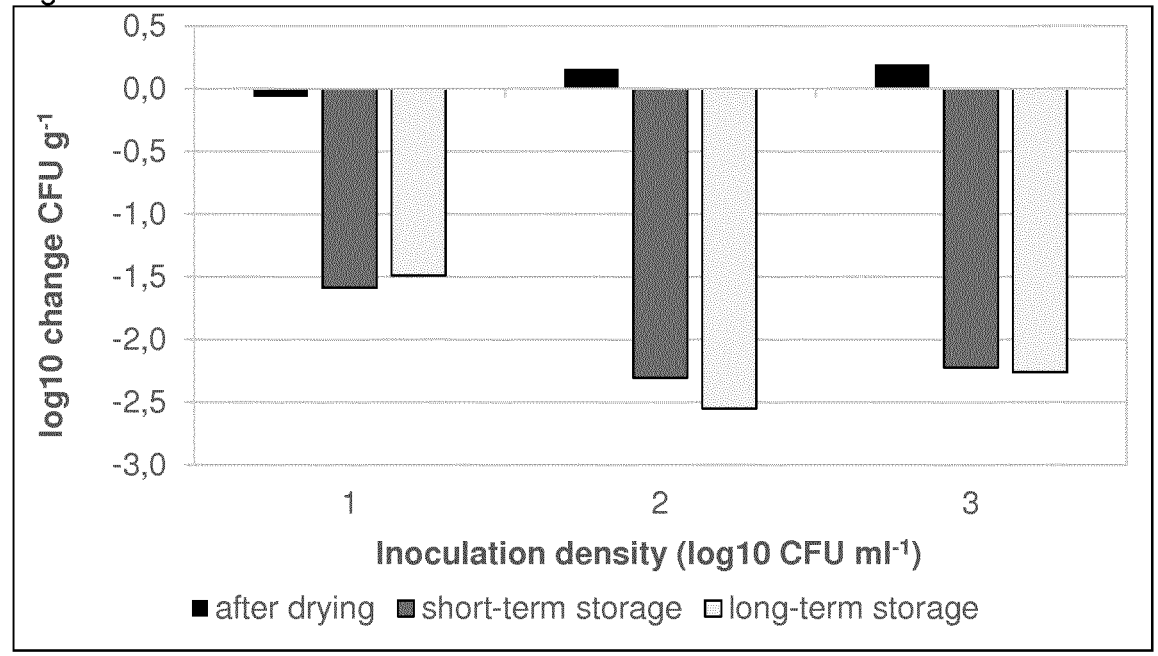
FIG. 8B Viability of a second *Pseudomonas* species ("strain B") when formulated by the BFC technology using differing pre-culture inoculation densities ($10^5$ CFU/mL, $10^6$ CFU/mL, $10^7$ CFU/mL) after drying, after short term storage at 30° C., and after long term storage at 30° C.
Figure 9:
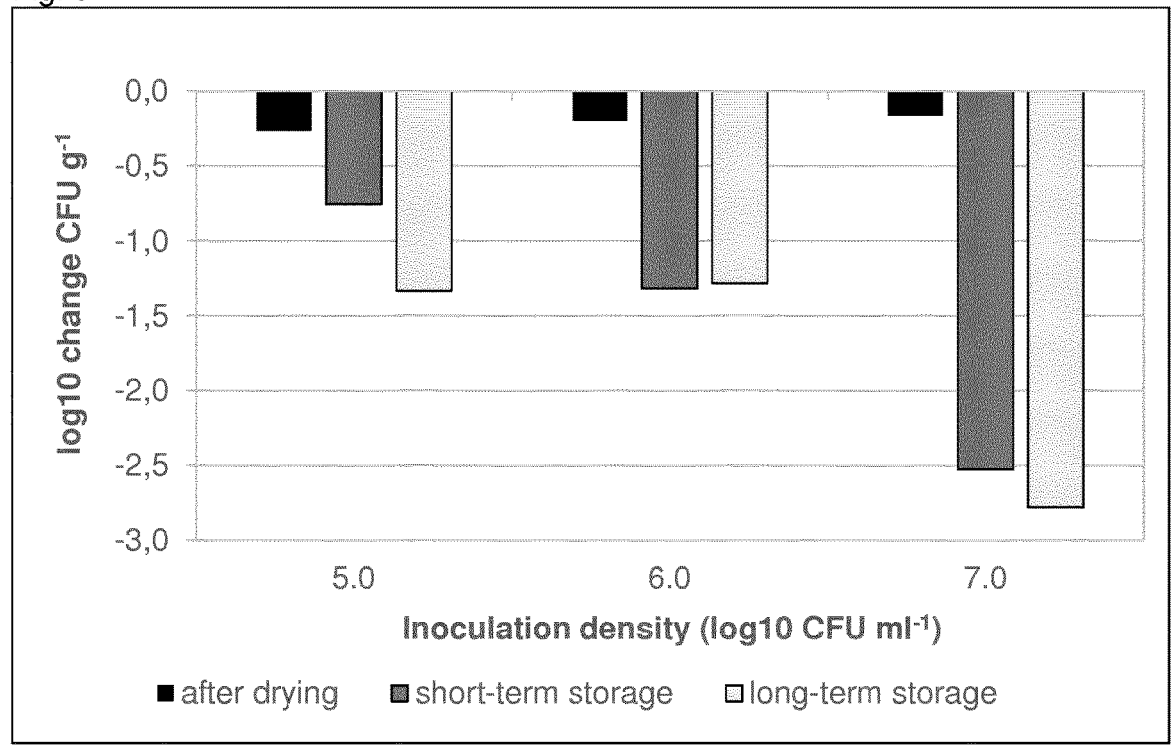
FIG. 9 Viability of a *Serratia* species when formulated by the BFC technology using differing pre-culture inoculation densities ($10^5$ CFU/mL, $10^6$ CFU/mL, $10^7$ CFU/mL) after drying, after short term storage at 30° C., and after long term storage at 30° C.
Figure 10:
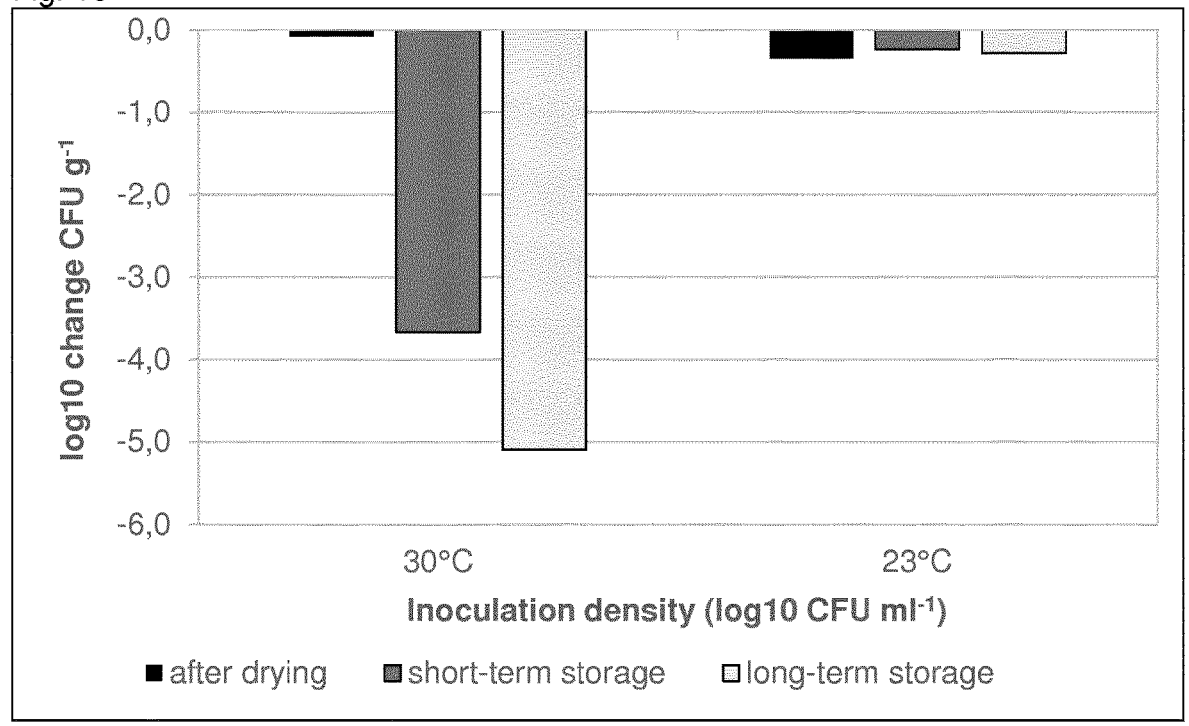
FIG. 10 Viability of *Stenotrophomonas rhizophila* SPA-P69 after drying, after short term storage at 30° C., and after long term storage at 30° C. when formulated by the BFC technology using differing cultivation temperatures (30° C. and 23° C.).
Figure 11:
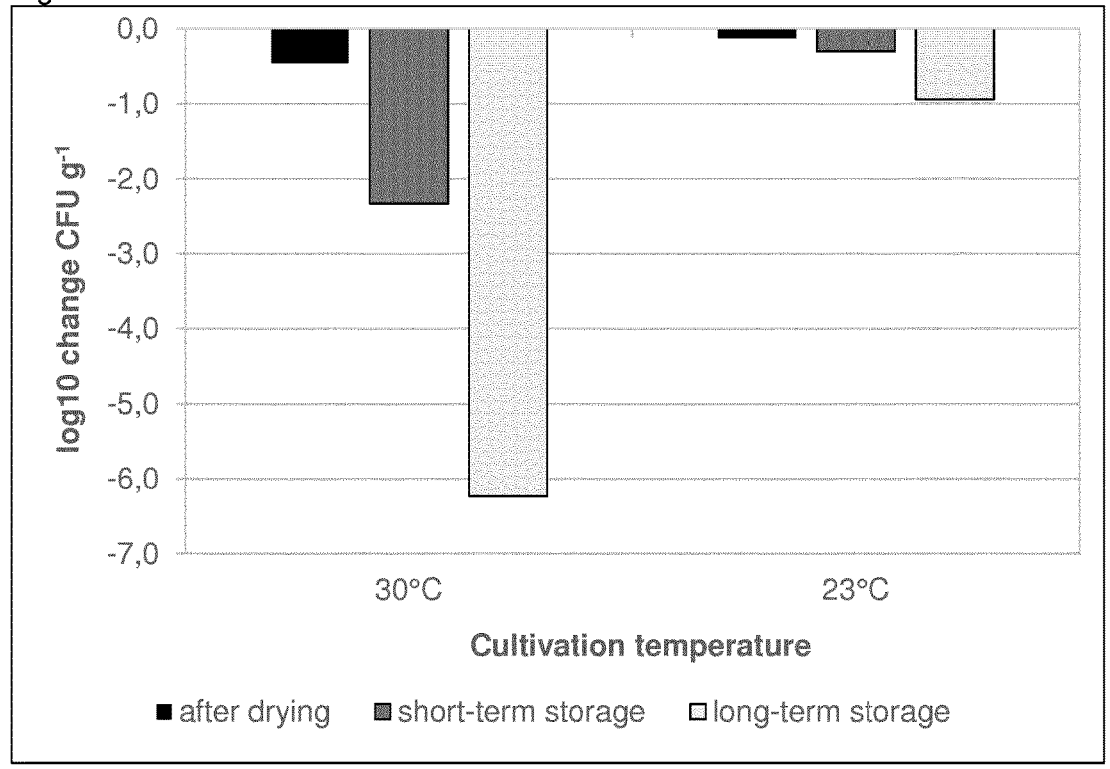
FIG. 11 Viability of *Rhizobium fredii* DSM 5851 after drying, after short term storage at 30° C., and after long term storage at 30° C. when formulated by the BFC technology using differing cultivation temperatures (30° C. and 23° C.).
Figure 12A:
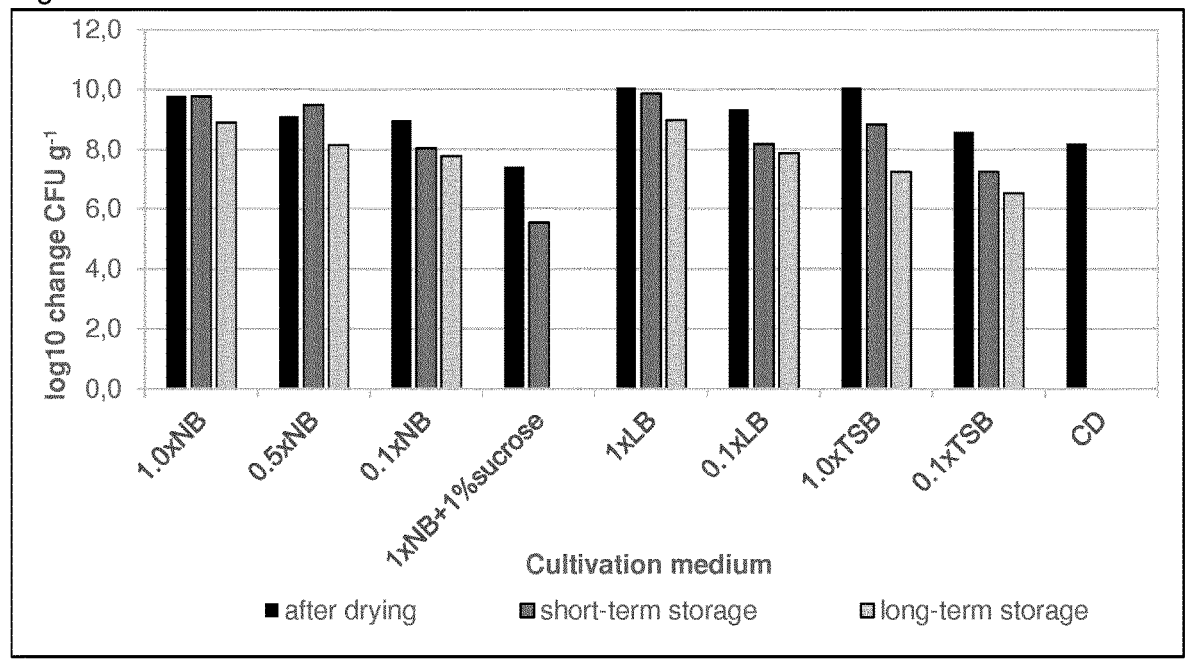
FIG. 12A Viability of a first *Pseudomonas* species ("strain A") after drying, after short term storage at 30° C., and after long term storage at 30° C. when formulated by the BFC technology using differing cultivation media (LB=Luria-Bertani broth, TSB=tryptic soy broth, CD=Czapek dox broth).
Figure 13:
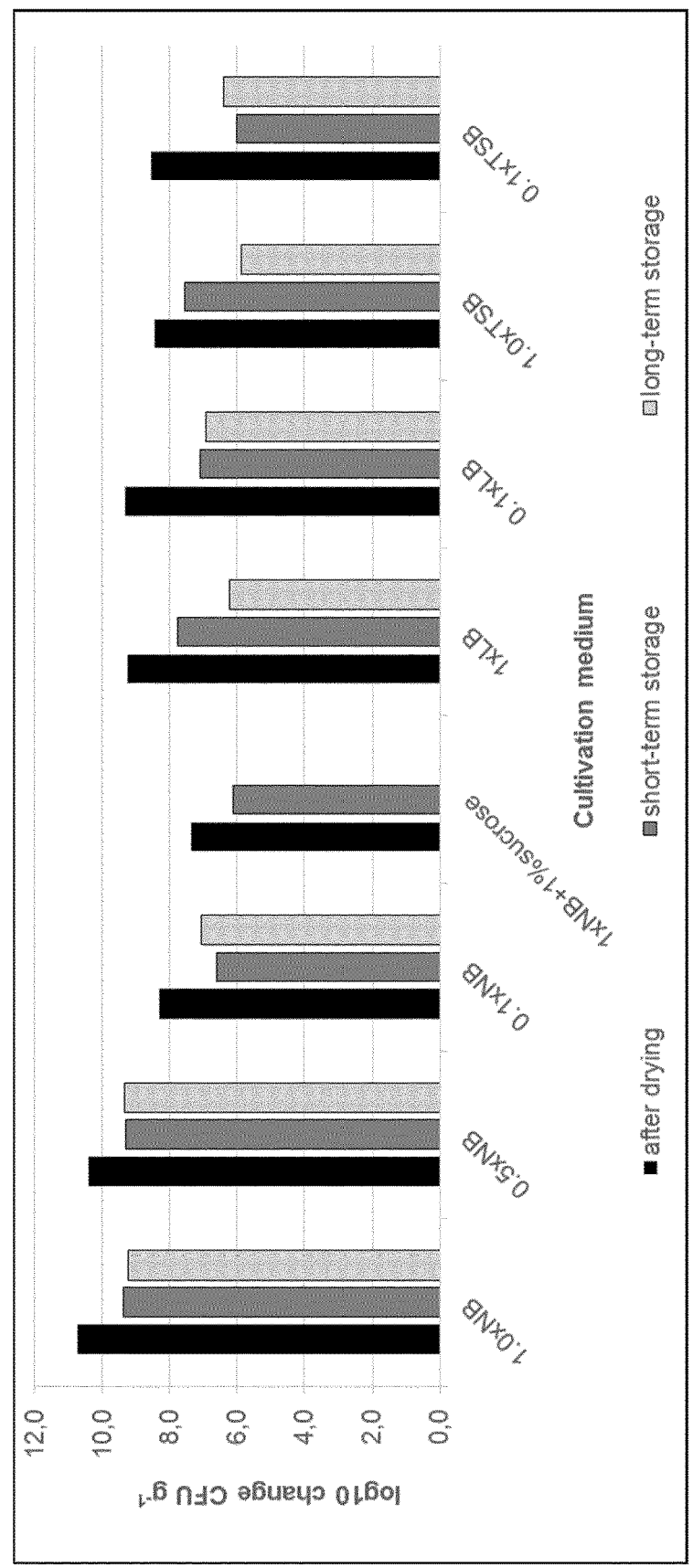
FIG. 13 Viability of a *Serratia* species after drying, after short term storage at 30° C., and after long term storage at 30° C. when formulated by the BFC technology using differing cultivation media (LB=Luria-Bertani broth, TSB=tryptic soy broth).

Bashan (1986) discloses the immobilization and multiplication of *Azospirillum brasilence* Cd in alginate beads. In Bashan (1986), *A. brasilence* was pre-cultured in nutrient broth to a final concentration of $10^9$ CFU/ml, then encapsulated in alginate beads. The beads were washed and incubated for 24 to 48 h in fresh nutrient broth medium to allow multiplication inside the beads. The beads were either kept in hermetically sealed flasks or were lyophilized and were stable for about 12 weeks (Bashan (1986), page 1095, FIG. 5B). However, if the particles were air dried, only a very small number of bacteria survive (Bashan (1986), page 1095, FIG. 5A).

In contrast, the beads obtained according to the present invention exhibit significant post-drying stability and may be dried at ambient temperatures and still are stable for at least 35 weeks at 30° C. as shown in FIG. 1A. For example, the beads are dried at 20 to 35° C. in a static bed or drum dryer, or at 25 to 30° C. The appropriate drying time is of about 15 to 48 h, or 22 to 36 h, or 24 to 30 h.

In contrast to Bashan (1986), the polymeric particles according to the invention can be stored at room temperature for several weeks without substantially reducing the number of viable microorganism cells.

A further embodiment of the invention relates to the polymeric particles comprising at least one microorganism, wherein at least 70% of the microbial cells in the beads are viable upon storage of at least 35 weeks at 30° C. In some embodiments at least 75%, 80%, 85%, 90%, or 95% of the microbial cells in the beads are viable upon storage of at least 35 weeks. In some embodiments at least 75%, 80%, 85%, 90%, or 95% of the microbial cells in the beads are viable upon storage of at least 35, 40, 45, 50 or 52 weeks at 30° C.

A further embodiment of the invention relates to the polymeric particles comprising at least two microorganisms of different origin, wherein at least 70% of the microbial cells in the beads are viable upon storage of at least 35 weeks at 30° C. In some embodiments at least 75%, 80%, 85%, 90%, or 95% of the microbial cells in the beads are viable upon storage of at least 35 weeks at 30° C. In some embodiments at least 75%, 80%, 85%, 90%, or 95% of the microbial cells in the beads are viable upon storage of at least 35, 40, 45, 50 or 52 weeks at 30° C.

In various embodiments the bacteria or fungi are agriculturally and/or horticulturally useful, for example, the bacteria are pesticidal and/or insecticidal, and/or supports plant growth and/or development, or any combination thereof.

In various embodiments the one or more bacteria may comprise *Serratia* (for example, *Serratia entomophilia* or *Serratia proteomaculans*), *Xanthamonas*, *Pseudomonas*, *Rhizobium*, *Bifidobacterium*, *Lactobacillus*, *Streptococcus* (*Enterococcus*), *Yersinia* (for example, *Yersinia entomophaga*), *Pseudomonas*, *Bacillus*, *Pasteuria*, *Azobacter*, *Enterobacter*, *Azospirillum*, *Cyanobacteria*, *Paecilomyces*, *Streptomycetes*, *Chromobacterium*, *Rhanella*, *Burkholderia*, *Paenibacillus*, *Collimonas*, *Sinorhizobium*, *Pantoea*, *Erwinia*, *Pediococus*, *Leuconostoc*, *Aeromonas*, *Neptunomonas*, *Klebsiella*, *Ponchonia*, *Brevibacillus*, *Acinetobacter*, *Paraburkholderia*, *Herbaspirillum*, *Bradyrhizobium*, *Methylobactenum*, *Ensifer*, *Sphingomonas*, *Azobacter*, *Lysobacter*, *Stenotrophomonas*, or any combination of two or more thereof.

In various embodiments the one or more fungi may comprise *Beauveria*, *Penicillium*, *Metarhizium*, *Trichoderma*, *Gliocladium*, *Coniothyrium*, *Paecilomyces*, *Verticillium*, *Sclerotinia*, and mycorrhizae or any combination of two or more thereof.

Bacterial and fungal microorganism suitable for use in the present invention preferably are selected from one or more genera of *Azotobacter*, *Bacillus*, *Stenotrophomonas*, *Serratia* and *Pseudomonas*, in addition to specific bacteria and fungi such as *Pseudomonas fluorescens*, *Azotobacter*, *Bacillus polymyxa*, *Stenotrophomonas rhizophila*, *Serratia plym-* uthica, *Trichoderma herzianum*, *Trichoderma viride* respectively, or any combination thereof.

Figure 1B:
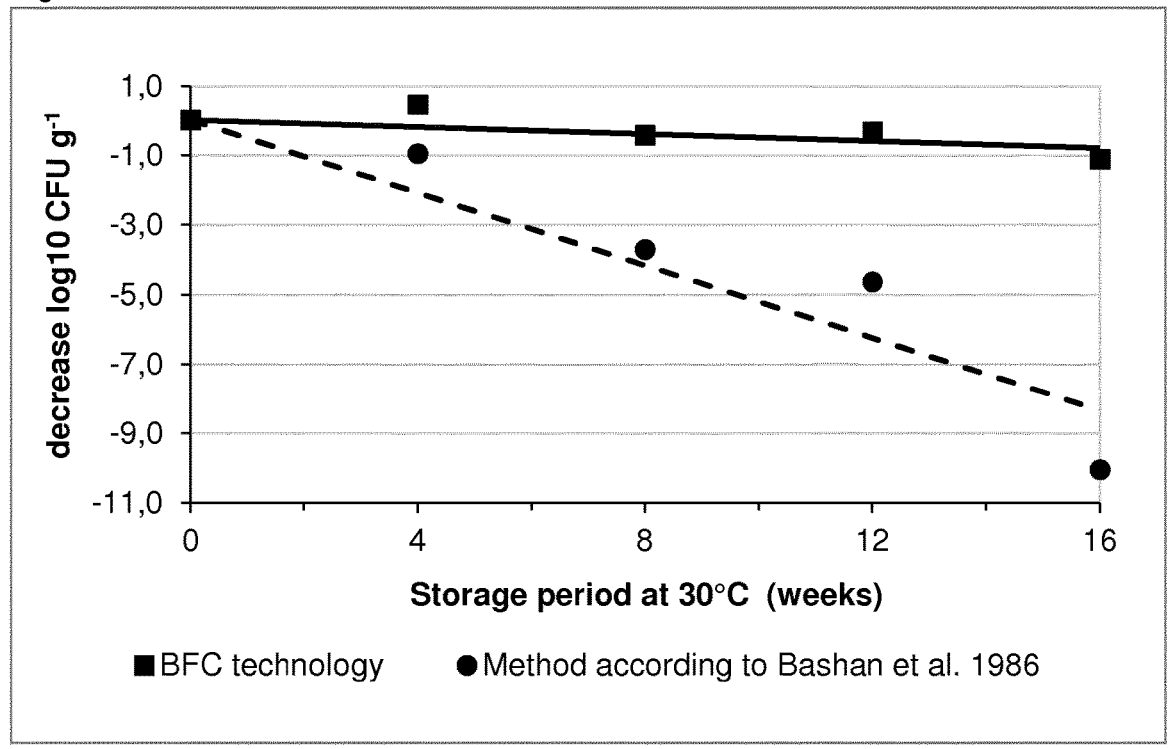
FIG. 1B: Viability of *Methylobacterium extorquens* Rab1 cells (Flavor enhancing bacterium for strawberry) formulated by the encapsulation method according to Bashan et al 1986 (circle) and by the inventive bacterial fungal conservation (BFC) technology (square); Storage conditions: 16 weeks at 30° C.
Figure 1C:
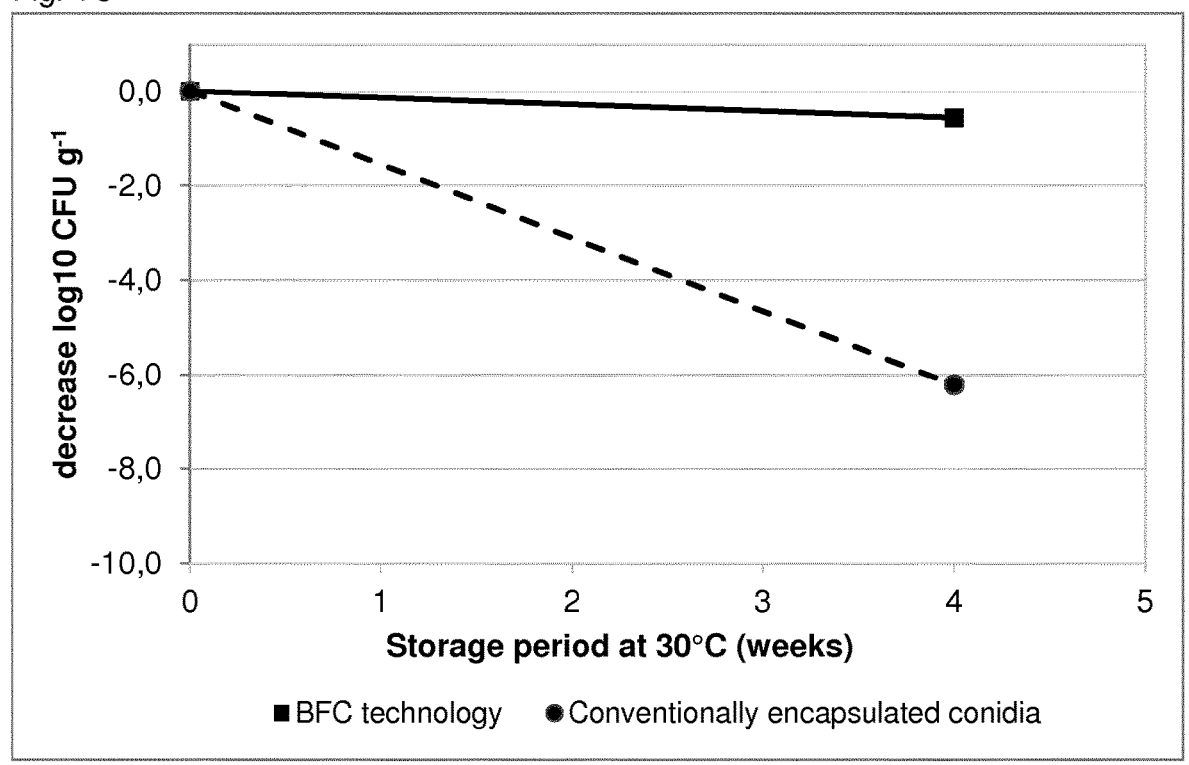
FIG. 1C: Viability of *Trichoderma* sp. (plant-growth promoting fungus) of conventionally encapsulated conidia (circle) and by the inventive bacterial fungal conservation (BFC) technology (square); Storage conditions: 4 weeks at 30° C.
Figure 2:
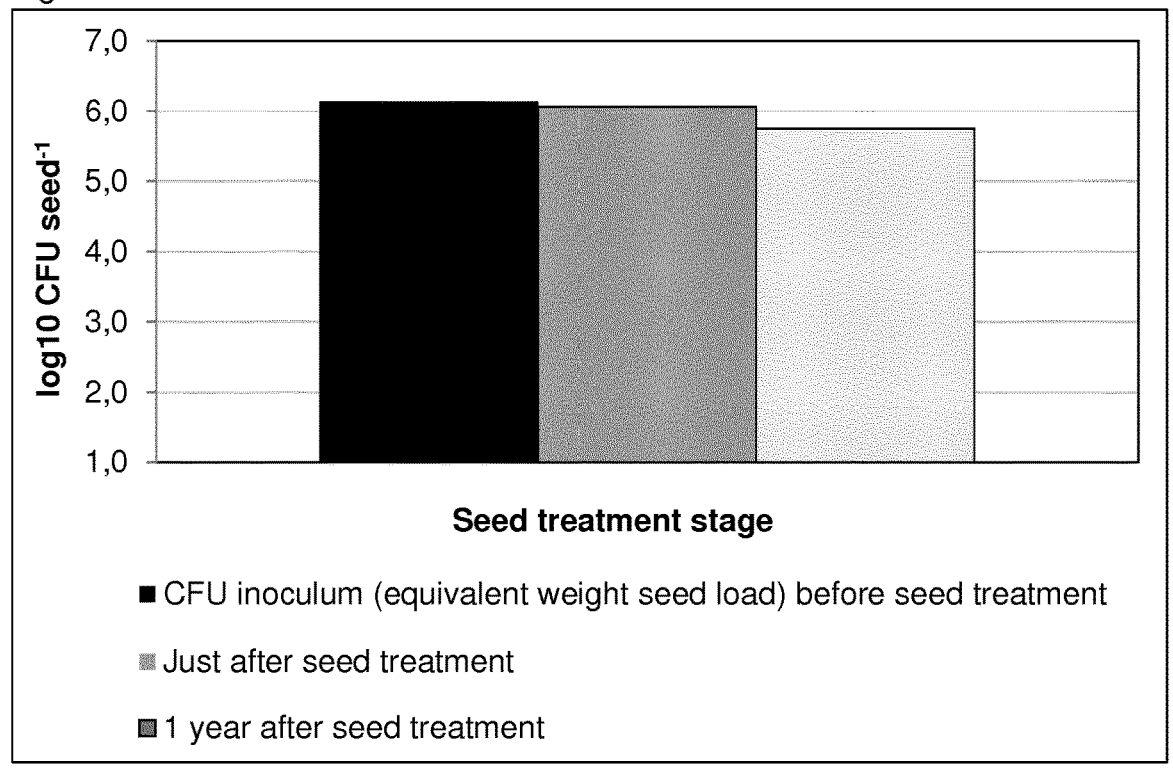
FIG. 2: Development of the viable cell counts over different stages of the product history starting from the dried product to one year after seed treatment. The cell numbers are specified as CFU per seed.
Figure 3:
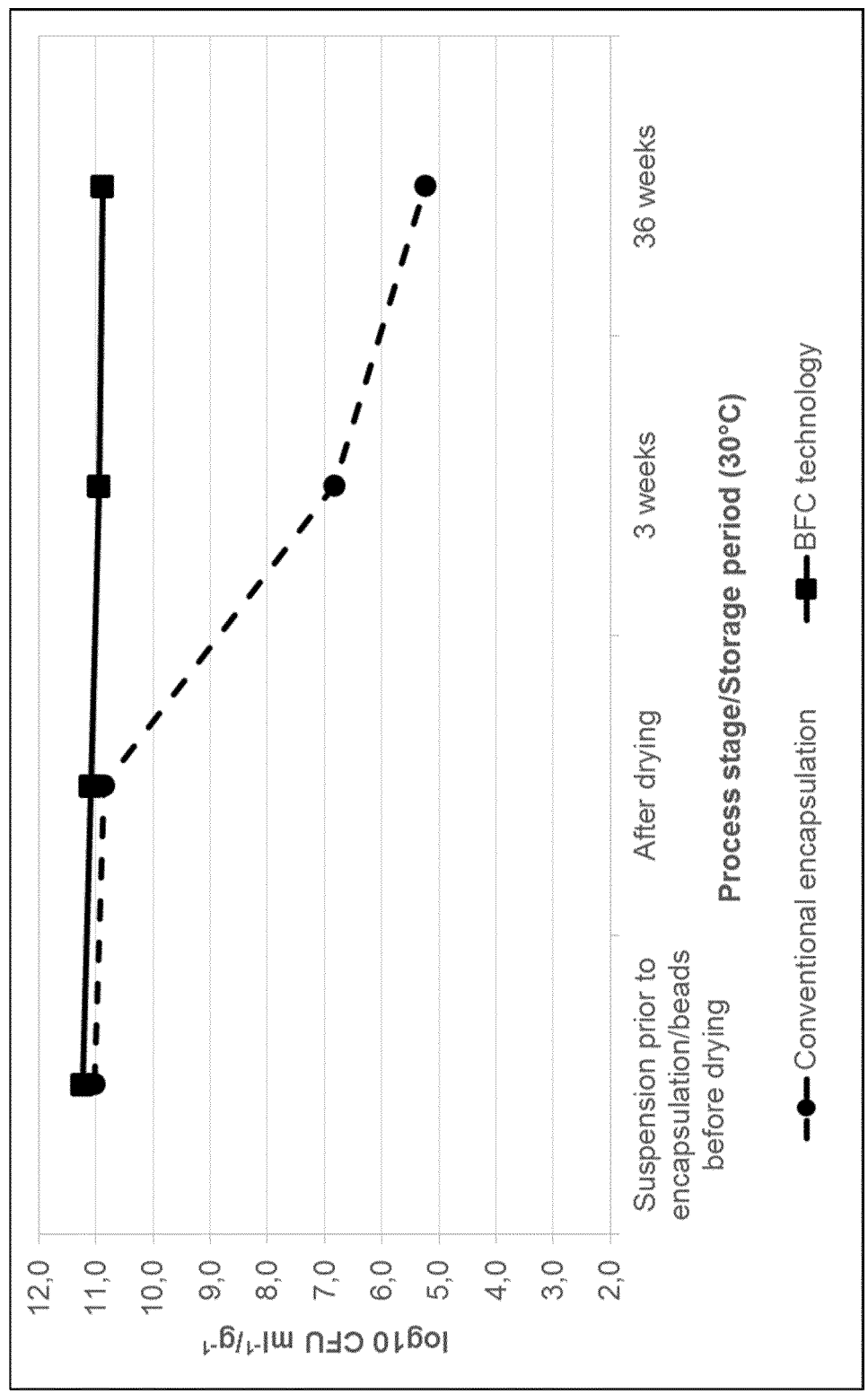
FIG. 3: Viability of *Stenotrophomonas rhizophila* cells formulated by encapsulation of planktonically grown cells ("conventional encapsulation") (circle) and by the inventive BFC technology (square) at 30° C. over a period of 36 weeks. For each encapsulation methodology the beads had a diameter of approximately 200 μm after drying, and between 480-600 μm when wet (prior to drying).
Figure 4:
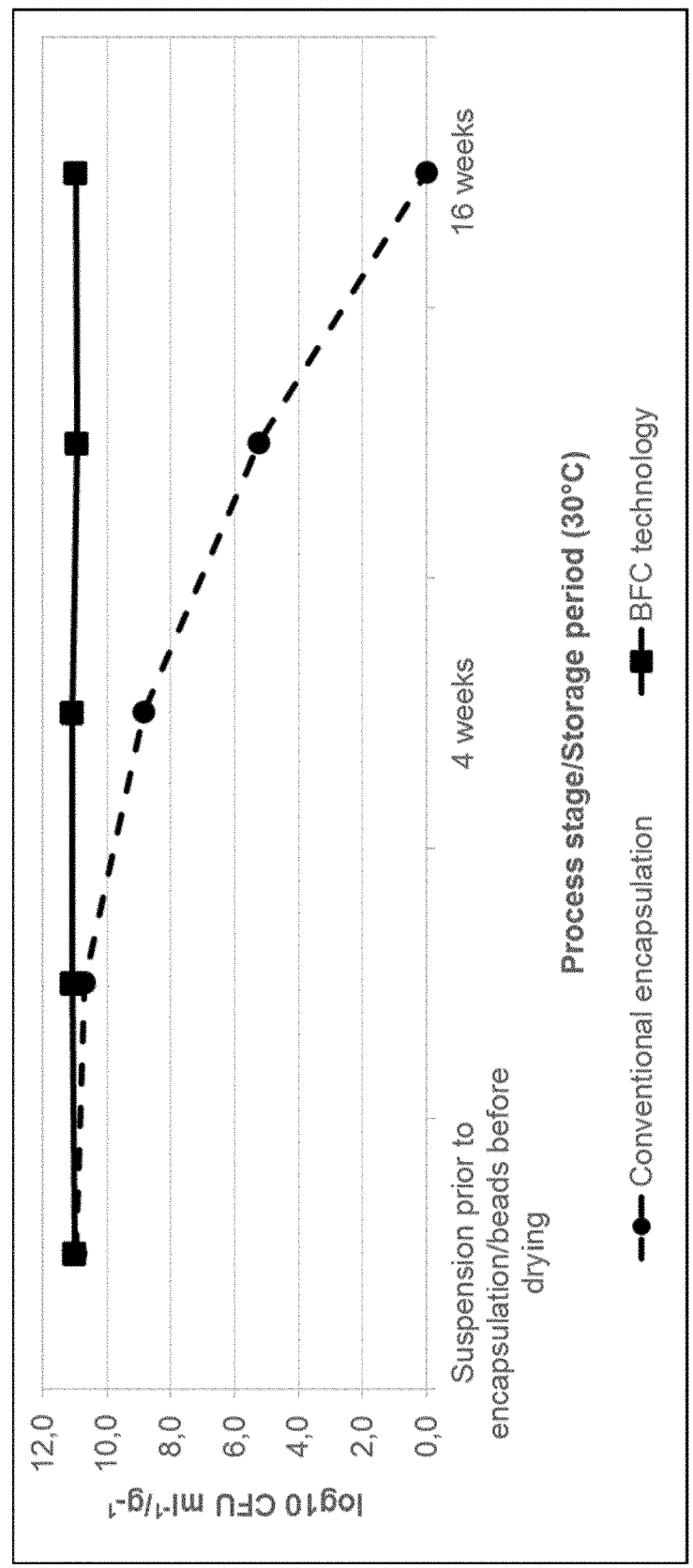
FIG. 4: Viability of *Methylobacterium extorquens* Rab1 cells formulated by encapsulation of planktonically grown cells ("conventional encapsulation") (circle) and by the inventive BFC technology (square) at 30° C. over a period of 16 weeks. For each encapsulation methodology the beads had a diameter of approximately 200 μm after drying, and between 480-600 μm when wet (prior to drying).

Using the present formulation method, the viability of microbial cells during storage and field application is improved compared to conventional method (see FIGS. 1A and 1B). The method is particularly suitable for sensitive microorganisms, such as Gram-negative bacteria but also fungi. Microbial cells formulated by that methods show survival rates during storage and when applied to seeds superior to other known methods. Moreover, due the compatibility with a broad range of strains the method allows a simultaneous formulation and cultivation of more than one microbial strain in a single preparation. Thus, the costs for the production of multi-strain preparation is reduced compared to individual cultivation approach.

EXAMPLES

The Examples which follow are set forth to aid in the understanding of the invention but are not intended to, and should not be construed to limit the scope of the invention in any way. The Examples do not include detailed descriptions of conventional methods, e.g., cultivation of microorganisms. Such methods are well known to those of ordinary skill in the art.

Example 1. Shelf-Life of Microorganisms Formulated by Bacterial and Fungal Conservation (BFC) Technology Results from strains with strain-specifically optimized fermentation and formulation parameter.

The potential of the stabilization formulation technology is exemplary demonstrated for selected plant-beneficial strains. The viability of microbial cells (CFU/g) produced by the invented technology was compared to conventionally encapsulated cells according to Bashan et al. (1986). Depending on the initial objective of a study, preparations were stored for different periods of time at 30° C.

Microbial cells propagated and formulated by the methods described herein show survival rates during storage and when applied e.g. to seeds superior to other known methods. Moreover, the methods described herein allow a simultaneous cultivation of more than one microbial strain in a single device. The invention involves two main concepts: i) a combined formulation and fermentation approach that enhances shelf-life stability and elevates the tolerance of formulated microbial cells towards desiccation and adverse effects during storage and application and ii) a method to cost-effectively cultivate more than one microbial strains in a single device. In a first step, individual pre-cultures from bacteria or fungi are obtained and suspended with a polymer solution that may contain additional carriers and additives. In some embodiments, the polymer solution is a 1.5-5% solution. In some embodiments, the polymer solution is an alginate solution. In some embodiments, the alginate solution is sodium alginate. In some embodiments, the sodium alginate solution is a 1.5-5.0% solution. Depending on the strain(s) to be inoculated the cell density is adjusted to $10^0$ to $10^8$ CFU/ml. In some embodiments, inoculation cell density is adjusted to about $10^4$ to $10^8$ CFU/ml. In some embodiments, inoculation cell density is adjusted to about $10^3$ to $10^7$ CFU/ml. In some embodiments, inoculation cell density is adjusted to about $10^2$ to $10^6$ CFU/ml. In some embodiments, inoculation cell density is adjusted to about $10^1$ to $10^5$ CFU/ml. In some embodiments, inoculation cell density is adjusted to about $10^0$ to $10^4$ CFU/ml. In some embodiments, inoculation cell density is adjusted to about $10^5$ to $10^8$ CFU/ml. In some embodiments, inoculation cell density is adjusted to about $10^4$ to $10^7$ CFU/ml. In some embodiments, inoculation cell density is adjusted to about $10^3$ to $10^6$ CFU/ml. In some embodiments, inoculation cell density is adjusted to about $10^2$ to $10^5$ CFU/ml. In some embodiments, inoculation cell density is adjusted to about $10^1$ to $10^4$ CFU/ml. In some embodiments, inoculation cell density is adjusted to about $10^0$ to $10^3$ CFU/ml. In some embodiments, inoculation cell density is adjusted to about $10^6$ to $10^8$ CFU/ml. In some embodiments, inoculation cell density is adjusted to about $10^4$ to $10^6$ CFU/ml. In some embodiments, inoculation cell density is adjusted to about $10^2$ to $10^4$ CFU/ml. In some embodiments, inoculation cell density is adjusted to about $10^0$ to $10^2$ CFU/ml. In some embodiments, inoculation cell density is adjusted to $10^1$ CFU/ml. In some embodiments, inoculation cell density is adjusted to $10^2$ CFU/ml. In some embodiments, inoculation cell density is adjusted to $10^3$ CFU/ml. In some embodiments, inoculation cell density is adjusted to $10^4$ CFU/ml. In some embodiments, inoculation cell density is adjusted to $10^5$ CFU/ml. In some embodiments, inoculation cell density is adjusted to $10^6$ CFU/ml. In some embodiments, inoculation cell density is adjusted to $10^7$ CFU/ml. In some embodiments, inoculation cell density is adjusted to $10^8$ CFU/ml.

Alginate bead formation was realized by dropping the solution into a $CaCl_2$) solution bath using a vibrating nozzle. After washing to remove remaining $CaCl_2$) solution, beads were transferred to a fermenter-like system for the in-bead cultivation which may be described as a fluidized bed reactor. Growth rates and maximal cell counts resembled those from planktonic cultures, but could be slightly higher. After 24 to 72 h of cultivation, the beads were washed again. Washed beads may, optionally be, treated with solutions containing osmoprotective compounds. The last step involved drying under ambient temperatures in appropriate drying devices (including, but not limited to a static bed in a drying chamber or drum dryer) for 24-30 hours. Depending on the microorganism and the applied protocol, the cell density in the final product ranged from $10^9$ to $10^{12}$ CFU/g dry weight. Methods described herein enhance the ability of the formulated (stabilized) microbial cells to outlast desiccation and starvation for the time of storage and application. The inventors made the novel and unexpected discovery that the combination of reduced inoculation density and subsequent in-bead cultivation is critical for final stability and long shelf life of the beads. In contrast to planktonic fermentation approaches, cells produced by the methods described herein are forced to multiply as colonies within the polymeric bead. Thereby, the cells produced by the methods described herein form biofilm-like structures including the generation of matrices made of extracellular polymeric substances. In fact, forming of and living in biofilms is the typical lifestyle of microorganisms in nature. Naturally, in biofilms embedded microorganisms survive adverse conditions due to the protective properties of the biofilm matrix. In one aspect of the invention, the genetic potential of any microorganism to form protective biofilms is artificially induced through a surprising combination of reduced inoculation density and in-bead cultivation, resulting in long-term improved survivability. Methods described herein are also suitable for cost-effective multi-strain fermentation. In some embodiments, only pre-culturing is performed in individual reactors, whereas the main cultivation is conducted in one single device. Moreover, the post-cultivation steps are simplified by processing only one preparation.

Example 2. Characterization of Stability of Compositions Produced Using BFC Technology A series of experiments were performed to show the contribution of steps in the BFC technology. *Stenotrophomonas rhizophlla* SPA-P69 (SPA-P69) was prepared using the following default parameters: SPA-P69 was grown in 0.5× Nutrient Broth II (SIFIN, Germany), and suspended in 1.5% sodium alginate solution to obtain a pre-culture cell density of $10^6$ CFU/ml. The composition of 0.5× Nutrient Broth II is 1.75 g/l casein peptone, 1.25 g/l meat peptone, 1.25 g/l gelatin peptone, 0.75 g/L yeast extract, and 2.5 g/l sodium chloride. Alginate beads were formed by dropping the solution into 150 mM $CaCl_2$), using a vibrating nozzle having nozzle diameter of 100 µm. The newly formed beads were washed to remove excess $CaCl_2$), and beads were transferred to a fluidized bed reactor, for secondary in-bead cultivation of encapsulated microorganisms at 22° C. for 48 hours. After cultivation the beads were washed before drying at ambient temperature in a static bed in a drying chamber for 24-30 hours. For these experiments these default parameters were modulated as described in the following table, and the viability of the encapsulated strains prepared using these experimental parameters were compared after various lengths of time in storage.

Figure 14:
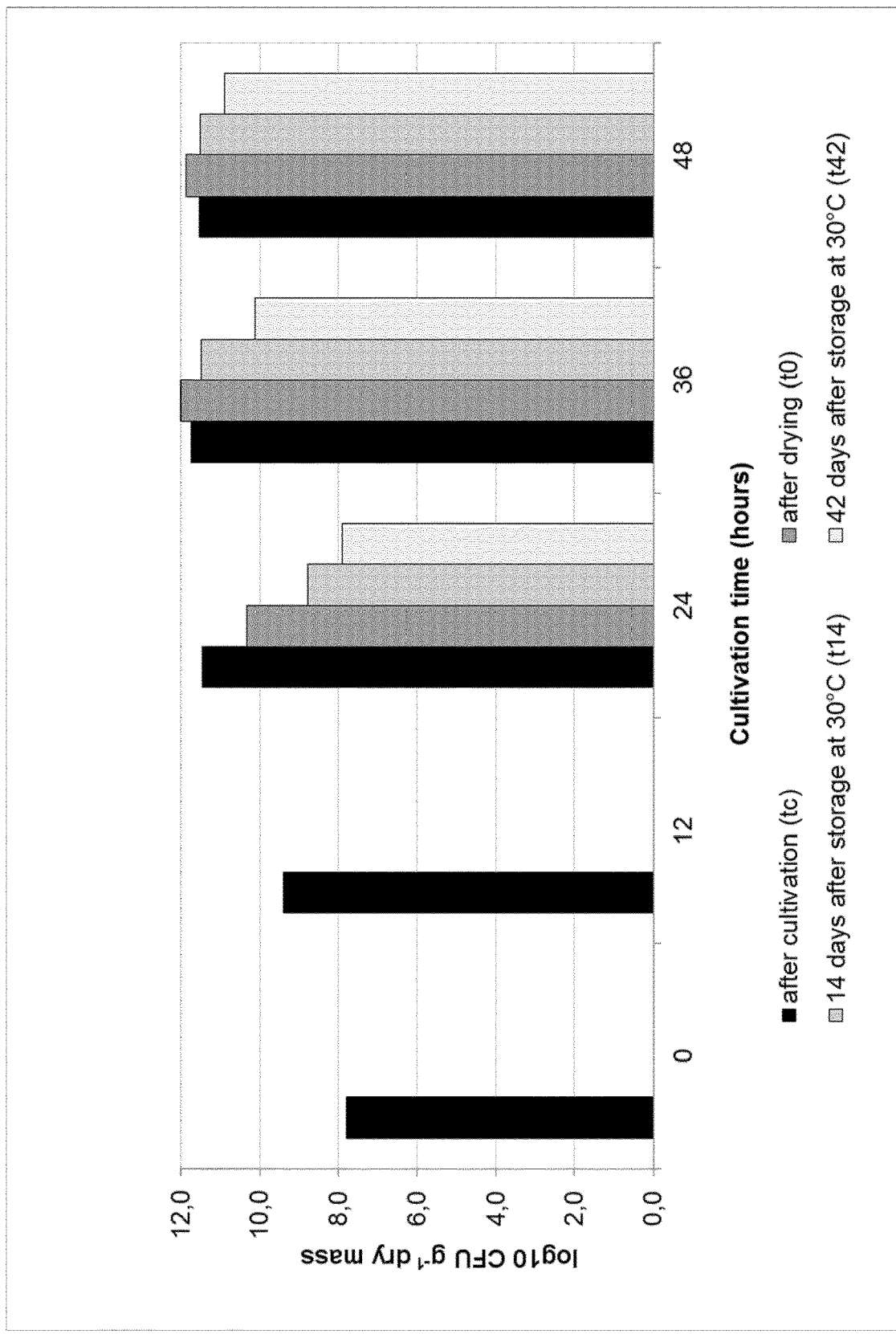
FIG. 14 Viability of *Stenotrophomonas rhizophila* SPA-P69 when formulated by the BFC technology using differing cultivation times of 0 hours, 12 hours, 24 hours, 36 hours and 48 hours, was assayed immediately after the cultivation step (tc), after the drying step (t0), 14 days after storage at 30° C., and 42 days after storage at 30° C. Encapsulated *S. rhizophlla* SPA-P69 that was not prepared with a secondary cultivation step was not detectable (n.d.) after the drying step, nor at 14 or 42 days. Similarly, encapsulated *S. rhizophlla* SPA-P69 that was prepared with a secondary cultivation step of 12 hours was not detectable (n.d.) after the drying step, nor at 14 or 42 days. Encapsulated *S. rhizophlla* SPA-P69 that was prepared with a secondary cultivation step of 24 hours resulted in a 3.57 log reduction in CFU/g dry biomass after 42 days of storage at 30° C. relative to the CFU/g dry biomass recorded immediately after cultivation. Encapsulated *S. rhizophlla* SPA-P69 that was prepared with a secondary cultivation step of 36 hours resulted in a 1.61 log reduction in CFU/g dry biomass after 42 days of storage at 30° C. relative to the CFU/g dry biomass recorded immediately after cultivation. Encapsulated *S. rhizophlla* SPA-P69 that was prepared with a secondary cultivation step of 48 hours resulted in a 0.65 log reduction in CFU/g dry biomass after 42 days of storage at 30° C. relative to the CFU/g dry biomass recorded immediately after cultivation.
Figure 15:
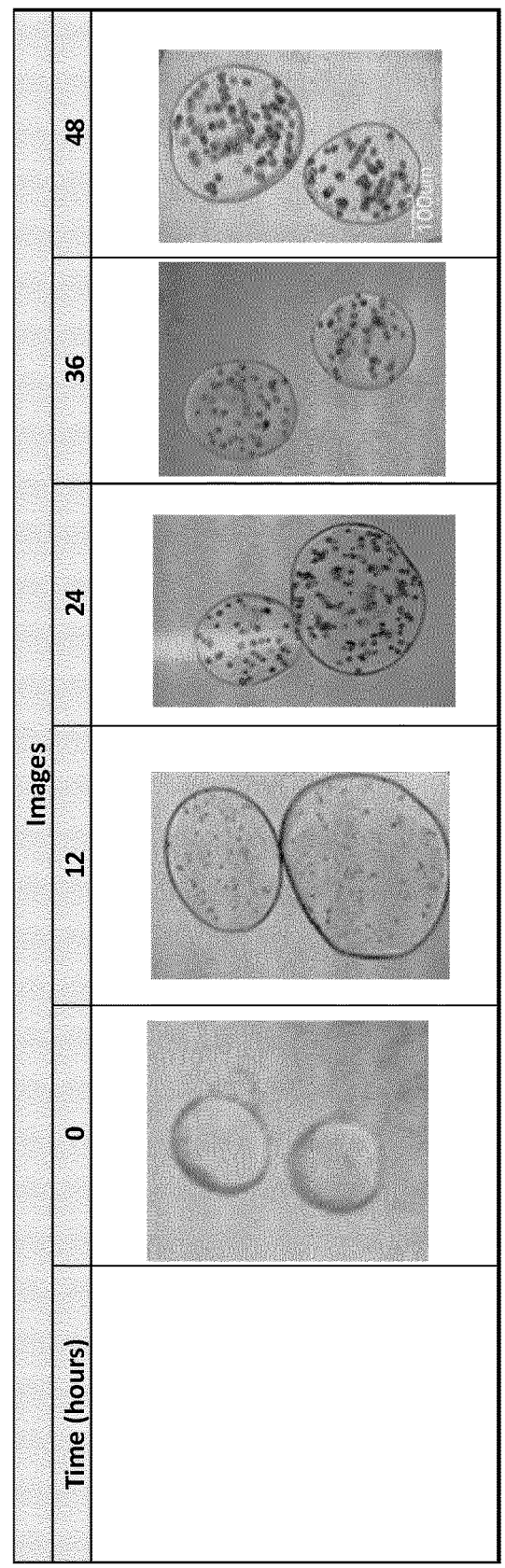
FIG. 15 Morphology of BFC encapsulated *Stenotrophomonas rhizophila* SPA-P69 before any secondary cultivation step (time hours 0), and after 12 hours of secondary cultivation, 24 hours of secondary cultivation, 36 hours of secondary cultivation, and 48 hours of secondary cultivation. The colony morphology becomes more distinct (well separated from other colonies) and dark with increasing time spent in secondary cultivation. All beads pictured were produced using an alginate concentration of 1.5%, $CaCl_2$) concentration of 150 mM, nozzle diameter of 100 μm, pre-culture inoculation density of $10^6$ CFU/ml, the strain was grown in 0.5× Nutrient Broth II (SIFIN, Germany) and cultivated at 22° C.

In a first experiment, the effect of the time spent in secondary cultivation was assayed. SPA-P69 was formulated by the BFC technology methodology described above except that the in-bead cultivation times were varied between samples. Encapsulated samples of SPA-P69 were subjected to in-bead cultivation of 0 hours, 12 hours, 24 hours, 36 hours and 48 hours and CFU/g dry mass was assayed immediately after the cultivation step (tc), after the drying step (t0), 14 days after storage at 30° C., or 42 days after storage at 30° C. Longer periods of in-bead cultivation resulted in increased survival of cells, this was especially noticeable when comparing samples that were stored for 42 days at 30° C. Encapsulated *S. rhizophlla* SPA-P69 that was prepared with an in-bead cultivation step of 48 hours resulted in a 0.65 log reduction in CFU/g dry biomass after 42 days of storage at 30° C. relative to the CFU per g dry biomass recorded immediately after cultivation. It is also noteworthy that samples that underwent in-bead cultivation of 36 or more hours showed enhanced survival of *S. rhizophlla* SPA-P69 in samples that had been dried relative to samples assayed immediately before the drying step. Results are shown in Table 2 and FIG. 14, images of exemplary beads are shown in FIG. 15.

TABLE 2

Effect of cultivation time on cell counts before, after drying and 42 days after storage at 30° C.

| Hours in-bead cultivation | After in-bead cultivation (tc) CFU/g dry mass wet beads | After drying (t0) CFU/g dry mass dried beads | After drying (t0) Δ log10 CFU/g dry mass (t0 − tc) | After 14 days storage at 30° C. (t14) CFU/g dry mass dried beads | After 14 days storage at 30° C. (t14) Δ log10 CFU/g dry mass (t14 − tc) | After 14 days storage at 30° C. (t14) % Δ log10 CFU/g dry mass (t14 − tc) | After 42 days storage at 30° C. (t42) CFU/g dry mass dried beads | After 42 days storage at 30° C. (t42) Δ log10 CFU/g dry mass (t42 − tc) | After 42 days storage at 30° C. (t42) % Δ log10 CFU/g dry mass (t42 − tc) |
|---|---|---|---|---|---|---|---|---|---|
| 0 | 7.79 | 0.00 | −7.79 | 0.00 | 0.00 | 0.00 | 0.00 | 0.00 | 0.00 |
| 12 | 9.40 | 0.00 | −9.40 | 0.00 | 0.00 | 0.00 | 0.00 | 0.00 | 0.00 |
| 24 | 11.46 | 10.31 | −1.15 | 8.78 | −2.68 | −25.98 | 7.90 | −3.57 | −31.12 |
| 36 | 11.73 | 12.00 | 0.27 | 11.48 | −0.26 | −2.14 | 10.13 | −1.61 | −13.71 |
| 48 | 11.53 | 11.88 | 0.35 | 11.52 | −0.01 | −0.09 | 10.88 | −0.65 | −5.62 |

TABLE 1

Default and varied parameters and conditions

| | |
|---|---|
| Strain | *Stenotrophomonas rhizophila* SPA-P69 |
| Alginate concentration | 1.5% (default) |
| $CaCl_2$ concentration | 150 mM (default) |
| Nozzle diameter | 100 µm (default) |
| | 75 µm |
| Inoculation density | 1 × $10^5$ CFU/ml |
| | 1 × $10^6$ CFU/ml (default) |
| | 1 × $10^7$ CFU/ml |
| | 1 × $10^8$ CFU/ml |
| Cultivation time | 12 h |
| | 24 h |
| | 36 h |
| | 48 h (default) |
| Cultivation medium | Nutrient broth II (default) |
| Cultivation temperature | 22° C. (default) |

Figure 16:
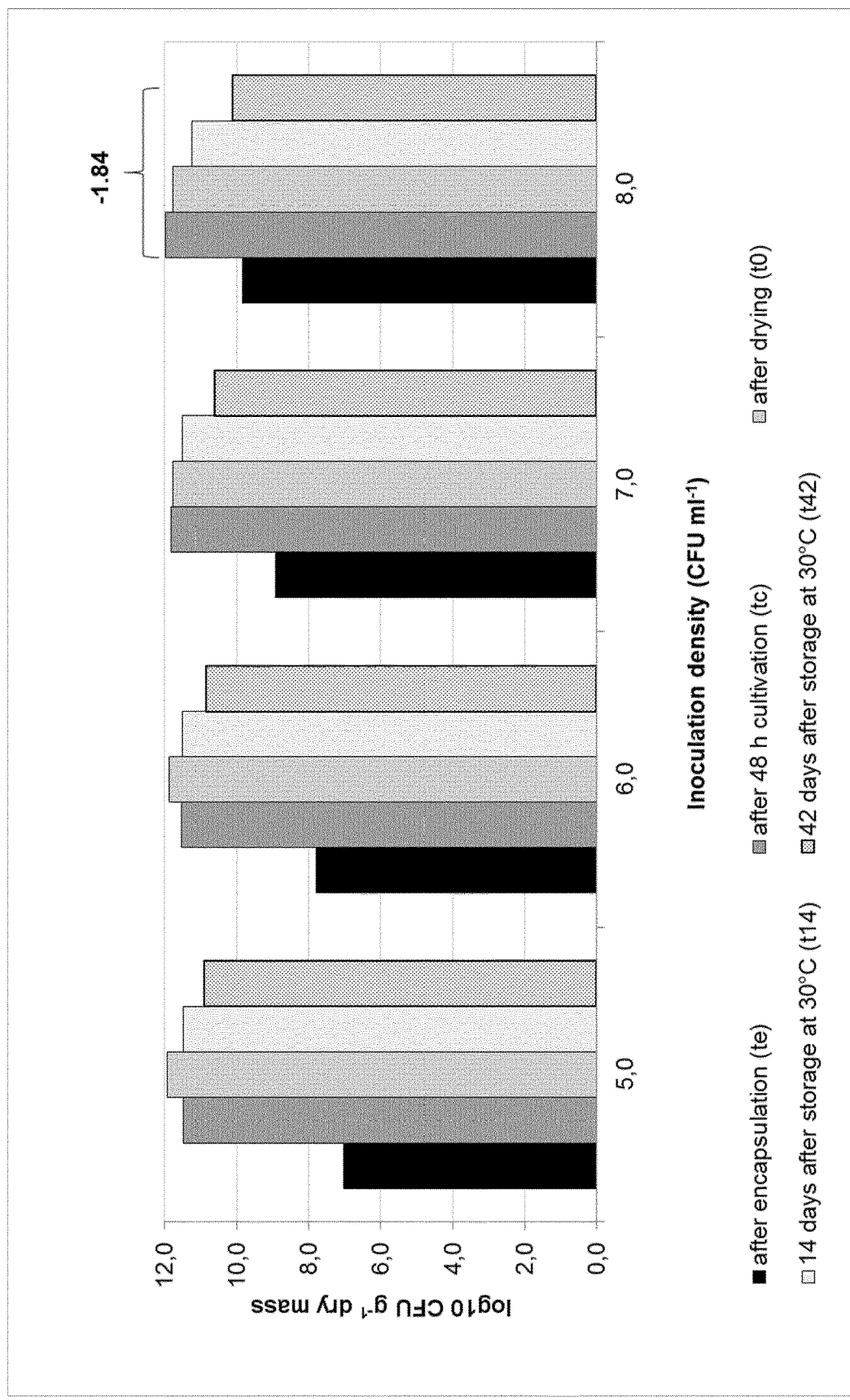
FIG. 16 Viability of *Stenotrophomonas rhizophila* SPA-P69 when formulated by the BFC technology using differing pre-in-bead culture inoculation densities ($10^5$ CFU/ml, $10^6$ CFU/ml, $10^7$ CFU/ml) after encapsulation but before secondary cultivation (te), immediately after the 48 hour secondary cultivation step (tc), after the drying step (t0), after 14 days of storage at 30° C. (t14), and after 42 days of storage at 30° C. (t42). The lower inoculation densities resulted in smaller log losses of CFU/g dry mass after storage relative to CFU/g dry mass detected immediately after the cultivation step. All beads sampled were produced using an alginate concentration of 1.5%, $CaCl_2$) concentration of 150 mM, nozzle diameter of 100 μm, pre-culture inoculation density of $10^6$ CFU/ml, the strain was grown in 0.5× Nutrient Broth II (SIFIN, Germany) and cultivated at 22° C. All beads sampled except for those labeled "te" underwent a 48 hour in-bead cultivation step.
Figure 17:
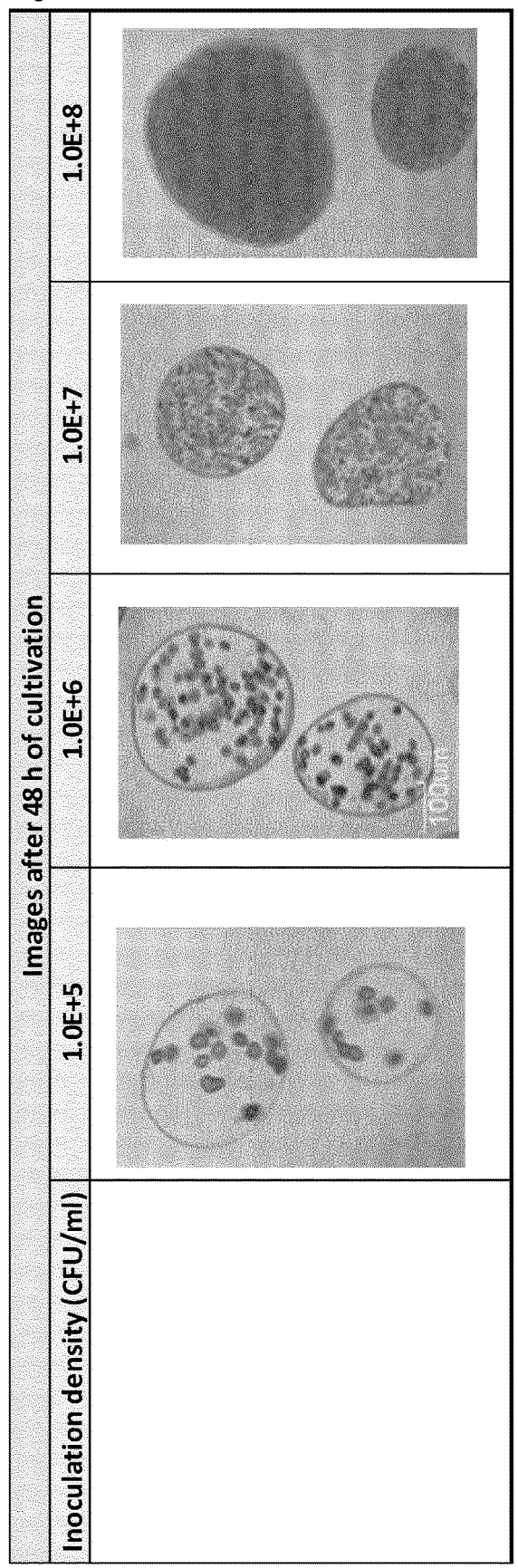

In a second experiment, the effect of pre-cultivation inoculation density was assayed. SPA-P69 was formulated by the BFC technology methodology using varying inoculation densities ($10^5$ CFU/mL, $10^6$ CFU/mL, $10^7$ CFU/mL). CFU/g dry mass was assayed after encapsulation but before in-bead cultivation (te), immediately after the 48 hour in-bead cultivation step (tc), after the drying step (t0), after 14 days of storage at 30° C. (t14), and after 42 days of storage at 30° C. (t42). The lower inoculation densities resulted in smaller log losses of CFU/g dry mass after storage relative to CFU/g dry mass detected immediately after the in-bead cultivation step. Results are shown in Table 3 and FIG. 16, images of exemplary beads are shown in FIG. 17. Table 4 describes characteristics of colonies formed within the beads prepared using the BFC technology methodology with differing inoculation densities.

TABLE 3

Effect of pre-cultivation inoculation density on cell counts before, after drying and 42 days after storage at 30° C.

| Inoculation density | After encapsulation (te) CFU/g dry mass wet beads | After 48 hour in-bead cultivation (tc) CFU/g dry mass wet beads | After 48 hour in-bead cultivation (tc) Δ log10 CFU/g dry mass (tc − te) | After drying (t0) CFU/g dry mass dried beads | After drying (t0) Δ log10 CFU/g dry mass (t0 − tc) | After 14 days storage at 30° C. (t14) CFU/g dry mass dried beads | After 14 days storage at 30° C. (t14) Δ log10 CFU/g dry mass (t14 − tc) | After 14 days storage at 30° C. (t14) % Δ log10 CFU/g dry mass (t14 − tc) | After 42 days storage at 30° C. (t42) CFU/g dry mass dried beads | After 42 days storage at 30° C. (t42) Δ log10 CFU/g dry mass (t42 − tc) | After 42 days storage at 30° C. (t42) % Δ log10 CFU/g dry mass (t42 − tc) |
|---|---|---|---|---|---|---|---|---|---|---|---|
| $10^5$ | 7.03 | 11.47 | 4.45 | 11.92 | 0.45 | 11.49 | 0.02 | 0.15 | 10.92 | −0.55 | −4.82 |
| $10^6$ | 7.79 | 11.53 | 3.74 | 11.88 | 0.35 | 11.52 | −0.01 | −0.09 | 10.88 | −0.65 | −5.62 |
| $10^7$ | 8.84 | 11.83 | 2.89 | 11.78 | −0.05 | 11.50 | −0.33 | −2.84 | 10.63 | −1.20 | 10.16 |
| $10^8$ | 9.85 | 11.97 | 2.12 | 11.76 | −0.21 | 11.24 | −0.74 | −6.25 | 10.13 | −1.84 | 15.41 |

TABLE 4

Characteristics of colonies formed within the beads prepared using the BFC technology methodology with differing inoculation densities

| | Inoculation density | | | |
|---|---|---|---|---|
| | 1.0E+5 | 1.0E+6 | 1.0E+7 | 1.0E+8 |
| Number of colonies/bead | 12.5 | 125 | 1250 | 12500 |
| Colony diameter (μm) | 16.42 | 9.33 | 5.58 | n.d. |
| Colony volume (μm^3) | 1.89E+4 | 3.37E+3 | 1.29E+3 | n.d. |
| CFU/colony | 1.14E+05 | 2.02E+4 | 7.74E+3 | n.d. |
| CFU/bead | 1.42E+06 | 2.53E+6 | 9.68E+6 | n.d. |

Example 3. Metabolic Profiling of Microorganisms Formulated by Bacterial and Fungal Conservation (BFC) Technology Using High Resolution Mass Spectrometry Preparation of Strains Using BFC and Reference Methods

*Stenotrophomonas rhizophlla* SPA-P69, *Sphingomonas sanguinis*, *Pseudomonas brassicacearum* L 13, and *Serratia plymuthica* 3Re were each individually formulated using the BFC methodology. To generate reference alginate encapsulated planktonically grown cells ("Alginate Planktonic"), cells in liquid culture were pelleted and resuspended in 1/10 the initial volume using 0.9% NaCl. The 10 fold concentrated cell suspension was mixed with alginate solution such that cell densities in the resulting alginate beads were similar to densities obtained after in-bead cultivation. Immediately following bead formation, Alginate Planktonic beads were air dried and stored at 30° C. Reference alginate encapsulated *Stenotrophomonas rhizophila* SPA-P69, *Pseudomonas brassicacearum* L13, and *Serratia plymuthica* 3Re were also prepared using the method of Bashan (1986).

Preparation of Samples

For metabolite analyses, about 100 mg cell mass for each sample and replicate (3 per microbe/method) were collected. Cell material from planktonically grown bacteria were obtained by pelleting 1.9 ml of a liquid culture in 2 ml tubes at 13,500×g for 15 min at 4° C. and discarding the supernatant. Samples from bacteria immobilized in alginate beads were prepared by dissolving 200 mg of dry beads in 40 ml 50 mM $Na_3C_6H_5O_7$ in 50 ml tubes using an orbital shaker for 3 hours at room temperature. The bacterial pellet was obtained by two centrifugation steps. The first centrifugation step was done at 9,000×g for 20 min at 10° C. After discarding the supernatant, the remaining pellet was re-suspended in 1.0 ml 50 mM $Na_3C_6H_5O_7$ followed by an additional centrifugation step at 13,500×g for 15 min at 4° C. and removal of the supernatant. The mass of alginate pellets were weighed.

For disrupting bacterial cells, the pellet was re-suspended in 1 ml −70° C. cold methanol, transferred to 2 ml screw-capped tubes containing 250 mg glass beads with a diameter of 0.25-0.5 mm and three glass beads with a diameter of 3 mm, and treated using the FastPrep-24 Instrument (MPBio-medicals, Illkrich, France) for 2×30 s at speed level 4 (lowest). Finally, to remove cell debris, the suspension was centrifuged at 13,500 for 15 min at 4° C. 500 μl of the supernatant was collected and stored at −70° C. until analysis. For preparing sample blanks of the cultivation medium (NBII), aliquots of 100 μl nutrient broth II were mixed with 1 ml methanol. Sample blanks for alginate beads derived samples were obtained by dissolving 2 g of wet, sterile alginate beads in 40 ml $Na_3C_6H_5O_7$ (50 mM) and mixing 100 μl of the solution with 1 ml methanol.

The characteristics of the samples are additionally described in Table 5.

TABLE 5

Average characteristics of samples prepared for metabolite profiling.

| | *Stenotrophomonas rhizophila* SPA-P69 | | | | *Sphingomonas sanguinis* | | |
|---|---|---|---|---|---|---|---|
| | BFC (in-bead cultivation) | Planktonic | Alginate encapsulated planktonic | Bashan | BFC (in-bead cultivation) | Planktonic | Alginate encapsulated planktonic |
| Cell count/ml (g dry beads) | 1.78E+11 | 2.96E+09 | 6.78E+10 | 9.11E+10 | 8.43E+09 | 2.65E+09 | 7.01E+09 |
| Volume ml (mass g) of sample | 2.00E−01 | 1.50E+00 | 2.00E−01 | 2.00E−01 | 2.00E−01 | 1.50E+00 | 2.00E−01 |

TABLE 5-continued

Average characteristics of samples prepared for metabolite profiling.

| | Stenotrophomonas rhizophila SPA-P69 | | | | Sphingomonas sanguinis | | |
|---|---|---|---|---|---|---|---|
| | BFC (in-bead cultivation) | Planktonic | Alginate encapsulated planktonic | Bashan | BFC (in-bead cultivation) | Planktonic | Alginate encapsulated planktonic |
| Weight of pellet (mg) | 1.07E+02 | 9.78E+01 | 1.03E+02 | 1.02E+02 | 1.02E+02 | 9.61E+01 | 1.00E+02 |
| Calculated CFU/LC-MS Sample | 3.57E+10 | 4.45E+09 | 1.36E+10 | 1.82E+10 | 1.69E+09 | 3.97E+09 | 1.40E+09 |

Metabolic Profiling Using High Resolution Mass Spectrometry

For metabolite analysis, a Thermofisher, HPLC and Orbitrap (Q-Exactive) HPLC-MS-System was used with the following specifications: Column was an Atlantis dC18, 3 µm, 2.1×100 mm; Flow was set at 0.3 ml/min; Gradient was 10% B (2 min)-50% B (5 min)-80% (15 min)-10% B (5 min), with a total run time of 40 min; Mobile Phase A was 0.1% Formic Acid/H2O$_{dd}$; B: 0.1% Formic Acid/Acetonitril.

Specific mass spec parameters were as follows: Voltage. 3100; Capillary Temperature: 330; Positive, Negative Mode extra; Resolution: 70.000, AGC target: 1e6, Maximum IT: 200 ms, Scan Range: 100 to 1500 m/z; MΩ-Parameter: Resolution: 17.500.

Mass spec general settings were as follows: Precursor Selection: Use MS(n−1) Precursor; Use New Precursor Reevaluation: True; Use Isotope Pattern in Precursor Reevaluation: True; Store Chromatograms: False.

Spectrum Properties Filter settings were as follows: Lower RT Limit: 0; Upper RT Limit: 0; First Scan: 0; Last Scan: 0; —Ignore Specified Scans: (not specified); Lowest Charge State: 0; Highest Charge State: 0; Min. Precursor Mass: 100 Da; Max. Precursor Mass: 5000 Da; Total Intensity Threshold: 0; Minimum Peak Count: 1.

Scan Event Filter settings were as follows: Mass Analyzer: (not specified); —MS Order: Any; Activation Type: (not specified); Min. Collision Energy: 0; Max. Collision Energy: 1000; Scan Type: Any; Polarity Mode: (not specified).

Peak filter settings were as follows: S/N Threshold (FT-only): 1.5. Replacements for Unrecognized Properties settings were as follows: Unrecognized Charge Replacements: 1; Unrecognized Mass Analyzer Replacements: ITMS; Unrecognized MS Order Replacements: MS2; Unrecognized Activation Type Replacements: CID; Unrecognized Polarity Replacements: +; Unrecognized MS Resolution@200 Replacements: 60000; Unrecognized MSn Resolution@200 Replacements: 30000.

HPLC mass spec data analysis was performed using Compound Discoverer version 2.1.0.398 (Thermofisher) and an untargeted metabolomics workflow to find and identify the differences between samples. The workflow data analysis included retention time alignment, unknown compound detection, and compound grouping across all samples, predicted elemental compositions for all compounds, filled gaps across all samples, and hid chemical background (using Blank samples).

For grouping unknown compounds, Compound Consolidation settings were as follows: Mass Tolerance: 5 ppm, RT Tolerance [min]: 0.05. Fragment Data Selection used the following Preferred Ions: [M+H]+1; [M−H]−1. To fill gaps, the following General Settings were used: Mass Tolerance: 5 ppm, S/N Threshold: 1.5, Use Real Peak Detection: True.

To normalize areas, QC-based Area Correction settings were as follows: Regression Model: Linear, Min. QC Coverage [%]: 50, Max. QC Area RSD [%]: 30, Max. # Files Between QC Files: 20. Area Normalization settings were as follows: Normalization Type: None, Exclude Blanks: True.

For unknown compound detection mass tolerance was set at 5 ppm, intensity tolerance at 30%, S/N threshold of 3, min. peak intensity of 1000000, ions: [2M+ACN+H]+1, [2M+ACN+Na]+1, [2M+FA−H]−1, [2M+H]+1, [2M+Na]+1, [2M+NH4]+1, [2M−H]−1, [2M−H+HAc]−1, [M+2H]+2, [M+3H]+3, [M+ACN+2H]+2, [M+ACN+H]+1, [M+ACN+Na]+1, [M+Cl]−1, [M+FA−H]−1, [M+H]+1, [M+H+K]+2, [M+H+Na]+2, [M+H+NH4]+2, [M+H−H2O]+1, [M+H−NH3]+1, [M+K]+1, [M+Na]+1, [M+NH4]+1, [M−2H]−2, [M−2H+K]−1, [M−H]−1, [M−H+HAc]−1, [M−H−H2O]−1, Base Ions: [M+H]+1; [M−H]−1, Min. Element Counts: C H, Max. Element Counts: C90 H190 Cl4 K2 N10 Na2 O15 P3 S5.

For peak detection, —the following settings were used: Filter Peaks: True, Max. Peak Width [min]: 0.5, Remove Singlets: True, Min. # Scans per Peak: 5, Min. # Isotopes: 1. QC-based area correction and area normalization settings were as follow: QC-based Area Correction: Regression Model: Linear, Min. QC Coverage [%]: 50, Max. QC Area RSD [%]: 30, Max. # Files Between QC Files: 20; Area Normalization: Normalization Type: None, Exclude Blanks: True. Composition prediction settings were as follows: Mass Tolerance: 5 ppm, Min. Element Counts: C H, Max. Element Counts: C90 H190 Cl4 N10 O18 P3 S5, Min. RDBE: −1, Max. RDBE: 40, Min. H/C: 0.1, Max. H/C: 4, Max. # Candidates: 10, Max. # Internal Candidates: 200. Fragment matching settings were as follows: Use Fragments Matching: True, Mass Tolerance: 5 mmu, S/N Threshold: 3.

Compounds were identified using mzCloud (ddMS2) and ChemSpider (formula or exact mass). mzCloud search settings were as follows: Compound Classes: All, Match Ion Activation Type: False, Match Ion Activation Energy: Match with Tolerance, Ion Activation Energy Tolerance: 20, Apply Intensity Threshold: True, Precursor Mass Tolerance: 10 ppm, FT Fragment Mass Tolerance: 10 ppm, IT Fragment Mass Tolerance: 0.4 Da, Identity Search: HighChem HighRes, Similarity Search: Similarity Forward, Library: Reference, Post Processing: Recalibrated, Match Factor Threshold: 50, Max. # Results: 10. Pattern matching settings were as follows: Intensity Tolerance [%]: 30, Intensity Threshold [%]: 0.1, S/N Threshold: 3, Min. Spectral Fit [%]: 30, Min. Pattern Coy. [%]:90, Use Dynamic Recalibration: True.

ChemSpider used the following data sources: BioCyc, E. coli Metabolome Database, Human Metabolome Database, KEGG, MeSH, NIST Chemistry WebBook Spectra, PubChem, and the Yeast Metabolome Database.

Similarity searches were also performed for all compounds with ddMS2 data using mzCloud. Compounds were mapped to biological pathways using KEGG database. Map to KEGG pathway used the following settings: 1. By Mass Search Settings: Mass Tolerance: 5 ppm; 2. By Formula Search Settings: Max. # of Predicted Compositions to be searched per Compound: 3, and 3. Display Settings: Max. # Pathways in 'Pathways' column: 20.

QC-based batch normalization was applied when QC samples were available. Workflow also included differential analysis calculation (t-test or ANOVA), p-value determination, adjusted p-value determination, ratios, fold change, and CV.

Using ThermoFisher Compound Discoverer, comma-separated variable (CSV) files representing the Input Files Table and Expected Features Table were exported as described in the Thermo Compound Discoverer User Guide (available at thermofisher.com). All downstream processing and analysis was performed in the R statistical language R, version 3.5.1 (R Core Team, 2016. R: A language and environment for statistical computing. R Foundation for Statistical Computing, Vienna, Austria. R-project.org/). Unless stated otherwise, all analyses were performed identically but separately for positive and negative ion datasets. Peak groups were constructed using the XCMS function do_groupChromPeaks_nearest with default parameters (Smith et al. (2006). XCMS: Processing mass spectrometry data for metabolite profiling using Nonlinear peak alignment, matching, and identification. Analytical Chemistry, 78:779-787). Within each sample, intensities of peaks having identical m/z and retention time were summed. All sample datasets were aggregated into a single matrix, with a NA indicator representing the absence of detection of a particular peak in a particular sample. To increase dataset density, metabolites represented by NA in over half of the samples were removed. Remaining NA values were replaced with a minimum intensity value, defined as one-half of the smallest, non-zero intensity of the dataset. To normalize intensity levels across the samples, quantile normalization was performed using the "normalize.quantiles" function in the preprocessCore package Bolstad B (2018). *preprocessCore: A collection of pre-processing functions*. R package version 1.42.0, available at github.com/bmbolstad/preprocessCore). Normalized intensities were log-2 transformed for subsequent statistical analysis.

To reduce unnecessary multiplicity of statistical hypothesis testing, non-specific filtering was performed using genefilter [Gentleman2018] to eliminate metabolites with a coefficient of variance less than 0.03 or an interquantile range of less than 0.5. Statistical t-testing was performed with the limma function lmFit (Ritchie et al. (2015). "limma powers differential expression analyses for RNA-sequencing and microarray studies." Nucleic Acids Research, 43(7), e47.), using an empirical Bayesian estimate for variance via the eBayes function, and using the topTable function to obtain a Benjamini and Hochberg p-value adjustment. To project metabolites onto known metabolic pathways and compound names, the mummichog algorithm (Li et al. Predicting Network Activity from High Throughput Metabolomics. Ouzounis CA, ed. PLoS Computational Biology. 2013; 9(7):e1003123) was used via the implementation in MetaboAnalystR (Chong & Xia (2018) MetaboAnalystR: an R package for flexible and reproducible analysis of metabolomics data. Bioinformatics. 2018 Jun. 28). The InitDataObjects was called with analysis type set to "mummichog", followed by UpdateMummichogParameters with instrumentOpt set to "0.1", ion polarity set to positive or negative, and pvalCutoff set to 1.0E-6. Finally, the PerformMummichog function was called with an appropriate prokaryote model, along with "fisher" and "gamma" parameters for enrichOpt and pvalOpt, respectively. Compound identifiers were mapped to the corresponding descriptive KEGG names (Kanehisa & Goto (2000) KEGG: kyoto encyclopedia of genes and genomes. Nucleic Acids Res. 28(1):27-30). The log fold change was adjusted to reflect the relative CFU/LC-MS sample.

Compounds increased in BFC formulated *Sphingomonas sanguinis* and *Stenotrophomonas rhizophlla* SPA-P69 relative to reference compositions are shown in Table 6A. Compounds increased in BFC formulated *Sphingomonas sanguinis* relative to reference composition Alginate Planktonic are shown in Table 6B. EPS refers to an extracellular polymeric substance. Exemplary compounds should be understood to include related compounds such as oxidized and reduced forms and derivatives.

TABLE 6A

Compounds increased in BFC formulated *Sphingomonas sanguinis* and *Stenotrophomonas rhizophila* SPA-P69 relative to reference compositions

| Classes or Functions | Exemplary Compound(s) | Range of titer-adjusted fold-change relative to reference compositions | *Sphingomonas sanguinis* Titer-adjusted fold-change of BFC relative to reference composition Alginate Planktonic | *Stenotrophomonas rhizophila* SPA-P69 Titer-adjusted fold-change of BFC relative to reference composition Alginate Planktonic | Titer-adjusted fold-change of BFC relative to reference composition Bashan |
|---|---|---|---|---|---|
| Other | naphthazarin | 13.8-485.3 | 485.33 | 13.83 | 75.04 |
| Vitamin/Redox | NAD+/NADH | 1.25-4.0 | 3.13 | 3.73 | 3.98 |
| | Thiamine | 2.3-143.5 | 143.48 | 9.59 | 2.26 |
| | Adenine | 1.1-15.9 | 7.46 | 15.95 | 1.07 |
| AA, protein, EPS | tryptophan | 1.7-13.9 | 13.89 | 2.77 | 3.79 |
| | phenylalanine | 1.3-4.4 | 4.40 | 1.28 | 1.58 |
| AA, non-protein | homocysteine | 3.7-16.1 | 16.09 | 6.65 | 3.69 |
| Stabilization | tryptophan | 1.7-13.9 | 13.89 | 2.77 | 3.79 |
| Pathway | homocysteine | 3.7-16.1 | 16.09 | 6.65 | 3.69 |
| cycling | erythrose 4-phosphate | 3.2-9.7 | 8.06 | 2.03 | 1.64 |

TABLE 6A-continued

Compounds increased in BFC formulated *Sphingomonas sanguinis* and *Stenotrophomonas rhizophila* SPA-P69 relative to reference compositions

| Classes or Functions | Exemplary Compound(s) | Range of titer-adjusted fold-change relative to reference compositions | *Sphingomonas sanguinis* Titer-adjusted fold-change of BFC relative to reference composition Alginate Planktonic | *Stenotrophomonas rhizophila* SPA-P69 Titer-adjusted fold-change of BFC relative to reference composition Alginate Planktonic | *Stenotrophomonas rhizophila* SPA-P69 Titer-adjusted fold-change of BFC relative to reference composition Bashan |
|---|---|---|---|---|---|
| | pyridoxine phosphate | 3.1–5.3 | 4.40 | 1.28 | 1.58 |
| | phenylalanine | 1.3–4.4 | 4.40 | 1.28 | 1.58 |

TABLE 6B

Compounds increased in BFC formulated *Sphingomonas sanguinis* relative to reference composition Alginate Planktonic

| Classes/ Functions | Exemplary Compound(s) | *Sphingomonas sanguinis* Titer-adjusted fold-change of BFC relative to reference composition Alginate Planktonic |
|---|---|---|
| Other | naphthazarin | 485.33 |
| Vitamin/Redox | Thiamine | 143.48 |
| | Nicotinamide | 8.12 |
| | Adenine | 7.46 |
| | NAD+/NADH | 3.13 |
| Stabilization | glutamic acid/glutamate | 55.44 |
| | tryptophan | 13.89 |
| | spermidine | 6.07 |
| | Pyocyanin | 1.55 |
| Pathway cycling | homocysteine | 16.09 |
| | adenosine | 10.18 |
| | erythrose 4-phosphate | 8.06 |
| | pyridoxine phosphate | 4.40 |
| | phenylalanine | 4.40 |
| | methionine | 4.16 |
| | N-methylene-L-glutamate | 0.91 |
| Other | methylthioninium chloride | 1.82 |
| EPS | glucosamine/chitosamine | 6.58 |
| DNA/RNA, EPS | Cytosine/adenine | 8.95 |
| Antioxidant | glutathione | 97.31 |
| | citric acid | 8.21 |
| | Pyocyanin | 1.55 |
| AA, protein, EPS | glutamic acid/glutamate | 55.44 |
| | tryptophan | 13.89 |
| | tyrosine | 6.58 |
| | phenylalanine | 4.40 |
| | methionine | 4.16 |
| | lysine | 2.70 |
| | proline | 2.63 |
| AA, non-protein | homocysteine | 16.09 |

TABLE 6C

Compounds increased in BFC formulated *Stenotrophomonas rhizophila* SPA-P69 relative to reference compositions

| Classes/ Functions | Exemplary Compound(s) | *Stenotrophomonas rhizophila* SPA-P69 Titer-adjusted fold-change of BFC relative to reference composition Alginate Planktonic | *Stenotrophomonas rhizophila* SPA-P69 Titer-adjusted fold-change of BFC relative to reference composition Bashan |
|---|---|---|---|
| Other | naphthazarin | 13.83 | 75.04 |
| AA, non-protein | homocysteine | 6.65 | 3.69 |
| AA, protein, EPS | tryptophan | 2.77 | 3.79 |
| | phenylalanine | 1.28 | 1.58 |
| Osmolyte | Rhamnose | 1.48 | 2.38 |
| Pathway cycling | homocysteine | 6.65 | 3.69 |
| | erythrose 4-phosphate | 2.03 | 1.64 |
| | pyridoxine phosphate | 1.28 | 1.58 |
| | phenylalanine | 1.28 | 1.58 |

TABLE 6C-continued

Compounds increased in BFC formulated *Stenotrophomonas rhizophila* SPA-P69 relative to reference compositions

| | | *Stenotrophomonas rhizophila* SPA-P69 | |
|---|---|---|---|
| Classes/ Functions | Exemplary Compound(s) | Titer-adjusted fold-change of BFC relative to reference composition Alginate Planktonic | Titer-adjusted fold-change of BFC relative to reference composition Bashan |
| Stabilization | tryptophan | 2.77 | 3.79 |
| Vitamin/Redox | NAD+/NADH | 3.73 | 3.98 |
| | Thiamine | 9.59 | 2.26 |
| | Adenine | 15.95 | 1.07 |

Example 4. Colony Characteristics within BFC Produced Beads

*Paraburkholderia caledonica* and *Enterobacter cowanii* were prepared by the BFC method using pre-culture inoculation densities of between 2E+7 and 4E+7 with differing times of in-bead cultivation, and for *Enterobacter cowanii* differing alginate percentages and nozzle diameters were used.

*Paraburkholderia caledonica* samples were prepared using an 80 μm diameter nozzle and a 2% alginate solution. In-bead cultivation was performed for 47, 138, or 168 hours. *Enterobacter cowanii* samples were prepared using 80 μm diameter nozzle and a 120 μm diameter nozzle and 2% and 3% alginate solutions. In-bead cultivation was performed for 50, 70, or 71 hours. Beads produced by the 80 μm diameter nozzle produced beads had an average diameter of 186 μm and a range of 134-235 μm when wet, and an average diameter of 78 μm and range of 50-103 μm after drying. The beads had approximately between 2 and 100 colonies per bead. The average, smallest and largest bead diameters are listed in Tables 7A and 7B. Colony diameter was measured at the widest point of the colony. Colony measurements were made in wet beds. Increasing in-bead cultivation time resulted in only moderate increases in colony diameter.

TABLE 7A

Colony size measurements of BFC encapsulated *Paraburkholderia caledonica*
*Paraburkholderia caledonica* Colony Size Measurements

| Batch | Time (hr) | Smallest colony (μm) | Average colony (μm) | Largest colony (μm) |
|---|---|---|---|---|
| 180907-80 μM-2% Alginate | 47 | 16 | 21 | 35 |
| 180907-80 μM-2% Alginate | 138 | 15 | 25 | 37 |
| 180907-80 μM-2% Alginate | 168 | 19 | 27 | 41 |
| | Avg: | 16 | 24 | 38 |

TABLE 7B

Colony size measurements of BFC encapsulated *Enterobacter cowanii*
*Enterobacter cowanii* Colony Size Measurements

| Batch | Time (hr) | Smallest colony (μm) | Average (μm) | Largest (μm) |
|---|---|---|---|---|
| 180803-175-80 μM: 2% Alginate | 50 | 21 | 32 | 40 |
| 180620-175-80 μM: 3% Alginate | 70 | 26 | 31 | 33 |
| 180619-175-120 μM: 3% Alginate | 71 | 24 | 37 | 43 |
| | Avg: | 24 | 33 | 39 |

The invention claimed is:

1. A polymeric composition, comprising polymeric particles which contain one or more microorganisms in one or more multicellular aggregates embedded in a self-produced extracellular biogenic matrix, wherein the self-produced extracellular biogenic matrix comprises naphthazarin, and wherein at least one microorganism has a total concentration of at least $10^8$ CFU/g dry weight and storage at 30° C. for 14 weeks resulting in less than 1 log 10 loss CFU/g dry mass.

2. The polymeric composition of claim 1, wherein the composition comprises napthazarin in at least a 10 fold higher amount compared to a reference composition, wherein the reference composition is produced by culturing the microorganisms in a nutrient broth to a final concentration of $10^9$ CFU/ml, encapsulating the microorganisms in alginate beads, incubating the beads for 24 to 48 hours in fresh nutrient broth, washing the alginate beads, and then either lyophilizing the alginate beads or placing the alginate beads in hermetically sealed containers.

3. The polymeric composition of claim 1, wherein the self-produced extracellular biogenic matrix additionally comprises one or more compound selected from the group consisting of homocysteine, NAD+/NADH, tryptophan, thiamine, erythrose 4-phosphate, phenylalanine, pyridoxine phosphate, and adenine.

4. The polymeric composition of claim 3, wherein the self-produced extracellular biogenic matrix additionally comprises one or more of homocysteine, NAD+/NADH, tryptophan, thiamine, erythrose 4-phosphate, phenylalanine, pyridoxine phosphate, or adenine in at least a 1 fold higher amount compared to a reference composition, wherein the reference composition is produced by culturing the microorganisms in a nutrient broth to a final concentration of $10^9$ CFU/ml, encapsulating the microorganisms in alginate beads, incubating the beads for 24 to 48 hours in fresh nutrient broth, washing the alginate beads, and then either lyophilizing the alginate beads or placing the alginate beads in hermetically sealed containers.

5. The polymeric composition of claim 1, wherein the polymeric particles are wet and at least 1 of the one or more multicellular aggregates is between 14 μm and 43 μm in diameter.

6. The polymeric composition of claim 1, wherein the polymeric particles comprise a biodegradable polymer, wherein the biodegradable polymer is selected from the group consisting of albumin, collagen, gelatin, fibrinogen, casein, fibrin, hemoglobin, transferrin, chitin, chitosan, hyaluronic acid, heparin, chondroitin, keratin sulfate, alginate, starch, dextrin, dextran, polylactic acid, polyglycolic acid, lactic acid-glycolic acid copolymer, polyhydroxybutyric acid, polycaprolactone, polyanhydride, agarose, agar, chitosan, and polyalkylcyanoacrylate.

7. The polymeric composition of claim 1, wherein at least one of the polymeric particles has a diameter of less than 200 μm.

8. The polymeric composition of claim 1, wherein the one or more encapsulated microorganisms are bacterial or fungal cells.

9. The polymeric composition of claim 1, wherein the one or more encapsulated microorganisms comprise at least two microorganisms of distinct genetic origins.

10. The polymeric composition of claim 9, wherein the at least two microorganisms of distinct genetic origins are selected from at least two of the group archaea, protozoa, bacteria, fungi and algae.

11. The polymeric composition of claim 1, wherein the viability of at least one microorganism is maintained for a storage period of at least 35 weeks at 30° C.

\* \* \* \* \*